(12) United States Patent
Chung et al.

(10) Patent No.: US 9,745,578 B2
(45) Date of Patent: Aug. 29, 2017

(54) TARGETING MICRORNA MIR-409-3P TO TREAT PROSTATE CANCER

(71) Applicant: Cedars-Sinai Medical Center, Los Angeles, CA (US)

(72) Inventors: Leland W. K. Chung, Beverly Hills, CA (US); Sajni Josson, Los Angeles, CA (US); Murali Gururajan, Los Angeles, CA (US); Anjali Jain, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 14/863,828

(22) Filed: Sep. 24, 2015

(65) Prior Publication Data

US 2016/0017331 A1 Jan. 21, 2016

Related U.S. Application Data

(63) Continuation-in-part of application No. 14/360,489, filed as application No. PCT/US2012/067403 on Nov. 30, 2012.

(60) Provisional application No. 61/565,226, filed on Nov. 30, 2011, provisional application No. 62/055,215, filed on Sep. 25, 2014.

(51) Int. Cl.
*A61K 48/00* (2006.01)
*C07H 21/02* (2006.01)
*C07H 21/04* (2006.01)
*C12N 15/113* (2010.01)

(52) U.S. Cl.
CPC ...... *C12N 15/113* (2013.01); *C12N 2310/113* (2013.01); *C12N 2310/14* (2013.01); *C12N 2310/3233* (2013.01); *C12N 2310/531* (2013.01)

(58) Field of Classification Search
CPC .............................. C12N 15/113; A61K 48/00
See application file for complete search history.

(56) References Cited

U.S. PATENT DOCUMENTS

| | | | |
|---|---|---|---|
| 7,709,616 B2 | 5/2010 | Bentwich et al. | |
| 8,597,892 B2 * | 12/2013 | Shelton | C12Q 1/6886 435/6.14 |
| 2007/0065844 A1 | 3/2007 | Golub et al. | |
| 2008/0261908 A1 | 10/2008 | Croce et al. | |
| 2009/0092974 A1 | 4/2009 | Davison et al. | |
| 2010/0216139 A1 | 8/2010 | Galas et al. | |
| 2010/0297652 A1 | 11/2010 | Shelton et al. | |
| 2010/0330155 A1 * | 12/2010 | Berry | C12N 15/111 424/450 |
| 2011/0053158 A1 | 3/2011 | Mambo et al. | |
| 2011/0054009 A1 | 3/2011 | Croce et al. | |
| 2012/0108462 A1 | 5/2012 | Keller et al. | |
| 2014/0323551 A1 | 10/2014 | Chung et al. | |

FOREIGN PATENT DOCUMENTS

| | | | | |
|---|---|---|---|---|
| CN | 104080461 A | 10/2014 | | |
| EP | 2785355 | 10/2014 | | |
| JP | 2015-504847 | 2/2015 | | |
| WO | WO 2008/061537 | * | 5/2008 | ........... C12N 15/113 |
| WO | 2009043353 A2 | 4/2009 | | |
| WO | WO 2009/108860 | * | 9/2009 | ........... C12N 15/113 |
| WO | 2011117353 A1 | 9/2011 | | |
| WO | 2013082499 A1 | 6/2013 | | |

OTHER PUBLICATIONS

EP 12854115.8 extended European search report dated Oct. 29, 2015.
PCT/US2012/067403 International Search Report dated Apr. 19, 2013; 6 pages.
PCT/US2012/067403 Written Opinion dated Apr. 19, 2013; 7 pages.
PCT/US2012/067403 International Preliminary Report on Patentability dated Jun. 3, 2014; 8 pages.
GenBank ED385484. AUAC-aap88g05.b1 Ascaris suum whole genome shotgun library (PMAJ_4_GSS) Ascaris suum genomic, genomic survey sequence (2006), [online], Retrieved from <URL: http://www.ncbi.nlm.nih.gov/nucgss/ED385484>.
GenBank FP089691. Sus scrota chromosome 9 clone CH242-273B10, Working Draft Sequence, 7 unordered pieces. (2009), [online], Retrieved from <URL: http://www.ncbi.nlm.nih.gov/nuccore/FP089691>.
GenBank FD724631. CAAA6996.rev CAAA Petromyzon marinus Petromyzon marinus cDNA clone CAAA6996 3-, mRNA sequence. (2008), [online], Retrieved from <URL: http://www.ncbi.nlm.nih.gov/nucest/FD724631>.
GenBank EB330539. CNSN01-F-135479-501 Normalized CNS Library (juvenile 1) Aplysia caifornica cDNA clone CNSN01-F-135479 5-, mRNA sequence. (2007), [online], Retrieved from <URL:http://www.ncbi.nlm.nih.gov/nucest/EB330539>.
Croce CM. Causes and Consequences of microRNA Dysregulation in Cancer. Nat Rev Genet (2009). 10 (10):704-714.
Lages et al. MicroRNA and Target Protein Patterns Reveal Physiopathologial Features of Glioma Subtypes. PLoS One (2011). 6(5) e20600: pp. 1-12.
Peng et al. Identification of miRs-143 and -145 that is Associated with Bone Metastasis of Prostate Cancer and Involved in the Regulation of EMT. PLoS One (2011). 6(5) e20341: pp. 1-13.
EP 12854115.8 Partial Supplemental European Search Report dated Jul. 3, 2015.
Zheng et al. MicroRNA-409 suppresses tumour cell invasion and metastasis by directly targeting radixin in gastric cancers. Oncogene (2012) 31:4509-4516.

* cited by examiner

*Primary Examiner* — Amy Bowman
(74) *Attorney, Agent, or Firm* — Nixon Peabody LLP

(57) ABSTRACT

The present invention describes methods of treating cancer, cancer metastasis, and drug resistant cancers using miRNA inhibitors; for example, inhibitors of miR-409-5p, miR-409-3p, miR-154*. Also described are methods of using the miRNA as biomarkers; for example, to predict responsiveness to a cancer drug, to detect a disease state of cancer.

8 Claims, 22 Drawing Sheets

A

B

C

D

A

B

C

A

B  ARCaP$_M$-C

C

D

E

FIG. 7A
RSU1, Chr 10, 3'UTR binding sites for miR-409-5p and -3p
RSU1, miR-409-5p, 7 mer-1A, Position 335-341 of RSU1 3' UTR, conserved
```
5'      ...AAUAAUUAAAAUCAUGUAACCAU... (SEQ ID NO:29)
                       | | |  | | |
3'      UACGUUUCAACGAGCCCAUUGGA     (SEQ ID NO:30)
```
RSU1, miR-409-3p, 7mer-1A, Position 216-222 of RSU1 3' UTR, poorly conserved
```
5'      ...UCCAUUUGUUUCUUUAACAUUAC... (SEQ ID NO:31)
                       | | |  | | |
3'      UCCCCAAGUGGCUCGUUGUAAG  (SEQ ID NO:32)
```
FIG. 7B
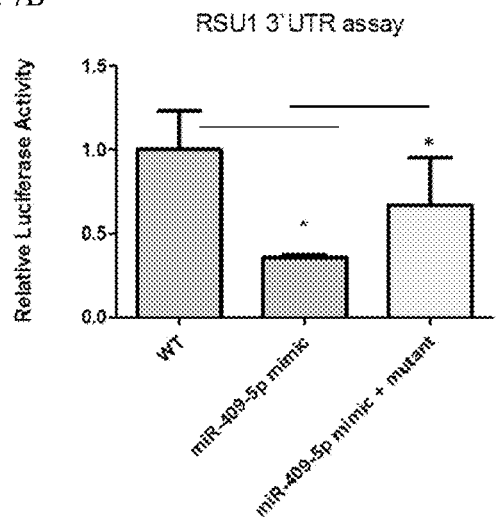
FIG. 7C
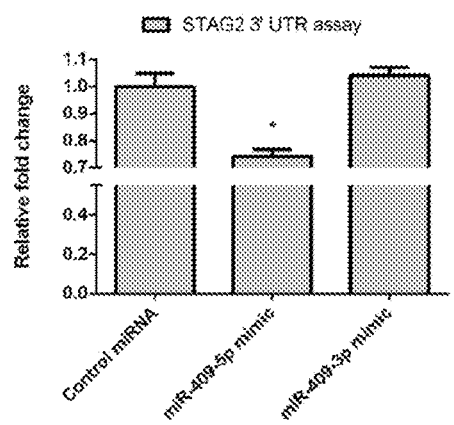

Human prostate cancer bone metastatic tissues (40X)
Tissue # 1      Tissue # 2

TARGETING MICRORNA MIR-409-3P TO TREAT PROSTATE CANCER

CROSS-REFERENCE TO RELATED APPLICATIONS

This application is a continuation-in-part of U.S. application Ser. No. 14/360,489, filed May 23, 2014, which is a National Phase of International Application No. PCT/US2012/067403, filed Nov. 30, 2012, which designated the U.S. and that International Application was published under PCT Article 21(2) in English, and which includes a claim of priority under 35 U.S.C. §119(e) to U.S. provisional patent application No. 61/565,226, filed Nov. 30, 2011, the entirety of which is hereby incorporated by reference. This application also includes a claim of priority under 35 U.S.C. §119(e) to U.S. provisional patent application No. 62/055,215, filed Sep. 25, 2014, the entirety of which is hereby incorporated by reference.

STATEMENT REGARDING FEDERALLY-SPONSORED RESEARCH

This invention was made with Government support under Grant No. CA122602 awarded by the National Institutes of Health. The Government has certain rights in the invention.

FIELD OF INVENTION

This invention relates to micro RNAs and cancer; particularly, to prostate cancer bone metastasis and drug resistant lung cancer.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Bone is the second most common site of cancer metastasis, harboring over 70% of cancer metastases from prostate and breast cancers. Advanced-stage cancer patients develop bone metastases either with or without hormonal therapy, radiation therapy, chemotherapy, and immunotherapy, and currently there is no effective treatment. The pathogenesis of bone metastases remains poorly understood. Impairment of stroma cell function in the cancer microenvironment is believed to be an important step in tumor progression. Fibroblasts adjacent to cancer cells in the prostate are structurally and functionally different from normal fibroblast in the prostate. These cancer associated fibroblasts (CAFs), have different gene expression profiles from the normal fibroblasts. Cancer cells and stromal cells interact through physical contact, soluble factors and insoluble extra-cellular matrix factors. The CAFs have been shown to play a critical role in tumorigenesis. Studies show that loss of Transforming growth factor-beta type II receptor gene, in mouse fibroblast resulted in intraepithelial neoplasia in prostate. One of the mechanism by which cancer cells metastasize is by undergoing epithelial to mesenchymal transition (EMT). EMT is a conserved embryonic process where polarized immotile epithelial cells transition to apolar motile mesenchymal cells. EMT is associated with cancer migration, invasion and metastasis. The common feature of EMT is loss of E-cadherin and increase in vimentin and N-cadherin. In cancer, EMT allows benign tumors to infiltrate the surrounding tissue and metastasize to other organs.

MiRNAs are non-coding RNAs of 18-24 nucleotides that bind to sites of complementarity in the 3' untranslated regions of messenger RNAs and inhibit their translation. A single miRNA can target several mRNA and regulate cellular pathways and cell fate. Several miRNA have been dysregulated in cancer, some of these are oncogenic (oncomiR) or they function as tumor suppressors. MiRNA have also shown to play a role in metastasis and have been termed 'metastamirs'. Several miRNAs have been shown to promote metastasis such as miR-10b in brain cancer, miR-21 in colorectal cancer, miR-184 in PCa. A few miRNA have been described which suppress PCa bone metastasis, such as miR-143, miR-145 and miR-203.

The lack of effective treatment for cancers, and particularly drug resistant cancers, along with the prevalence of bone metastasis shows a need in the art for additional therapies as well as biomarkers to discover and develop cancer therapeutics.

SUMMARY OF INVENTION

The following embodiments and aspects thereof are described and illustrated in conjunction with compositions and methods which are meant to be exemplary and illustrative, not limiting in scope.

Various embodiments of the present invention provides for a method, comprising: providing a miRNA inhibitor; and administering the miRNA inhibitor to a subject in need of treatment for cancer, in need of treatment for cancer metastasis, or in need of lowering or treatment for cancer drug resistance to treat cancer, to treat cancer metastasis, or to lower or treat cancer drug resistance.

In various embodiments, the method can further comprise administering to the subject radiation treatment or chemotherapy treatment.

In various embodiments, the cancer can be prostate cancer, lung cancer, breast cancer, metastatic cancer, cancer metastasis to the bone, metastatic prostate cancer, metastatic lung cancer, or metastatic breast cancer.

In various embodiments, the miRNA inhibitor can be capable of inhibiting miR-379, miR-379*, miR-193b, miR-193b*, miR-409-5p, miR-409-3p, miR-154, and/or miR-154*. In particular embodiments, the miRNA inhibitor can be capable of inhibiting mature miR-379, miR-379*, miR-193b, miR-193b*, miR-409-5p, miR-409-3p, miR-154, and/or miR-154*.

In various embodiments, the miRNA inhibitor can be a siRNA directed against a mature miRNA.

In particular embodiments, the miRNA inhibitor can be a shRNA directed against a mature miRNA. In certain embodiments, the miRNA inhibitor can be encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24 and can comprise administering the polynucleotide.

In various embodiments, the miRNA inhibitor can be a shRNA or a siRNA capable of interfering the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 7A depicts miR-409-5p and miR-409-3p binding sties in 3'UTR of RSU1 mRNA.

FIG. 7B depicts effect of miR-409-5p mimic binding on 3'UTR of RSU1 luciferase construct, both wild type and mutated construct.

FIG. 7C depicts effect of miR-409-5p mimic and miR-409-3p mimic on STAG2 3'UTR luciferase construct measured by luciferase assay.

DESCRIPTION OF THE INVENTION

Figure 1:
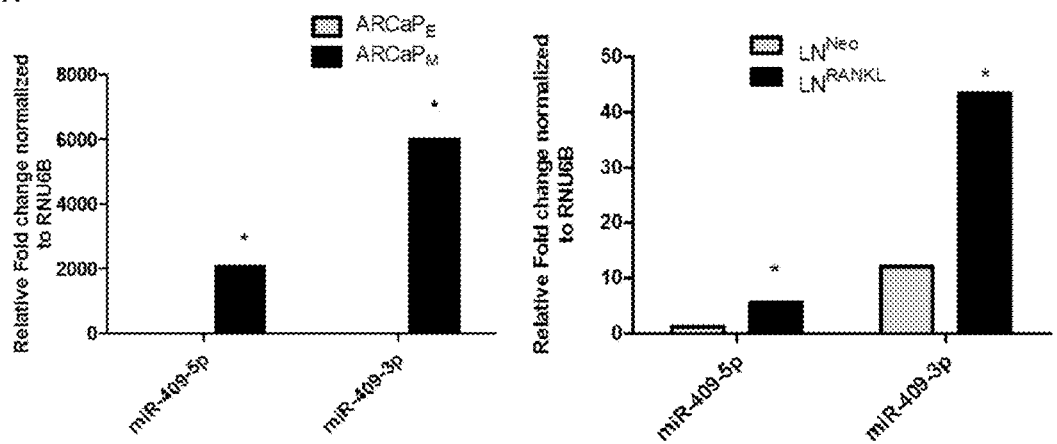
FIG. 1 shows that microRNA miR-409-3p/-5p in the imprinted DLK1-DIO3 cluster is overexpressed in bone metastatic EMT models of human PCa. A, miR-409-3p/-5p in bone metastatic PCa models (mesenchymal cells ARCaPM compared to ARCaPE) and (LNCaPNeo verses LNCaPRANKL PCa cells). All miRNA and RNA analysis were performed by qRT-PCR analysis. B, mRNA levels of MEG9 of ARCaPE and ARCaPM PCa cells. C, miR-409-3p/-5p expression in H9 embryonic stem cells and, D, iPSCs. *: $p<0.05$ were considered to be statistically significant by t-test.
Figure 1:
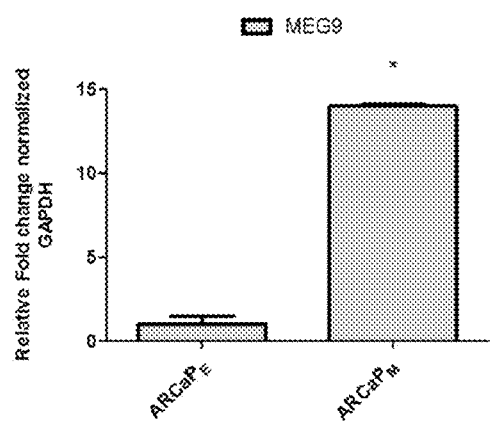
Figure 1:
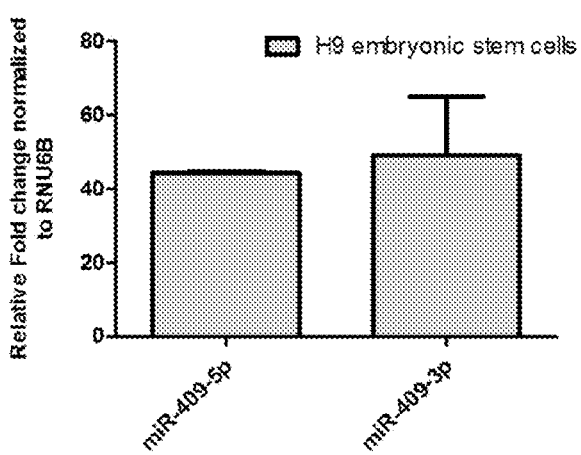
Figure 1:
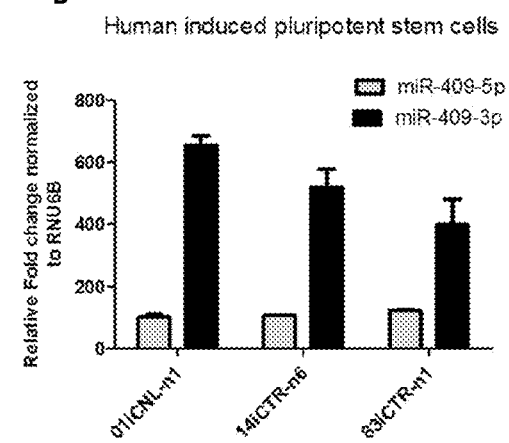

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Cancer" and "cancerous" refer to or describe the physiological condition in mammals that is typically characterized by unregulated cell growth. Examples of cancer include, but are not limited to, lung cancer, prostate cancer, breast cancer, colon cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus adult and newborn subjects, as well as fetuses, whether male or female, are intended to be including within the scope of this term.

"Treatment" and "treating," as used herein refer to both therapeutic treatment and prophylactic or preventative measures, wherein the object is to prevent, slow down and/or lessen the disease even if the treatment is ultimately unsuccessful.

MicroRNAs were demonstrated to be oncogenic in a variety of cancers, as described herein, the inventors profiled microRNA expression in multiple human bone metastatic prostate cancer cell lines and cancer associated stroma of the prostate and the bone. MiR-409-5p, miR-379 and miR-154* are highly expressed in both the cancer cells and the adjacent stroma and microRNA miR-409-5p is oncogenic in vivo, plays an important role in EMT and targeting miR-409-5p, miR-379 and miR-154* results in cell death of prostate cancer cells.

One of the largest microRNA clusters is on human chromosome 14q32. Its orthologous region in mouse is situated on the long arm of chromosome 12. About 10% of the microRNAs currently known in mouse and human are located in this cluster. This cluster is located within a well-known imprinted region that is characterized by parental-origin-specific mono-allelic expression of the encompassed genes (genomic imprinting is an epigenetically heritable mechanism where maternal or paternal alleles are methylated). In this study, the inventors demonstrate that microRNA members of the DLK-DIO3 cluster located in human chromosome including microRNA miR-409-5p, miR-379 and miR-154* are highly expressed in bone metastatic mesenchymal type prostate cancer cell lines. Overexpression of miR-409 in normal prostate resulted in tumor development in mice and tumors that developed varied from benign hyperplasia to adenocarcinoma. More importantly, miR-409-5p expression was upregulated in high Gleason score human prostate cancer tissue array. Inhibition of miR-409-5p, miR-379 and miR-154* either alone or blocking all three microRNAs together using a siRNA based approach resulted in increased cell death, reversal of epithelial to mesenchymal transition (EMT), biochemically and functionally. In addition to cancer cells, miR-409-5p was markedly upregulated in cancer associated stroma derived from prostate and the bone compared to normal stroma. Ectopic expression of miR-409 in normal stroma led to conversion of the stroma to a cancer associated stroma and miR-409 expressing stroma co-injected with less aggressive cancer cells had explosive tumor growth in vivo. This is the first demonstrated evidence of an oncogenic microRNA in prostate cancer in vivo. Thus, while not wishing to be bound by any particular theory, the inventor believes that miR-409-5p can be a therapeutic target to inhibit the vicious cycle involving bi-directional tumor stromal interactions in prostate cancer.

The latest development in the inventors' understanding of tumor microenvironment has provided a new opportunity for a fundamental change of approaches to cancer drug therapy. In addition to targeting the cancer cells, there is a need to focus on new molecular targets and pathways essential for the cells surrounding the cancer cells including stromal cells that have been demonstrated by recent studies to promote cancer growth. Impairment of stroma cell function in the cancer microenvironment is believed to be an important step in tumor progression. In addition, co-targeting of stromal cells in addition to cancer cells will lead to better killing of cancer cells. It has been demonstrated that fibromuscular stroma and stromal fibroblasts play regulatory role in prostate development and prostate carcinogenesis. In these studies, urogenital sinus mesenchyme (UGM) or embryonic/adult stromal fibroblasts were shown to drive the growth of UG epithelium and prostate cancer. These studies for the first time suggested that androgen receptor signaling from the stroma is critical for the development and differentiation of the normal prostate epithelium. Using cell recombination studies, the progression of prostate cancer from androgen-dependent to androgen-independent states and the subsequent progression to bone metastatic phenotypes can be achieved by cellular interactions between prostate cancer and prostate or bone stromal cells in mice in vivo or when co-cultured under three-dimensional (3D) conditions. It has been established that the fibroblasts adjacent to the cancer tissue or cancer-associated fibroblasts (CAF) are structurally and functionally different from fibroblasts adjacent to normal epithelium. These cells exhibit marked differences in gene expression profiles and have been shown to predict the progression of prostate cancer. The inventors demonstrated previously that the reciprocal cellular interaction between prostate cancer and CAF or stromal fibroblasts from different zonal origin. These findings, taken together, emphasized the important role of the stromal and tumor microenvironment in prostate cancer progression. These studies highlight the bidirectional interactions and co-evolution of tumor-stroma in cancer progression. Therapies that target many of the stromal factors have been successfully tested in preclinical models and/or in clinical trials to treat prostate cancer and other solid tumors.

EMT is a highly conserved process where polarized immotile epithelial cells transition to motile mesenchymal cells. EMT is commonly associated with cancer migration, invasion and metastasis. The common feature of EMT is the loss of E-cadherin and an increase in vimentin. In cancer, EMT facilitates benign tumors to infiltrate surrounding tissues and metastasize to soft tissues and the bone. In prostate cancer, EMT has been described in the androgen refractory prostate cancer (ARCaP) cell model. Prostate cancer cell lines and clinical samples are shown to express RANKL and secrete soluble factors such as β2M, which is not only responsible for driving EMT and bone metastasis of human prostate cancer cells but also exerted the same effects by promoting EMT and bone metastasis in human breast, renal and lung cancer cells. The resulting ARCaP$_M$ cells had high levels of the mesenchymal markers such as vimentin, N-cadherin and Snail and exhibit 100% incidence of bone metastasis when injected intracardially.

In conclusion, the inventors provide evidence that oncogenic microRNA miR-409-5p mediated regulation of gene expression in fibroblasts differentially affects epithelial growth and oncogenesis. Previous studies have indicated that secretory factors like TGF-β and its signaling through its receptor in stromal cells influence the carcinogenesis process in adjacent epithelia. The inventors' study defines the role of posttranscriptional regulators of gene expression (microRNAs) can suppress tumor suppressor genes and activate pleiotropic growth factors like beta2-microglobulin in stromal cells and thus can have an effect on adjacent epithelial cells in vivo. The phenotype of the cancer ranges from prostate intraepithelial neoplasia to adenocarcinoma. Strikingly, miR-409-5p is also expressed by metastatic prostate cancer cells and its inhibition leads to cell death. In addition to miR-409-5p, targeting other members of DLK- DIO3 cluster including miR-379 and miR-154* can be a therapeutic target to inhibit the vicious cycle involving bi-directional tumor stromal interactions in prostate cancer.

Figure 2:
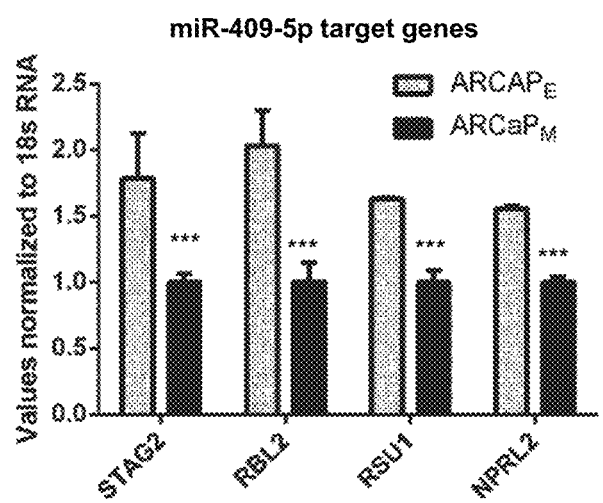
FIG. 2 shows that miR-409 inhibits tumor suppressor genes in prostate cancer. A, mRNA targets of miR-409-5p: STAG2, RBL2, RSU1 and NPRL2 and mRNA targets of miR-409-3p: RSU1, PHC3 and TUSC1, assayed by triplicate wells in qRT-PCR of ARCaPE and ARCaPM cells. The representative RT-PCR is shown. The experiment was repeated twice. B, Western analysis of STAG2 and RSU1 in ARCaPE and ARCaPM PCa cells. C and D, Cytoscape images of miR-409-3p and miR-409-5p signaling pathways. *: $p<0.05$ were considered to be statistically significant by t-test.
Figure 2:
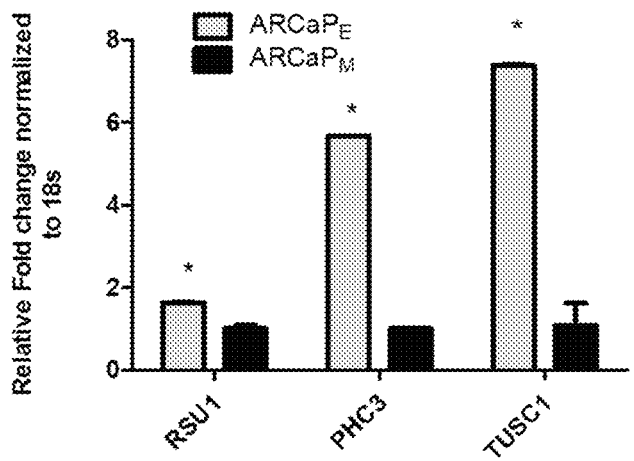
Figure 2:
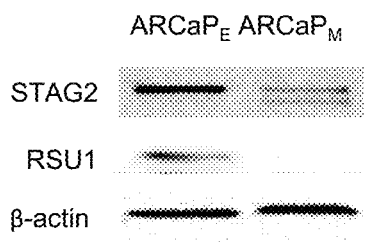
Figure 2:
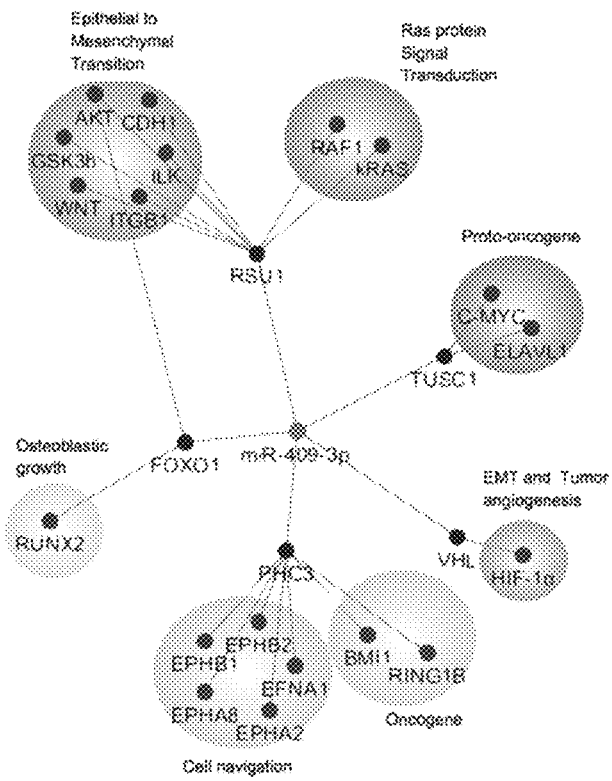
Figure 2:
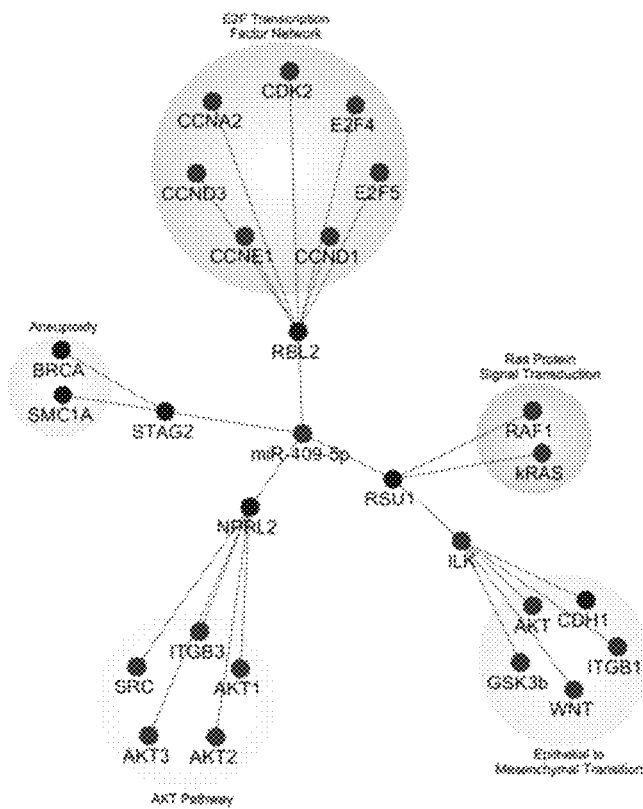

To understand the biology of noncoding RNAs in EMT and cancer bone metastasis and to identify novel biomarkers and/or therapeutic targets, we profiled miRNAs in unique EMT models of human PCa, developed in our laboratory. miR-409-3p/-5p, located within the DLK1-DIO3 cluster was highly upregulated in two PCa cell lines with mesenchymal phenotype and with bone metastatic potential (FIG. 1). The miRNA members of the DLK1-DIO3 cluster has been shown to be important for totipotency during embryogenesis and induced pluripotent stem cell formation. We report an unexpected discovery of the oncogenic role of miR-409-3p/-5p, which is expressed by embryonic stem cells and pluripotent stem cells, to promote PCa development and metastasis. Specifically, we showed that miR-409-3p/-5p: 1) is elevated in human PCa tumor tissues and correlates with PCa patients progression free survival, 2) can transform normal mouse prostate epithelium to exhibit tumorigenic phenotype and promote the growth and invasion of human PCa cells by downregulating tumor suppressor genes in vitro and in vivo, 2) can promote EMT and sternness of prostate epithelium in vivo, and 3) inhibition of miR-409-5p results in decreased bone metastatic tumor growth and increase in survival. Thus, miR-409 can be a new biomarker for cancer detection and an attractive new therapeutic target for PCa treatment.

miR-409 appears to mediate its tumorigenic effects through targeting of tumor suppressor genes (FIG. 2, 4, 5). One such target gene of miR-409-3p and -5p is RSU1. Previous studies have shown that RSU1 protein blocks the oncogenic Ras/MAPK pathway and integrin-linked kinase (ILK) pathway in PCa. Another, target gene for miR-409-5p appears to be STAG2. In the tumor cells, STAG2 is part of the cohesion complex, where deregulation of the members of the cohesion complex is thought to cause aneuploidy, cancer initiation and progression. In addition to STAG2, miR-409-5p appears to target NPRL2, a tumor suppressor protein decreased in solid tumors. There are differences in the genes targeted by miR-409-3p and miR-409-5p. At the same time, they do share some similar targets. Thus, miR-409-3p and miR-409-5p could be considered as distinct miRNAs with some shared functions.

Figure 10:
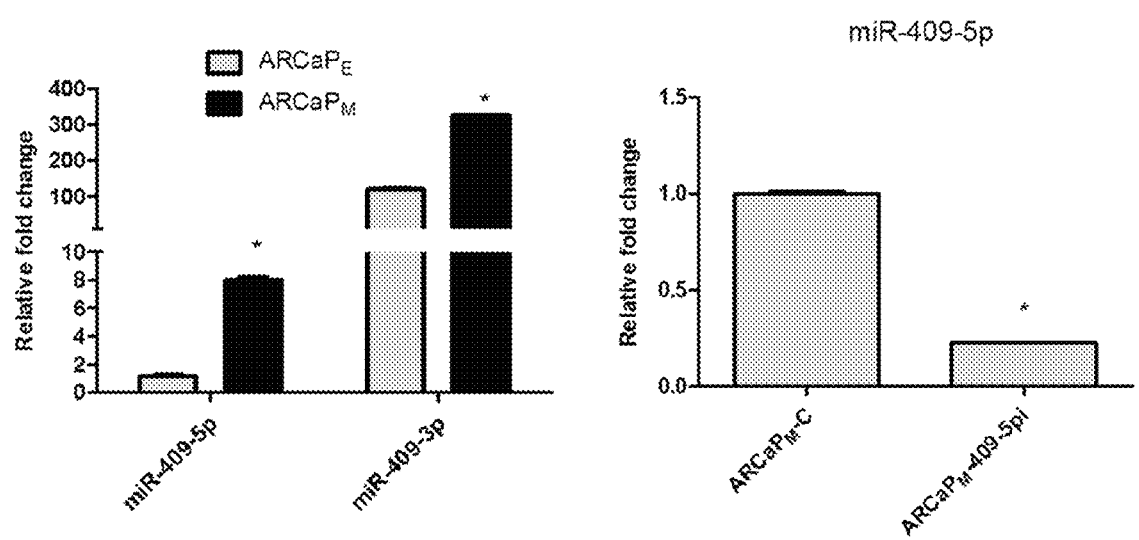
FIG. 10 depicts miR-409-5p and miR-409-3p in exosomes from $ARCaP_E$ and $ARCaP_M$ PCa cells measured by qRT-PCR, and miR-409-5p levels in exosomes from $ARCaP_M$-C and $ARCaP_M$-409-5pi PCa cells measured by qRT-PCR.

Orthotopic delivery of miR-409-3p/-5p in mouse prostate resulted in adenocarcinoma as well as prostatic hyperplasia. This dual phenotype could be attributed to difference in uptake of levels of miR-409-3p/-5p by the mouse prostate. miR-409-3p was found to be elevated in the serum of PCa patients with high Gleason score. Consistently, we found that the metastatic ARCaPM cells secrete higher levels of miR-409 and inhibition of miR-409-5p in these cells decreases this process (FIG. 10). Our metastatic model involves injection of cells into the blood stream and hence sites of tumor formation could be sites that permit tumor growth, and in our study it is the bone.

Figure 6:
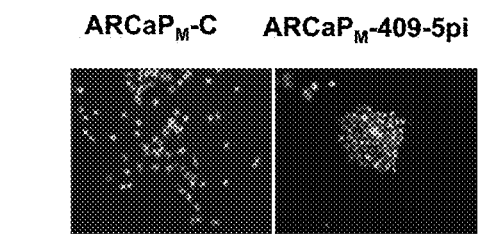
FIG. 6 shows that inhibition of miR-409-5p results in decreased bone metastasis in PCa in vivo. A, Morphological EMT changes in miR-409-5p inhibited ARCaPM cells; magnification 10×. RNA expression assayed by qRT-PCR of EMT markers, E-cadherin and N-cadherin. Migration and invasion assay of ARCaPM-C and ARCaPM-409-5pi PCa cells (n=3). B, Metastatic lesions observed by luciferase imaging of tumors of ARCaPM-C cells and ARCaPM-409-5pi cells in SCID/Beige mice following intra-cardial injections (N=5). C, Kaplan Meier survival curve of mice injected with ARCaPM-C cells (bottom line) and ARCaPM-409-5pi (top line) cells mice. D, X-ray image of metastatic bone lesion from ARCaPM-C bone tumors. E, Tumor dye (IR-783 dye) uptake by ARCaPM-C metastatic tumor from a representative mouse.
Figure 6:
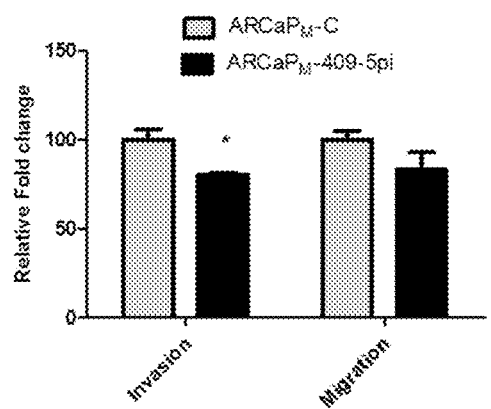
Figure 6:
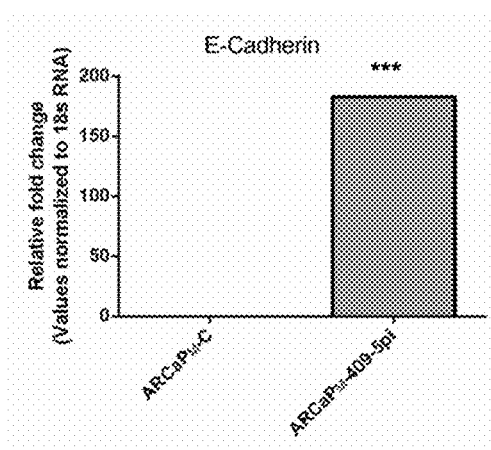
Figure 6:
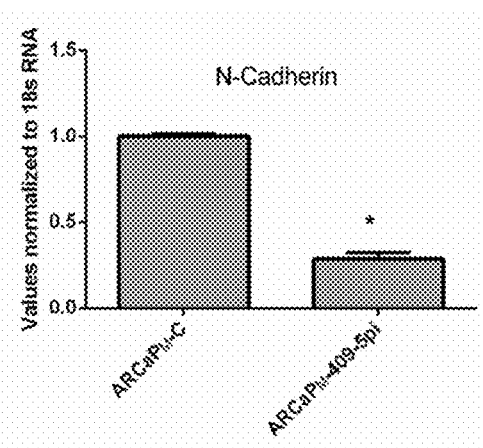
Figure 6:
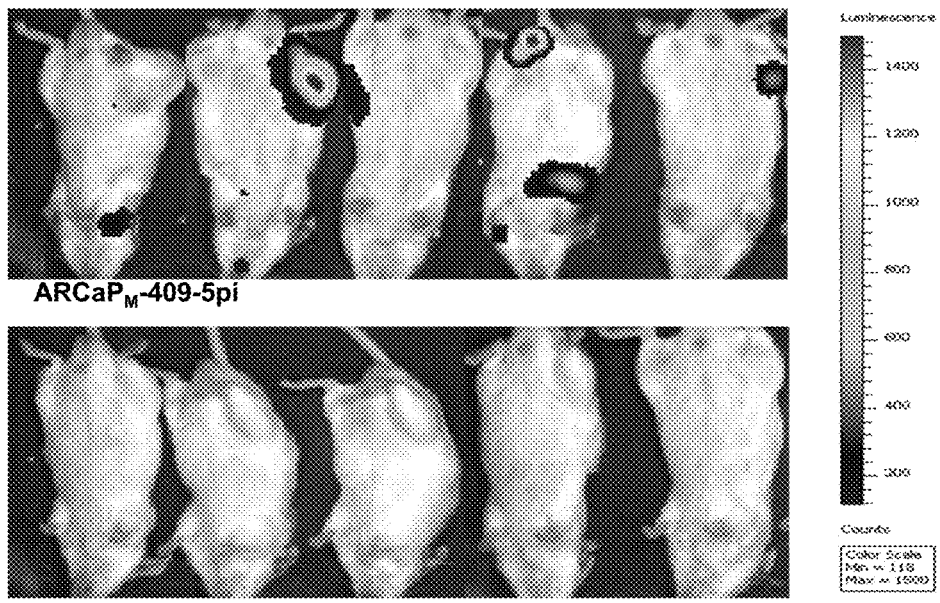
Figure 6:
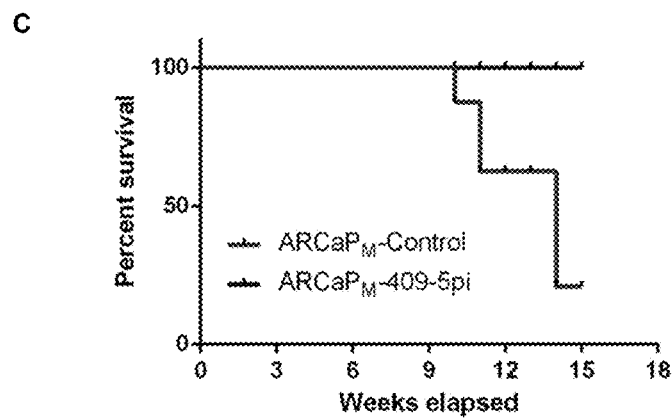
Figure 6:
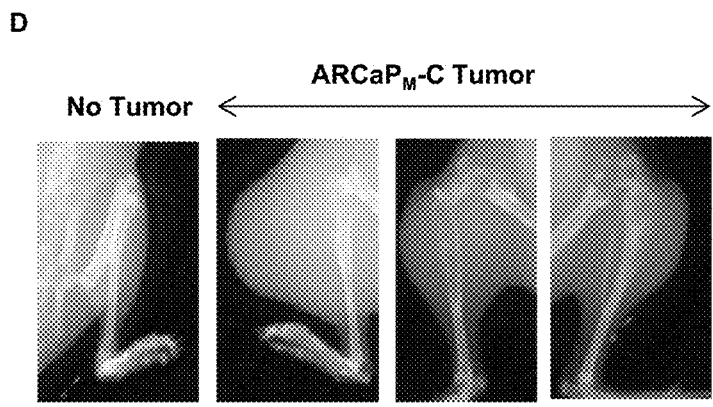
Figure 6:
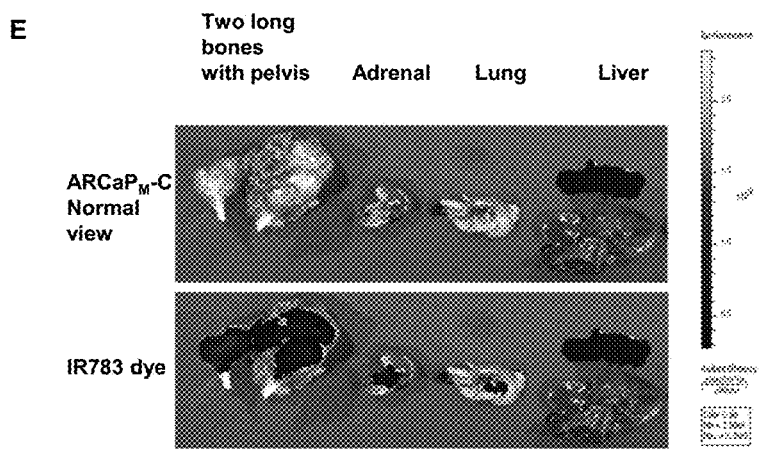

Our data indicates that miR-409-3p and -5p are elevated in the tumor tissues of PCa and can predict poor prognosis and prostate cancer patient progression free survival. It was also observed that miR-409-3p and miR-409-5p co-localized with higher Gleason score compared to low Gleason score (data not shown). Thus, both the miRNAs are active in more aggressive cancer and together induce tumorigenesis. Inhibition of miR-409-5p in vitro resulted in decreased growth and MET, and this was extended in the in vivo setting where miR-409-5pi cells did not grow, thus inhibiting the metastatic ability of highly aggressive bone metastatic PCa cells in vivo (FIG. 6).

In summary, our study demonstrates the oncogenic roles of miR-409-3p/-5p that is capable of promoting the malignant transformation of prostate epithelium in mice, including EMT, stemness and bone metastasis.

Figure 11:
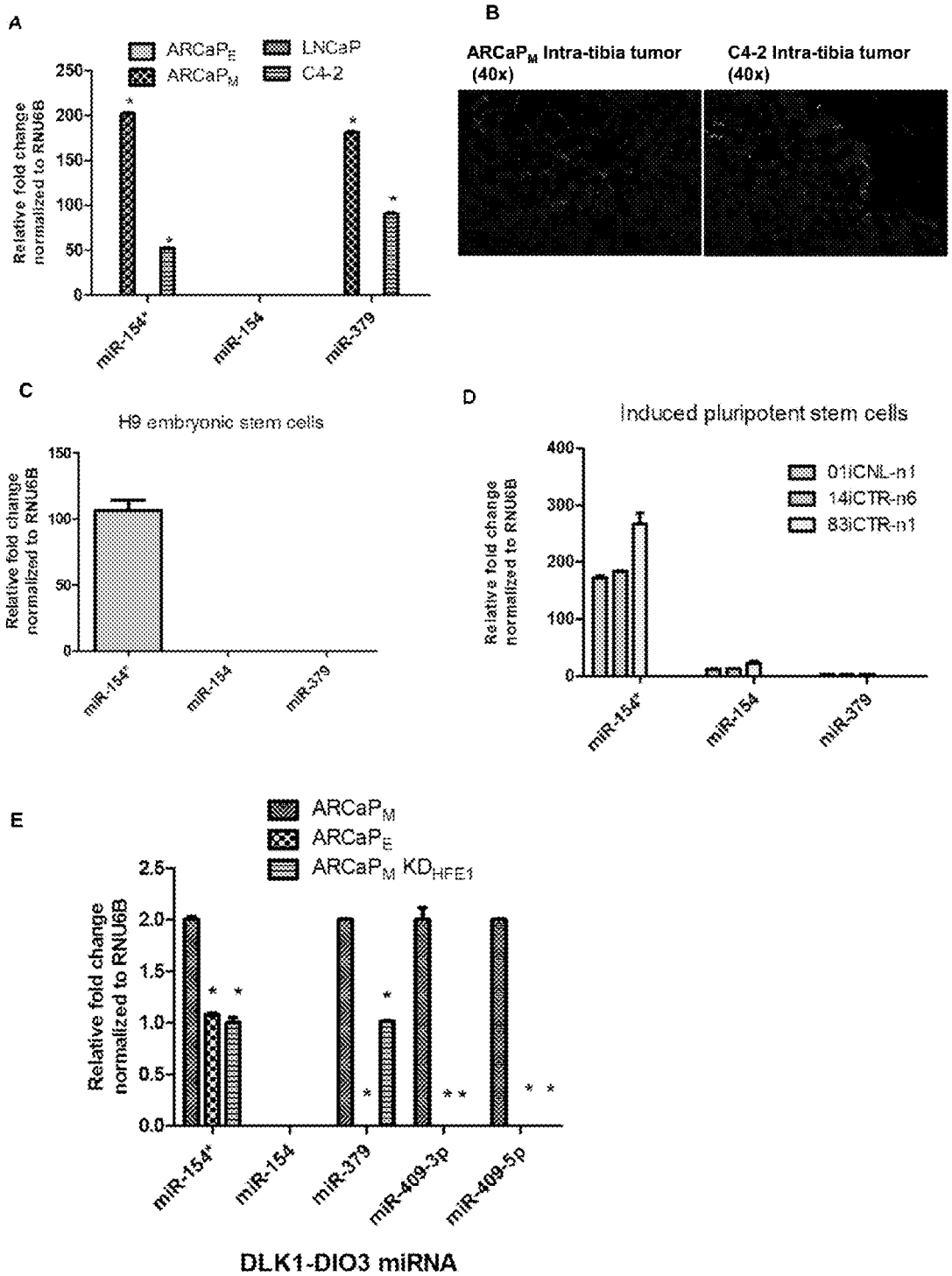
FIG. 11 shows that members of the DLK1-DIO3 miRNA cluster (miR-154/154* and miR-379) is overexpressed in aggressive bone metastatic EMT models of human PCa. (A) miRNA expression of miR-154/154* and miR-379 in PCa models (mesenchymal cells ARCaP$_M$ compared to ARCaP$_E$ and LNCaP verses C4-2 PCa cells) by qRT-PCR analysis. (B) miRNA stained or miR-154* stained PCa mouse bone metastatic models (C4-2 and ARCaP$_M$ cells) and assayed by ISH-QD analysis (Magnification 40×). miR-154* stained in red, nucleus stained with DAPI. (C), (D) miRNA expression of miR-154/154* and miR-379 in H9 embryonic stem cells and iPS cells by qRT-PCR. (left column 01iCNL-n1, middle column 14iCTR-n6, right column 83iCTR-n1) (E) miRNA expression in EMT models in PCa, mesenchymal cells-ARCaP$_M$, epithelial cells-ARCaP$_E$ and ARCaP$_M$ KD$^{HFE1}$, assayed by qRT-PCR. *: p<0.05 were considered to be statistically significant by one way ANOVA-Tukey analysis.

To understand the biology of the miRNAs of the DLK1-DIO3 mega cluster in EMT and cancer bone metastasis and to identify novel biomarkers and/or therapeutic targets, we probed for specific miRNAs of this mega cluster in unique EMT models of human PCa developed in our laboratory. Specifically, the miRNAs miR-154* and miR-379, located within the DLK1-DIO3 cluster, were highly upregulated in two PCa cell lines with a mesenchymal phenotype and with bone metastatic potential (FIG. 11). The miRNA members of the DLK1-DIO3 cluster have been shown to be important for totipotency during embryogenesis and induced pluripotent stem cell formation. We uncovered a surprising role for miR-154* and miR-379, which is expressed by embryonic stem cells and pluripotent stem cells, to promote PCa development and metastasis. Specifically, we show that: 1) miR-154* and miR-379 are elevated in human PCa tumor tissues and correlates with PCa patient progression free survival, 2) can promote EMT of PCa cells in vitro, and 3) inhibition of miR-154* results in decreased bone metastatic tumor growth and increase in survival.

Figure 15:
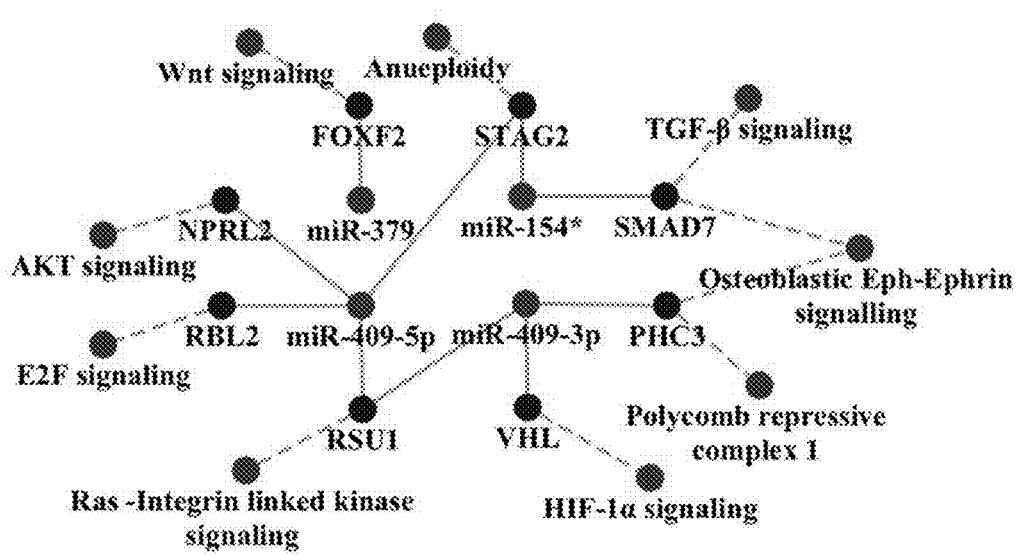
FIG. 15 depicts cytoscape analysis of target genes and signaling pathways altered by miR-409-3p/5p, miR-154* and miR-379 in the DLK1-DIO3 cluster. miRNA in this cluster target tumor suppressors which block several pathways in human cancer. Red dots represent activation of miRNA and oncogenic pathways and blue dots represent inhibition of tumor suppressor genes.

The primary functions of miR-154* is to repress tumor suppressors, modulate the expression of EMT, and stemness to mediate downstream convergent signal axes. Inhibition of miR-154* resulted in increased E-cadherin and decreased invasion in vitro. miR-154* depleted PCa cells had decreased bone metastasis and increased survival. miR-154* mediates its effects by downregulating its target gene, STAG2 which is a tumor suppressor. STAG2 plays a critical role in the cohesion complex and a decrease in STAG2 has been correlated with aneuploidy and cancer. Other miR-154* target genes may be involved such as SMAD7, which inhibits the TGF-β pathways, which are involved in EMT pathways. Interestingly, miR-154, the sense strand of miR-154* is undetectable or decreased in PCa models and in PCa patients. miR-154* is upregulated in both lung squamous cell carcinoma and lung adenocarcinoma patients. miR-379, another member of the DLK1-DIO3 cluster, located upstream of the miR-154 gene cluster, is moderately elevated in PCa cells (FIG. 11) Inhibition of miR-379 also resulted in reversal of EMT (MET), increased E-cadherin and decreased invasion. miR-379 expression in clinical specimens correlates with disease free survival of prostate cancer patients. Consistent with our observations, previous reports demonstrate that the miRNAs of the DLK1-DIO3 cluster are elevated in the serum of cancer patients compared to healthy patients. Consistent with our studies, it was shown that miR-379 is also elevated in metastatic PCa patients compared to patients with localized disease. Interestingly, other members of the DLK1-DIO3 mega cluster share similar mRNA target genes. STAG2 is targeted by both miR-154* and miR-409-5p, whereas RSU1 is targeted by both miR-409-5p and miR-409-3p. Thus the members of the cluster work synergistically and thus are elevated in the mesenchymal type PCa cells to promote EMT and metastasis (FIG. 15). We conclude that the miRNA members of the DLK1-DIO3 cluster promote EMT, stemness, and bone metastasis in PCa and thus have clinical implications in both the biomarker field and the therapeutic arena.

Various embodiments of the present invention are based, at least in part, on the inventors' findings described herein.

Treatments

Various embodiments of the present invention provide for a method of treating cancer in a subject in need thereof, comprising providing a miRNA inhibitor and administering the miRNA inhibitor to the subject.

Various embodiments of the present invention provide for a method of treating cancer metastasis in a subject in need thereof, comprising providing a miRNA inhibitor and administering the miRNA inhibitor to the subject.

Various embodiments of the present invention provide for a method of lowering or treating cancer drug resistance in a subject in need thereof, comprising providing a miRNA inhibitor and administering the miRNA inhibitor to the subject.

Various embodiments of the present invention provide for a method of treating cancer in a subject in need thereof, comprising providing a miRNA inhibitor and administering the miRNA inhibitor to the subject in combination with radiation treatment or chemotherapy treatment.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

In various embodiments, the miRNA inhibitor is capable of inhibiting miR-379, miR-379*, miR-193b, miR-193b*, miR-409-5p, miR-409-3p, miR-154, and/or miR-154*. In certain embodiments the miRNA inhibitor is capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*.

In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12.

In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence.

In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*).

In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In various embodiments, the present invention provides pharmaceutical compositions including a pharmaceutically acceptable excipient along with a therapeutically effective amount of a miRNA inhibitor. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch.

"Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, *acacia*, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Biomarkers

Various embodiments of the present invention provide for using miRNAs, DLK1-DIO3 region, and MEG9 as biomarkers for cancer and/or cancer associated tissues.

As such, various embodiments of the present invention provide for a method of predicting responsiveness to a cancer drug, comprising: obtaining a biological sample from a subject; testing the biological sample for a relative increase, decrease, or steady expression of a miRNA; and associating a relative increase of the miRNA expression level with a lower likelihood of drug responsiveness or associating a relative decrease or a steady expression level of the miRNA with a higher likelihood of drug responsiveness. In various embodiments, the method further comprises selecting a cancer drug to administer to the subject when a higher likelihood of drug responsiveness is predicted. In further embodiments, the method comprises administering a selected cancer drug to the subject.

In various embodiments, the cancer drug is a tyrosine kinase inhibitor (TKI). In certain embodiments, the TKI is an EGFR-TKI. In particular embodiments, the EGFR-TKI is Erlotinib (TARCEVA). In particular embodiments, the TKI is Gefitinib. In certain embodiments, the TKI is Apatinib, Cabozantinib, Canertinib, Crenolanib, Damnacanthal, Foretinib, Fostamatinib, Intedanib, Linifanib, Motesanib, Mubritinib, Vatalanib, or Vemurafenib.

In other embodiments, the cancer drug is an miRNA inhibitor.

In various embodiments, the miRNA inhibitor is capable of inhibiting miR-379, miR-379*, miR-193b, miR-193b*, miR-409-5p, miR-409-3p, miR-154, and/or miR-154*; an miRNA inhibitor capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*.

In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12.

In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence.

In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*).

In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In various embodiments, the miRNA expression that is measured for relative increase, decrease, or steady expression is miR-379, miR-379*, miR-193b, miR-193b*, miR-409-5p, miR-409-3p, miR-154, and/or miR-154*. In various embodiments, the miRNA is mature miR-379, miR-379*, miR-193b, miR-193b*, miR-409-5p, miR-409-3p, miR-154, and/or miR-154*. In particular embodiments, the miRNA is mature miR-379, miR-193b, miR-409-5p, miR-409-3p and/or miR-154*. In various embodiments, the miRNA has a sequence as disclosed by SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA has a sequence as disclosed by SEQ ID NO:2, SEQ ID NO:5, SEQ ID NO: 8, SEQ ID NO:9, or SEQ ID NO:12.

In particular embodiments, the miRNA expression that is measured for relative increase, decrease, or steady expression is miR-379, miR-379*, miR-154, and/or miR-154*. In various embodiments, the miRNA is mature miR-379, miR-379*, miR-154, and/or miR-154*. In particular embodiments, the miRNA expression that is measured for relative increase, decrease, or steady expression is mature miR-379 and/or miR-154*. In various embodiments, the miRNA expression that is measured for relative increase, decrease, or steady expression has the sequence as disclosed by SEQ ID NO:2, SEQ ID NO:3, SEQ ID NO: 11 or SEQ ID NO:12. In particular embodiments, the miRNA has the sequence as disclosed by SEQ ID NO:2 or SEQ ID NO:12.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

Various embodiments of the present invention also provide for a method of detecting a disease state of a cancer in a subject, comprising: obtaining a biological sample from a subject; testing the biological sample for a relative increase, decrease, or steady expression of a miRNA; and associating a relative increase of the miRNA expression level with a higher likelihood of having a cancer drug resistant disease state or associating a relative decrease or a steady expression level of the miRNA with cancer drug susceptible disease state. In various embodiments, the method further comprises selecting a cancer drug to administer to the subject when a cancer drug susceptible disease state is detected. In further embodiments, the method comprises administering a selected cancer drug to the subject.

In various embodiments, the cancer drug is a tyrosine kinase inhibitor (TKI). In certain embodiments, the TKI is an EGFR-TKI. In particular embodiments, the EGFR-TKI is Erlotinib (TARCEVA). In particular embodiments, the TKI is Gefitinib. In certain embodiments, the TKI is Apatinib, Cabozantinib, Canertinib, Crenolanib, Damnacanthal, Foretinib, Fostamatinib, Intedanib, Linifanib, Motesanib, Mubritinib, Vatalanib, or Vemurafenib.

In other embodiments, the cancer drug is an miRNA inhibitor. In various embodiments, the miRNA inhibitor is capable of inhibiting miR-379, miR-379*, miR-193b, miR-193b*, miR-409-5p, miR-409-3p, miR-154, and/or miR-154*; an miRNA inhibitor capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*. In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12. In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence. In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*). In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In various embodiments, the miRNA expression that is measured for a relative increase, decrease or steady expression is miR-379, miR-379*, miR-193b, miR-193b*, miR-409-5p, miR-409-3p, miR-154, and/or miR-154*. In various embodiments, the miRNA is mature miR-379, miR-379*, miR-193b, miR-193b*, miR-409-5p, miR-409-3p, miR-154, and/or miR-154*. In particular embodiments, the miRNA is mature miR-379, miR-193b, miR-409-5p, miR-409-3p and/or miR-154*. In various embodiments, the miRNA has a sequence as disclosed by SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA has a sequence as disclosed by SEQ ID NO:2, SEQ ID NO:5, SEQ ID NO: 8, SEQ ID NO:9, or SEQ ID NO:12.

In particular embodiments, the miRNA expression that is measured for a relative increase, decrease or steady expression is miR-379, miR-379*, miR-154, and/or miR-154*. In various embodiments, the miRNA is mature miR-379, miR-379*, miR-154, and/or miR-154*. In particular embodiments, the miRNA is mature miR-379 and/or miR-154*. In various embodiments, the miRNA has the sequence as disclosed by SEQ ID NO:2, SEQ ID NO:3, SEQ ID NO: 11 or SEQ ID NO:12. In particular embodiments, the miRNA has the sequence as disclosed by SEQ ID NO:2 or SEQ ID NO:12.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

Various embodiments of the present invention also provide for a method of detecting a disease state of a cancer in a subject, comprising: obtaining a biological sample from a subject; testing the biological sample for a relative increase, decrease, or steady expression of an DLK1-miRNA; and associating a relative increased expression the miRNA with metastatic disease state or associating a relative decreased or a steady expression level of DLK1-miRNA with a non-metastatic disease state.

In various embodiments, the miRNA expression that is measured for a relative increase, decrease or steady expression is miR-379, miR-379*, miR-193b, miR-193b*, miR-409-5p, miR-409-3p, miR-154, and/or miR-154*. In various embodiments, the miRNA is mature miR-379, miR-379*, miR-193b, miR-193b*, miR-409-5p, miR-409-3p, miR-154, and/or miR-154*. In particular embodiments, the miRNA is mature miR-379, miR-193b, miR-409-5p, miR-409-3p and/or miR-154*. In various embodiments, the miRNA has a sequence as disclosed by SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA has a sequence as disclosed by SEQ ID NO:2, SEQ ID NO:5, SEQ ID NO: 8, SEQ ID NO:9, or SEQ ID NO:12.

In certain embodiments, the metastatic disease state is bone metastasis. In certain embodiments, the cancer is metastatic prostate cancer. In certain embodiments, the cancer is metastatic lung cancer. In certain embodiments, the cancer is metastatic breast cancer.

Various embodiments of the present invention provide for a method of predicting responsiveness to a cancer drug, comprising: obtaining a biological sample from a subject; testing the biological sample for a relative increase, decrease, or steady expression of DLK1-DIO3 cluster/region; and associating a relative increased expression level of the DLK1-DIO3 cluster/region with a lower likelihood of drug responsiveness or associating a relative decreased or a steady expression level of the DLK1-DIO3 cluster/region with a higher likelihood of drug responsiveness. In various embodiments, the method further comprises selecting a cancer drug to administer to the subject when a higher likelihood of drug responsiveness is detected. In further embodiments, the method comprises administering a selected cancer drug to the subject.

In various embodiments, the cancer drug is a tyrosine kinase inhibitor (TKI). In certain embodiments, the TKI is an EGFR-TKI. In particular embodiments, the EGFR-TKI is Erlotinib (TARCEVA). In particular embodiments, the TKI is Gefitinib. In certain embodiments, the TKI is Apatinib, Cabozantinib, Canertinib, Crenolanib, Damnacanthal, Foretinib, Fostamatinib, Intedanib, Linifanib, Motesanib, Mubritinib, Vatalanib, or Vemurafenib.

In other embodiments, the cancer drug is an miRNA inhibitor. In various embodiments, the miRNA inhibitor is capable of inhibiting miR-379, miR-379*, miR-193b, miR-193b*, miR-409-5p, miR-409-3p, miR-154, and/or miR-154*; an miRNA inhibitor capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*. In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12. In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence. In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*). In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

Various embodiments of the present invention also provide for a method of detecting a disease state of a cancer in a subject, comprising: obtaining a biological sample from a subject; testing the biological sample for a relative increase, decrease, or steady expression of the DLK1-DIO3 cluster/region; and associating a relative increased expression level of the DLK1-DIO3 region with a cancer drug resistant disease state or associating a relative decreased or a steady expression level of the DLK1-DIO3 cluster/region with cancer drug susceptible disease state. In various embodiments, the method further comprises selecting a cancer drug to administer to the subject when a cancer drug susceptible disease state is detected. In further embodiments, the method comprises administering a selected cancer drug to the subject.

In various embodiments, the cancer drug is a tyrosine kinase inhibitor (TKI). In certain embodiments, the TKI is an EGFR-TKI. In particular embodiments, the EGFR-TKI is Erlotinib (TARCEVA). In particular embodiments, the TKI is Gefitinib. In certain embodiments, the TKI is Apatinib, Cabozantinib, Canertinib, Crenolanib, Damnacanthal, Foretinib, Fostamatinib, Intedanib, Linifanib, Motesanib, Mubritinib, Vatalanib, or Vemurafenib.

In other embodiments, the cancer drug is an miRNA inhibitor. In various embodiments, the miRNA inhibitor is capable of inhibiting miR-379, miR-379*, miR-193b, miR-193b*, miR-409-5p, miR-409-3p, miR-154, and/or miR-154*; an miRNA inhibitor capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*. In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12. In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence. In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*). In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

Various embodiments of the present invention also provide for a method of detecting a disease state of a cancer in a subject, comprising: obtaining a biological sample from a subject; testing the biological sample for a relative increase, decrease, or steady expression of DLK1-DIO3 cluster/region; and associating a relative increased expression of the DLK1-DIO3 cluster/region with metastatic disease state or associating a relative decreased or a steady expression level of DLK1-DIO3 cluster/region with a non-metastatic disease state.

In certain embodiments, the metastatic disease state is bone metastasis. In certain embodiments, the cancer is metastatic prostate cancer. In certain embodiments, the cancer is metastatic lung cancer. In certain embodiments, the cancer is metastatic breast cancer.

Various embodiments of the present invention provide for a method of predicting responsiveness to a cancer drug, comprising: obtaining a biological sample from a subject; testing the biological sample for a relative increase, decrease, or steady expression of MEG9; and associating a relative increased expression level of MEG9 with a lower likelihood of drug responsiveness or associating a relative decreased or a steady expression level of MEG9 with a higher likelihood of drug responsiveness. In various embodiments, the method further comprises selecting a cancer drug to administer to the subject when a higher likelihood of drug responsiveness is detected. In further embodiments, the method comprises administering a selected cancer drug to the subject.

In various embodiments, the cancer drug is a tyrosine kinase inhibitor (TKI). In certain embodiments, the TKI is an EGFR-TKI. In particular embodiments, the EGFR-TKI is Erlotinib (TARCEVA). In particular embodiments, the TKI is Gefitinib. In certain embodiments, the TKI is Apatinib, Cabozantinib, Canertinib, Crenolanib, Damnacanthal, Foretinib, Fostamatinib, Intedanib, Linifanib, Motesanib, Mubritinib, Vatalanib, or Vemurafenib.

In other embodiments, the cancer drug is an miRNA inhibitor. In various embodiments, the miRNA inhibitor is capable of inhibiting miR-379, miR-379*, miR-193b, miR-193b*, miR-409-5p, miR-409-3p, miR-154, and/or miR-154*; an miRNA inhibitor capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*. In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12. In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence. In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*). In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

Various embodiments of the present invention also provide for a method of detecting a disease state of a cancer in a subject, comprising: obtaining a biological sample from a subject; testing the biological sample for a relative increase, decrease, or steady expression of MEG9; and associating a relative increased expression the MEG9 with metastatic disease state or associating a relative decreased or a steady expression level of MEG9 with a non-metastatic disease state.

In certain embodiments, the metastatic disease state is bone metastasis. In certain embodiments, the cancer is metastatic prostate cancer. In certain embodiments, the cancer is metastatic lung cancer. In certain embodiments, the cancer is metastatic breast cancer.

Systems

Various embodiments of the present invention provide for a system for predicting responsiveness to a cancer drug, comprising: biological sample obtained from a subject; detection probes to test the biological sample for a relative increase, decrease, or steady expression of a miRNA. In various embodiments, the system further comprises a machine (e.g., computer) to associate a relative increase of the miRNA expression level with a lower likelihood of drug responsiveness or associate a relative decrease or a steady expression level of the miRNA with a higher likelihood of drug responsiveness.

In various embodiments, the cancer drug is a tyrosine kinase inhibitor (TKI). In certain embodiments, the TKI is an EGFR-TKI. In particular embodiments, the EGFR-TKI is Erlotinib (TARCEVA). In particular embodiments, the TKI is Gefitinib. In certain embodiments, the TKI is Apatinib, Cabozantinib, Canertinib, Crenolanib, Damnacanthal, Foretinib, Fostamatinib, Intedanib, Linifanib, Motesanib, Mubritinib, Vatalanib, or Vemurafenib.

In other embodiments, the cancer drug is an miRNA inhibitor. In various embodiments, the miRNA inhibitor is capable of inhibiting miR-379, miR-379*, miR-193b, miR-193b*, miR-409-5p, miR-409-3p, miR-154, and/or miR-154*; an miRNA inhibitor capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*. In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12. In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence. In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*). In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In various embodiments, the miRNA that is tested for a relative increase, decrease or steady expression is miR-379, miR-379*, miR-193b, miR-193b*, miR-409-5p, miR-409-3p, miR-154, and/or miR-154*. In various embodiments, the miRNA that is tested for a relative increase, decrease or steady expression is mature miR-379, miR-379*, miR-193b, miR-193b*, miR-409-5p, miR-409-3p, miR-154, and/or miR-154*. In particular embodiments, the miRNA that is tested for a relative increase, decrease or steady expression is mature miR-379, miR-193b, miR-409-5p, miR-409-3p and/or miR-154*. In various embodiments, the miRNA has a sequence as disclosed by SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA that is tested for a relative increase, decrease or steady expression has a sequence as disclosed by SEQ ID NO:2, SEQ ID NO:5, SEQ ID NO: 8, SEQ ID NO:9, or SEQ ID NO:12.

In particular embodiments, the miRNA that is tested for a relative increase, decrease or steady expression is miR-379, miR-379*, miR-154, and/or miR-154*. In various embodiments, the miRNA that is tested for a relative increase, decrease or steady expression is mature miR-379, miR-379*, miR-154, and/or miR-154*. In particular embodiments, the miRNA is mature miR-379 and/or miR-154*. In various embodiments, the miRNA that is tested for a relative increase, decrease or steady expression has the sequence as disclosed by SEQ ID NO:2, SEQ ID NO:3, SEQ ID NO: 11 or SEQ ID NO:12. In particular embodiments, the miRNA has the sequence as disclosed by SEQ ID NO:2 or SEQ ID NO:12.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

Various embodiments of the present invention also provide for a system for detecting a disease state of a cancer in a subject, comprising: a biological sample from a subject; detection probes to test the biological sample for a relative increase, decrease, or steady expression of a miRNA. In various embodiments, the system further comprises a machine (e.g., computer) to associate a relative increase of the miRNA expression level with a higher likelihood of having a cancer drug resistant disease state or associate a relative decrease or a steady expression level of the miRNA with cancer drug susceptible disease state.

In various embodiments, the cancer drug is a tyrosine kinase inhibitor (TKI). In certain embodiments, the TKI is an EGFR-TKI. In particular embodiments, the EGFR-TKI is Erlotinib (TARCEVA). In particular embodiments, the TKI is Gefitinib. In certain embodiments, the TKI is Apatinib, Cabozantinib, Canertinib, Crenolanib, Damnacanthal, Foretinib, Fostamatinib, Intedanib, Linifanib, Motesanib, Mubritinib, Vatalanib, or Vemurafenib.

In other embodiments, the cancer drug is an miRNA inhibitor. In various embodiments, the miRNA inhibitor is capable of inhibiting miR-379, miR-379*, miR-193b, miR-193b*, miR-409-5p, miR-409-3p, miR-154, and/or miR-154*; an miRNA inhibitor capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*. In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12. In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence. In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*). In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In various embodiments, the miRNA that is tested for a relative increase, decrease or steady expression is miR-379, miR-379*, miR-193b, miR-193b*, miR-409-5p, miR-409-3p, miR-154, and/or miR-154*. In various embodiments, the miRNA that is tested for a relative increase, decrease or steady expression is mature miR-379, miR-379*, miR-193b, miR-193b*, miR-409-5p, miR-409-3p, miR-154, and/or miR-154*. In particular embodiments, the miRNA that is tested for a relative increase, decrease or steady expression is mature miR-379, miR-193b, miR-409-5p, miR-409-3p and/or miR-154*. In various embodiments, the miRNA has a sequence as disclosed by SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA that is tested for a relative increase, decrease or steady expression has a sequence as disclosed by SEQ ID NO:2, SEQ ID NO:5, SEQ ID NO: 8, SEQ ID NO:9, or SEQ ID NO:12.

In particular embodiments, the miRNA that is tested for a relative increase, decrease or steady expression is miR-379, miR-379*, miR-154, and/or miR-154*. In various embodiments, the miRNA is mature miR-379, miR-379*, miR-154, and/or miR-154*. In particular embodiments, the miRNA that is tested for a relative increase, decrease or steady expression is mature miR-379 and/or miR-154*. In various embodiments, the miRNA that is tested for a relative increase, decrease or steady expression has the sequence as disclosed by SEQ ID NO:2, SEQ ID NO:3, SEQ ID NO: 11 or SEQ ID NO:12. In particular embodiments, the miRNA that is tested for a relative increase, decrease or steady expression has the sequence as disclosed by SEQ ID NO:2 or SEQ ID NO:12.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

Various embodiments of the present invention also provide for a system for detecting a disease state of a cancer in a subject, comprising: a biological sample from a subject; detection probes to test the biological sample for a relative increase, decrease, or steady expression of a DLK1-miRNA. In various embodiments, the system further comprises a machine (e.g., computer) to associate a relative increased expression the miRNA with metastatic disease state or associate a relative decreased or a steady expression level of DLK1-miRNA with a non-metastatic disease state.

In various embodiments, the miRNA is miR-379, miR-379*, miR-193b, miR-193b*, miR-409-5p, miR-409-3p, miR-154, and/or miR-154*. In various embodiments, the miRNA is mature miR-379, miR-379*, miR-193b, miR-193b*, miR-409-5p, miR-409-3p, miR-154, and/or miR-154*. In particular embodiments, the miRNA is mature miR-379, miR-193b, miR-409-5p, miR-409-3p and/or miR-154*. In various embodiments, the miRNA has a sequence as disclosed by SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA has a sequence as disclosed by SEQ ID NO:2, SEQ ID NO:5, SEQ ID NO: 8, SEQ ID NO:9, or SEQ ID NO:12.

In certain embodiments, the metastatic disease state is bone metastasis. In certain embodiments, the cancer is metastatic prostate cancer. In certain embodiments, the cancer is metastatic lung cancer. In certain embodiments, the cancer is metastatic breast cancer.

Various embodiments of the present invention provide for a system for predicting responsiveness to a cancer drug, comprising: a biological sample from a subject; detection probes to the biological sample for a relative increase, decrease, or steady expression of DLK1-DIO3 cluster/region. In various embodiments, the system further comprises a machine (e.g., computer) to associate a relative increased expression level of the DLK1-DIO3 cluster/region with a lower likelihood of drug responsiveness or associate a relative decreased or a steady expression level of the DLK1-DIO3 cluster/region with a higher likelihood of drug responsiveness.

In various embodiments, the cancer drug is a tyrosine kinase inhibitor (TKI). In certain embodiments, the TKI is an EGFR-TKI. In particular embodiments, the EGFR-TKI is Erlotinib (TARCEVA). In particular embodiments, the TKI is Gefitinib. In certain embodiments, the TKI is Apatinib, Cabozantinib, Canertinib, Crenolanib, Damnacanthal, Foretinib, Fostamatinib, Intedanib, Linifanib, Motesanib, Mubritinib, Vatalanib, or Vemurafenib.

In other embodiments, the cancer drug is an miRNA inhibitor. In various embodiments, the miRNA inhibitor is capable of inhibiting miR-379, miR-379*, miR-193b, miR-193b*, miR-409-5p, miR-409-3p, miR-154, and/or miR-154*; an miRNA inhibitor capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*. In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12. In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence. In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*). In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

Various embodiments of the present invention also provide for a system for detecting a disease state of a cancer in a subject, comprising: a biological sample from a subject; detection probes to test the biological sample for a relative increase, decrease, or steady expression of the DLK1-DIO3 cluster/region. In various embodiments, the system further comprises a machine (e.g., computer) to associate a relative increased expression level of the DLK1-DIO3 region with a cancer drug resistant disease state or associate a relative decreased or a steady expression level of the DLK1-DIO3 cluster/region with cancer drug susceptible disease state.

In various embodiments, the cancer drug is a tyrosine kinase inhibitor (TKI). In certain embodiments, the TKI is an EGFR-TKI. In particular embodiments, the EGFR-TKI is Erlotinib (TARCEVA). In particular embodiments, the TKI is Gefitinib. In certain embodiments, the TKI is Apatinib, Cabozantinib, Canertinib, Crenolanib, Damnacanthal, Foretinib, Fostamatinib, Intedanib, Linifanib, Motesanib, Mubritinib, Vatalanib, or Vemurafenib.

In other embodiments, the cancer drug is an miRNA inhibitor. In various embodiments, the miRNA inhibitor is capable of inhibiting miR-379, miR-379*, miR-193b, miR-193b*, miR-409-5p, miR-409-3p, miR-154, and/or miR-154*; an miRNA inhibitor capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*. In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12. In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence. In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*). In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

Various embodiments of the present invention also provide for a system for detecting a disease state of a cancer in a subject, comprising: a biological sample from a subject; detection probes to test the biological sample for a relative increase, decrease, or steady expression of DLK1-DIO3 cluster/region. In various embodiments, the system further comprises a machine (e.g., computer) to associate a relative increased expression the DLK1-DIO3 cluster/region with metastatic disease state or associate a relative decreased or a steady expression level of DLK1-DIO3 cluster/region with a non-metastatic disease state.

In certain embodiments, the metastatic disease state is bone metastasis. In certain embodiments, the cancer is metastatic prostate cancer. In certain embodiments, the cancer is metastatic lung cancer. In certain embodiments, the cancer is metastatic breast cancer.

Various embodiments of the present invention provide for a system for predicting responsiveness to a cancer drug, comprising: a biological sample from a subject; detection probes to test the biological sample for a relative increase, decrease, or steady expression of MEG9. In various embodiments, the system further comprises a machine (e.g., computer) to associate a relative increased expression level of MEG9 with a lower likelihood of drug responsiveness or associate a relative decreased or a steady expression level of MEG9 with a higher likelihood of drug responsiveness.

In various embodiments, the cancer drug is a tyrosine kinase inhibitor (TKI). In certain embodiments, the TKI is an EGFR-TKI. In particular embodiments, the EGFR-TKI is Erlotinib (TARCEVA). In particular embodiments, the TKI is Gefitinib. In certain embodiments, the TKI is Apatinib, Cabozantinib, Canertinib, Crenolanib, Damnacanthal, Foretinib, Fostamatinib, Intedanib, Linifanib, Motesanib, Mubritinib, Vatalanib, or Vemurafenib.

In other embodiments, the cancer drug is an miRNA inhibitor. In various embodiments, the miRNA inhibitor is capable of inhibiting miR-379, miR-379*, miR-193b, miR-193b*, miR-409-5p, miR-409-3p, miR-154, and/or miR-154*; an miRNA inhibitor capable of inhibiting mature miR-379, miR-379*, miR-193b, miR-193b*, miR-409-5p, miR-409-3p, miR-154, and/or miR-154*. In particular embodiments, the miRNA inhibitor is capable of inhibiting mature miR-379, miR-193b, miR-409-5p, miR-409-3p or miR-154*. In certain embodiments, the miRNA inhibitor is a shRNA or a siRNA capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a shRNA or a siRNA capable of interfering the expression of SEQ ID NO:2, SEQ ID NO:5, SEQ ID NO: 8, SEQ ID NO:9, or SEQ ID NO:12. In certain embodiments, the miRNA inhibitor is a short hairpin RNA (shRNA) directed against mature miRNAs. In certain embodiments, the shRNA is encoded by a polynucleotide as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24. A composition comprising a polynucleotide comprising or as disclosed by SEQ ID NO:1, SEQ ID NO:4, SEQ ID NO:7, SEQ ID NO:10, SEQ ID NO: 20, SEQ ID NO:21, SEQ ID NO:23 or SEQ ID NO:24, for example, as a plasmid, can be administered to the subject. Thereafter, the shRNA is expressed in vivo after the administration of the polynucleotide, and inhibits its target miRNA sequence. In certain embodiments, the miRNA inhibitor is a siRNA directed against mature miRNAs. In various embodiments, the siRNA is as disclosed by SEQ ID NO:3 (to target and inhibit miRNA379), SEQ ID NO:6 (to target and inhibit miRNA193b), or SEQ ID NO:11 (to target and inhibit miRNA154*). In various embodiments, the miRNA inhibitor is a morpholino antisense oligonucleotide capable of interfering with the expression of SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA inhibitor is a morpholino antisense oligonucleotide capable of interfering with the expression of SEQ ID NO:2, SEQ ID NO:5, SEQ ID NO: 8, SEQ ID NO:9, or SEQ ID NO:12. In various embodiments, the morpholino antisense oligonucleotide is as disclosed by SEQ ID NO:13, SEQ ID NO: 14, or SEQ ID NO: 15.

In certain embodiments, the cancer is prostate cancer. In certain embodiments, the cancer is lung cancer. In certain embodiments, the cancer is breast cancer. In certain embodiments, the cancer is metastatic cancer. In certain embodiments, the metastatic cancer is metastasis to the bone. In certain embodiments, the cancer is metastatic prostate cancer. In certain embodiments, the cancer is metastatic lung cancer. In certain embodiments, the cancer is metastatic breast cancer.

Various embodiments of the present invention also provide for a system for detecting a disease state of a cancer in a subject, comprising: a biological sample from a subject; detection probes to test the biological sample for a relative increase, decrease, or steady expression of MEG9. In various embodiments, the system further comprises a machine (e.g., computer) to associate a relative increased expression the MEG9 with metastatic disease state or associate a relative decreased or a steady expression level of MEG9 with a non-metastatic disease state.

In certain embodiments, the metastatic disease state is bone metastasis. In certain embodiments, the cancer is metastatic prostate cancer. In certain embodiments, the cancer is metastatic lung cancer. In certain embodiments, the cancer is metastatic breast cancer.

With respect to methods and systems of the present invention, the relative increase, decrease or steady expression of the miRNA, DLK1-miRNA, DLK1-DIO3 cluster/region, or MEG9 is relative to a control (e.g., established control, non-cancerous biological sample, non-cancerous biological sample of the same type (e.g., non-cancerous lung tissue as the control vs. cancerous lung tissue as the biological tested)).

The subjects with respect to the methods and systems of the present invention are subject who have cancer, are suspected of having cancer, are diagnosed with cancer, or suffering from cancer. Examples of cancers are described herein.

Examples of biological sample with respect to methods and systems of the present invention include, but are not limited to mammalian body fluids, sera such as blood (including whole blood as well as its plasma and serum), CSF (spinal fluid), urine, sweat, saliva, tears, pulmonary secretions, breast aspirate, prostate fluid, seminal fluid, stool, cervical scraping, cysts, amniotic fluid, intraocular fluid, mucous, moisture in breath, animal tissue, cell lysates, tumor tissue, hair, skin, buccal scrapings, nails, bone marrow, cartilage, prions, bone powder, ear wax, etc. or even from external or archived sources such as tumor samples (i.e., fresh, frozen or paraffin-embedded).

Examples of detection probes used in the systems or methods of the present invention include nucleic acids, antibodies, a substrate that reacts with the miRNA, DLK1-miRNA, DLK1-DIO3 cluster/region, or MEG9. In various embodiments, the detection probe comprises a label to produce a signal so as to detect the relative increase, decrease or steady expression of the miRNA, DLK1-miRNA, DLK1-DIO3 cluster/region, or MEG9. In various embodiments, the detection probe is in a chip, microarray or gel.

Drug Screening

Various embodiments of the present invention provide for a method of screening for inhibitors or agonists of a miRNA, comprising; providing a test compound; contacting the test compound with a cell expressing the miRNA; detecting a relative increase, decrease, or steady expression of the miRNA; and identifying the test compound as an inhibitor when a relative decrease of the miRNA expression is detected, identifying the test compound as an agonist when a relative increase of the miRNA expression is detected.

In various embodiments, the miRNA is miR-379, miR-379*, miR-193b, miR-193b*, miR-409-5p, miR-409-3p, miR-154, and/or miR-154*. In various embodiments, the miRNA is mature miR-379, miR-379*, miR-193b, miR-193b*, miR-409-5p, miR-409-3p, miR-154, and/or miR-154*. In particular embodiments, the miRNA is mature miR-379, miR-193b, miR-409-5p, miR-409-3p and/or miR-154*. In various embodiments, the miRNA has a sequence as disclosed by SEQ ID NO:2, SEQ ID NO:3, SEQ ID NO:5, SEQ ID NO:6, SEQ ID NO:8, SEQ ID NO:9, SEQ ID NO: 11 or SEQ ID NO:12. In particular embodiments, the miRNA has a sequence as disclosed by SEQ ID NO:2, SEQ ID NO:5, SEQ ID NO: 8, SEQ ID NO:9, or SEQ ID NO:12.

Various embodiments of the present invention provide for a method of screening for inhibitors or agonists of the DLK1-DIO3 region, comprising; providing a test compound; contacting the test compound with a cell expressing the DLK1-DIO3 region; detecting a relative increase, decrease, or steady expression of the DLK1-DIO3 region; and identifying the test compound as an inhibitor when a relative decrease of the DLK1-DIO3 region expression is detected, identifying the test compound as an agonist when a relative increase of the DLK1-DIO3 region expression is detected.

Various embodiments of the present invention provide for a method of screening for inhibitors or agonists of MEG9, comprising; providing a test compound; contacting the test compound with a cell expressing MEG9; detecting a relative increase, decrease, or steady expression of MEG9; and identifying the test compound as an inhibitor when a relative decrease of MEG9 expression is detected, identifying the test compound as an agonist when a relative increase of MEG9 expression is detected.

The present invention is also directed to kits for practicing various embodiments of the invention. The kit is an assemblage of materials or components, including at least one of the inventive compositions. Thus, in some embodiments the kit contains a composition including miRNA inhibitors as described above. In other embodiments, the kit contains a composition including probes for use in various diagnostic, prognostic, prediction, and/or detection methods and systems.

The exact nature of the components configured in the inventive kit depends on its intended purpose. For example, some embodiments are configured for the purpose of treating cancer. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to inhibit cancer metastasis. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing miRNA inhibitors. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1—Sequences

TABLE 1A

| miRNA or inhibitor | Sequence (5'- 3') | SEQ ID NO. |
|---|---|---|
| miRZIP379 | GGATCC GTGGTAGATTATGGAACATAAGCTTCCTGTC AGCCTACGTTCCATAGTCTACCATTTTT GAATTC | 1 |
| miR379 mature | ugguagacuauggaacguagg | 2 |
| miR379* mature | uauguaacaugguccacuaacu | 3 |

TABLE 1A-continued

| miRNA or inhibitor | Sequence (5'- 3') | SEQ ID NO. |
| --- | --- | --- |
| miRZIP193b | GGATCC GAACTGGCACTCAAAGTCACGATCTTCCTGT CAGAGCGGGACTTTGAGGGCCAGTTTTTT GAATTC | 4 |
| miR193b-mature | aacuggcccucaaagucccgcu | 5 |
| miR193b*-mature | cgggguuuugagggcgagauga | 6 |
| miRZIP409-5p | GGATCC GAGGTTACCaGAGCAACTTTGCACTTCCTGTC AGTGCAAAGTTGCTCGGGTAACCTTTTTT Gaattc | 7 |
| miR409-5p mature | AGGUUACCCGAGCAACUUUGCAU | 8 |
| miR409-3p-mature | GAAUGUUGCUCGGUGAACCCC U | 9 |
| miRZIP154 | GGATCC GTAGGTTACCCGTGTTGCATTAGCTTCCTGTC AGCGAAGGCAACACGGATAACCTATTTTT GAATTC | 10 |
| miR154 mature seq | uagguuauccguguugccuucg | 11 |
| miR154* mature | aaucauacacgguugaccuauu | 12 | miRZIP refers to DNA encoding microRNA inhibitors (short hairpin RNAs directed against mature microRNAs) which cause cell death of prostate cancer cells
mature refers to the mature microRNA sequence and cause cancer
*refers to the complementary microRNA sequence
All miRZIPs are custom made
All mature microRNA constructs are purchased from System Biosciences

TABLE 1B

| miRNA or inhibitor | Sequence (5'-3') | SEQ ID NO. |
| --- | --- | --- |
| 379 mature | TGGTAGACTATGGAACGTAGG | 16 |
| 193b mature | aactggccctcaaagtcccgct | 17 |
| 409-5p mature | A GGT TAC CCG AGC AAC TTT GCA T | 18 |
| 154* mature | aatcatacacggttgacctatt | 19 |
| miRZIP154* | gat ccg AAT CAT ACA CaG TTG ACC TcT TCT TCC TGT CAG AAT AGG TCA ACC GTG TAT GAT TTT TTT G (68) | 20 |
|  | AAT TCA AAAAAATCATACACGGTTGACCTATTCTGAC AGGAAGAAgAGGTCAACtGTGTATGATTcg | 21 |
| 409-3p mature | GAA TGT TGC TCG GTG AAC CCC T | 22 |
|  | ga tcc g GAA TGT TGC TCa GTG AAC CtC TCT TCC TGT CAG AGG GGT TCA CCG AGC AAC ATT C TT TTT G | 23 |
| miRZIP409-3p | AAT TCA AAA AGA ATG TTG CTC GGT GAA C CC CTC TGA CAG GAA GAG aGG TTC ACt GAG CAA CAT TCc g | 24 | miRZIP refers to DNA encoding microRNA inhibitors
mature refers to the mature microRNA sequence
*refers to the complementary microRNA sequence

Example 2

A prostatic bone growth model was established by intratibial injection of 1×10⁶ ARCaPM bone metastatic prostate cancer cells suspended in PBS into both legs of male Nu/Nu nude mice. A week after injection, the mice were treated with vehicle (n=5) or Vivo Morpholinos (12.5 mg/kg or 25 nmole per injection) (n=5) alternate days for two weeks. The mode of injection of Morpholinos is intravenous route in the tail vein of mice. Tumor progression was measured using X-ray imaging of bone lesions. Mice were humanely sacrificed on Day 30 and bones were harvested for histopathology.

Targeting microRNAs, for example, miR-409-5p, using Vivo-Morpholinos is expected to reduce bone lesions in mice compared to mice that had been injected with the vehicle (both by X-ray imaging and histopathology studies).

TABLE 2

| Morpholino antisense target | Morpholino antisense sequence | SEQ ID NO. |
|---|---|---|
| miR379 mature | 5'CGCCTACGTTCCATAGTCTACCATC 3' | 13 |
| miR409-5p mature | 5'GGGTTCACCGAGCAACATTCGTCGT 3' | 14 |
| miR154* mature | 5'AGCGAAGGCAACACGGATAACCTAT 3' | 15 |

Example 3—Materials and Methods

Cell Culture

Human androgen-refractory PCa ARCaPE and ARCaPM and LNCaP, LNCaPNeo and LNCaPRANKL PCa (Xu et al., Prostate cancer metastasis: role of the host microenvironment in promoting epithelial to mesenchymal transition and increased bone and adrenal gland metastasis. Prostate 2006; 66: 1664-73; Hu et al. Multiplexed quantum dot labeling of activated c-Met signaling in castration-resistant human prostate cancer. PLoS One 2011; 6: e28670; Chu et al. RANK- and c-Met-mediated signal network promotes prostate cancer metastatic colonization. Endocr Relat Cancer 2014; 21: 311-26) were used. PCa cells and 293T cells were cultured in T-medium (GibcoBRL) supplemented with 5% heat inactivated fetal bovine serum (Bio-Whittaker).

All cells were tested for *mycoplasma* every three months and were negative. The embryonic stem cells and iPSCs derived small RNA preparations were provided by Drs. Sareen and Svendsen.

miRNA Expression

Quantitative Real Time PCR (qRT-PCR):

miRNA expression analysis by qRT-PCR was performed separately for each miRNA using specific primer sets (Applied Biosystems). RNU6B was used for normalization.

mRNA Analysis:

Total RNA was isolated using the RNeasy Mini Kit (Qiagen). cDNA was made using Superscript III reverse transcriptase (Life Technologies). mRNA primers were designed and synthesized at Integrated DNA Technologies. mRNA expression levels were determined by qRT-PCR assays and SYBR Green Dye (Applied Biosystems).

Long Noncoding RNA Analysis mRNA was extracted as described above. LncRNA expression levels were determined as per manufacturer's instruction (System Biosciences) using real-time PCR. Relative levels of MEG9 were plotted normalized to GAPDH.

Cytoscape Analysis

Cytoscape image was created using miR-409-5p and miR-409-3p target genes from Targetscan v12 software analysis and Genecard website (STRING: functional protein association networks).

In Situ Hybridization (ISH)-Quantum Dots (QD)

Human Gleason Tissue Array:

A Gleason score tissue array was obtained from Vancouver Prostate Center. The use of specimens in research was approved by the institution review board of the Cedars-Sinai Medical Center (IRB# Pro21228). The tissues consisted of benign prostatic hyperplasia (BPH) (N=14), Gleason 6 (N=26) and Gleason ≥7 (N=35). Each tissue had two cores in the array. These patients had no treatment. The tissue array was stained for H&E and graded by a pathologist. Information on Gleason score of the cancer and miR-409 intensity is included in Table 3. The control scramble and miR-409-5p and -3p probes were 5'-biotin labeled. The probes were linked to streptavidin-conjugated QD. Multiplex QD labeling (mQDL) was performed. miR-409-5p was labelled with 625 nm QD (red) followed by miR-409-3p (green) which was labeled with 565 nm QD. The QD fluorescence intensity of each tissue section was determined and analyzed. Statistical analysis was performed on the data set using a Kruskal-Wallis one way analysis of variance and post hoc Tukey method for multiple comparisons between groups. Data distribution was depicted as box plots.

TABLE 3

Gleason scores of the cancer from which the TMA cores were obtained and the miR-409 intensity counts by ISH-QD. None of the TMA cores had any treatment.

| worksheet | super group | Gleason score | intensity |
|---|---|---|---|
| Tumor-3p | BPH | BPH | 0.085 |
| Tumor-3p | BPH | BPH | 0.087 |
| Tumor-3p | BPH | BPH | 0 |
| Tumor-3p | BPH | BPH | 0.018 |
| Tumor-3p | BPH | BPH | 0.077 |
| Tumor-3p | BPH | BPH | 0.005 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | BPH | BPH | 0 |
| Tumor-3p | Gleason 6 | Gleason 6 | 0 |
| Tumor-3p | Gleason 6 | Gleason 6 | 0.217 |
| Tumor-3p | Gleason 6 | Gleason 6 | 0.111 |
| Tumor-3p | Gleason 6 | Gleason 6 | 0.008 |
| Tumor-3p | Gleason 6 | Gleason 6 | 0.016 |
| Tumor-3p | Gleason 6 | Gleason 6 | 0.228 |
| Tumor-3p | Gleason 6 | Gleason 6 | 0.131 |
| Tumor-3p | Gleason 6 | Gleason 6 | 0 |

TABLE 3-continued

Gleason scores of the cancer from which the TMA cores were obtained and the miR-409 intensity counts by ISH-QD. None of the TMA cores had any treatment.

| worksheet | super group | Gleason score | intensity |
|---|---|---|---|
| Tumor-3p | Gleason 6 | Gleason 6 | 0.045 |
| Tumor-3p | Gleason 6 | Gleason 6 | 0.084 |
| Tumor-3p | Gleason 6 | Gleason 6 | 0.074 |
| Tumor-3p | Gleason 6 | Gleason 6 | 0.039 |
| Tumor-3p | Gleason 6 | Gleason 6 | 0.164 |
| Tumor-3p | Gleason 6 | Gleason 6 | 0.151 |
| Tumor-3p | Gleason 6 | Gleason 6 | 0.13 |
| Tumor-3p | Gleason 6 | Gleason 6 | 0 |
| Tumor-3p | Gleason 6 | Gleason 6 | 0 |
| Tumor-3p | Gleason 6 | Gleason 6 | 0 |
| Tumor-3p | Gleason 6 | Gleason 6 | 0 |
| Tumor-3p | Gleason 6 | Gleason 6 | 0 |
| Tumor-3p | Gleason 6 | Gleason 6 | 0 |
| Tumor-3p | Gleason 6 | Gleason 6 | 0 |
| Tumor-3p | Gleason 6 | Gleason 6 | 0 |
| Tumor-3p | Gleason 6 | Gleason 6 | 0 |
| Tumor-3p | Gleason 6 | Gleason 6 | 0 |

In Vivo Animal Studies:

Mouse tumor and tumor xenografts were formalin-fixed and paraffin-embedded. miRNA ISH protocol was followed as per manufacturer's instruction (Exiqon, MA). Single QD labeling was performed. Scramble, miR-409-5p or miR-409-3p probes were labeled with 625 nm QDs. Images were taken at 40×. H&E staining was performed on subsequent tissue sections.

MSKCC Dataset Analysis

The dataset was published by MSKCC team (Taylor et al., Integrative genomic profiling of human prostate cancer. Cancer cell 2010; 18: 11-22) and was obtained from cBio-Portal (Gao, et al. Integrative analysis of complex cancer genomics and clinical profiles using the cBioPortal. Science signaling 2013; 6: p 11). miR-409-3p but not miR-409-5p was analyzed in the dataset. For the analysis of miR-409-3p with different Gleason scores, patients with Gleason score 6 or 7 (n=86) were grouped together to compare with those with Gleason score 8 or 9 (n=12). Student t test was done between the two groups for analysis of differential expression of miR-409-3p between two cohorts. For the survival analysis, the expression levels of miR-409-3p in patients were compared with the median expression level of normal individuals. The disease free survival of patients with miR-409-3p expression levels higher than normal individual (n=29) was compared with that with lower miR-409-3p expression levels (n=78). Kaplan-Meier survival curve was done by log-rank test between high and low expression groups.

Lentiviral Transduction

ARCaPE or LNCaP PCa cell lines were transduced with miR-409 lentivirus expressing green fluorescent protein (GFP) or control GFP lentivirus and ARCaPM PCa cell lines were transduced with miR-409-5p lentivirus expressing GFP or control GFP lentivirus. Lentiviral preparation and transduction of cell lines were performed as per the manufacturer's instructions (System Biosciences). GFP positive cells were FACS sorted and cultured in vitro.

Growth Assay, Invasion and Migration Assays

ARCaPM-C and ARCaPM-409-5pi cells were grown and counted for a week.

Cell viability assay was performed using MTS assay. Cancer cell invasion and migration were assayed in Companion 24-well plates (Becton Dickinson Labware).

Western Analysis

Western analysis was performed. The membranes were incubated with mouse monoclonal antibody against STAG2 (Cell Signaling technology), RSU1 (Proteintech Group), β-actin (Sigma-Aldrich) respectively, at 4° C. overnight.

Xenograft Studies

All animal experiments were IACUC approved and done in accordance with institutional guidelines.

Orthotopic Study:

Preparation of grafts: 293T cells were transduced with either miR-409 expressing lentiviral vector carrying GFP or control vector carrying a GFP plasmid (System Biosciences) viral particles. 293T cells were incubated for 24 h and the cells were trypsinized. Cell grafts were made by mixing 3 parts of rat tail collagen and 1.2 parts of setting solution. The mixture was added to the 293T cells. The mixture ($6\times10^5$ 293 T cells) was orthotopically injected into four-week-old male nude mice (NCRNU, Taconic) prostates (N=5/group). The control or miR-409 GFP plasmids were expected to be released from the 293T cells and enter the adjacent epithelium and stroma of the mouse prostate. The 293T cells were lysed when the viruses were released. Mice were monitored for miR-409 expression by detecting GFP fluorescence and for tumor growth using NIR dye (IR783) (Yang, et al. Near IR heptamethine cyanine dye-mediated cancer imaging. Clin Cancer Res 2010; 16: 2833-44) using IVIS® Lumina Imaging system. Tumors developed from 2-6 months in the miR-409 group. Mice were euthanized and tumors sections were stained for specific markers.

Immunohistochemistry (IHC)

IHC staining was performed. The following primary antibodies were used: Ki-67 (Abcam), STAG2, p-AKT (Cell Signaling technologies), RSU1 (Proteintech Group), Vimentin (V9), Nanog, Oct-3/4, cytokeratin 5 (Santa Cruz Biotechnology), cytokeratin 8 (Covance, Inc.) were used.

In Vivo Metastasis Study:

Luciferase tagged ARCaPM control and ARCaPM-409-5pi cells were injected intracardially in male SCID/beige mice (Charles River Laboratories) (N=5/group). Mice were imaged for bioluminescence and X-ray detection using IVIS® Lumina Imaging system. Mice were euthanized when they produced large tumors. Mice were given NIR dye (IR783) 48 h before euthanasia, the tumor specific NIR dye was used to detect metastatic tumor in the mice.

Statistical Analysis

Values were expressed as means±standard deviation. All experiments were done in triplicates at least two independent times. Statistical analysis was performed using Student's t-test. For tissue Gleason score array, the difference between the groups were tested by Kruskal-Wallis one way analysis of variance. A post hoc Tukey method was used to enable multiple comparisons between groups. Values of $p<0.05$ were considered to be statistically significant.

miRNA Global Profiling Real Time PCR Multiplexing

Profiling was performed for $ARCaP_E$ and $ARCaP_M$ PCa cells. miRNA analysis was performed. Each sample was run in duplicates. Three hundred and thirty miRNAs were tested (Ct values). The raw data was analyzed for significant fold changes. The miRNA with the highest fold changes are depicted on Table 4 which were statistically significant ($p<0.05$, t test).

Generation of Non-Integrating Human iPSCs Using Episomal Plasmids

Apparently healthy human fibroblast cell lines (GM05400, 03814 and 02183) were obtained from the Coriell Institute for Medical Research, under their consent and privacy guidelines. All protocols were performed in accordance with the institutional review board's guidelines at the Cedars-Sinai Medical Center under the auspice IRB-SCRO Protocols, Pro00021505 and Pro00032834. Limbal epithelial stem cell-enriched cultures were prepared from discarded donor corneoscleral rims (01CNL) provided by Drs. Rabinowitz and Maguen within 24 hrs after corneal transplantation, under an approved Cedars-Sinai Medical Center IRB protocol Pro00019393. Cells were isolated by the standard dispase method. Upon iPSC generation at Cedars Sinai, they were renamed 00iCTR-n2, 14iCTR-n6, 83iCTR-n1, and 01iCNL-n1 to reflect catalog or identification numbers, control line and clone number. Fibroblasts or limbal cells were reprogrammed into virus-free iPSC lines using the Amaxa Human Dermal Fibroblast Nucleofector Kit to express episomal plasmids with 6 factors: OCT4, SOX2, KLF4, L-MYC, LIN28, and p53 shRNA (Addgene). This method has a significant advantage over viral transduction, because exogenously introduced genes do not integrate and are instead expressed episomally in a transient fashion. Briefly, fibroblasts ($0.8 \times 10^6$ cells per nucleofection) were harvested, centrifuged at 200 g for 5 minutes, re-suspended carefully in Nucleofector® Solution (VPD-1001, Lonza) and the U-023 program was applied. All cultures were maintained under norm-oxygen conditions (5% $O_2$) during reprogramming, which further enhance the efficiency of iPSC generation. The media was kept on for 48 hours and gradually changed to chemically-defined mTeSR®1 medium containing small molecules to enhance reprogramming efficiency. The small molecules used were, (1) sodium butyrate (0.5 mM; Sigma-Aldrich), (2) glycogen synthase kinase 3β inhibitor of the Wnt/β-catenin signaling pathway (CHIR99021, 3 μM; Tocris Bioscience/R&D Systems, Minneapolis, Minn.), (3) MEK pathway inhibitor (PD 0325901, 0.5 μM; (Stemgent, Cambridge, Mass.), (4) Selective inhibitor of TGF-13 type I receptor ALK5 kinase, type I activin/ nodal receptor ALK4 and type I nodal receptor ALK7 (A 83-01, 0.5 μM; (Tocris Bioscience). Colonies with ES/iPSC-like morphology appeared 25-31 days later. Subsequently, colonies with the best morphology were transferred onto a feeder-independent BD Matrigel™ Matrix and maintained in mTeSR®1 medium.

Human Embryonic Stem Cell (ESC) and iPSC Cell Culture

Human ESC line, H9 (WiCell, Madison, Wis.) and iPSC lines were maintained onto a feeder-independent BD Matrigel™ Matrix and maintained in mTeSR®1 medium. Colonies grown on growth factor-reduced Matrigel (BD Biosciences, San Jose, Calif.) had typical ESC-like morphology with well-defined borders, and high nuclear/cytoplasmic ratio. The iPSC clones were further expanded and cryopreserved according to previously published protocols.

Human iPSC Characterization

Human iPSCs were rigorously characterized at the Cedars-Sinai iPSC core using several assays. G-Band karyotyping (see below) ensured normal a karyotype, and genomic DNA PCR confirmed the absence of episomal plasmid genes. Pluripotency was assessed by immunostaining with surface and nuclear pluripotency markers for subsequent flow cytometry quantification (>80% SSEA4 and Oct3/4 double positivity), by quantitative RT-PCR of endogenous pluripotency genes, and by gene-chip and bioinformatics-based PluriTest assays. Spontaneous embryoid body differentiation confirmed the capacity to form all germ layers. Characterization of iPSC lines used in this study has been previously published (Sareen et al., Inhibition of apoptosis blocks human motor neuron cell death in a stem cell model of spinal muscular atrophy. PLoS One 2012; 7: e39113; Sareen et al., Targeting RNA foci in iPSC-derived motor neurons from ALS patients with a C9ORF72 repeat expansion. Sci Transl Med 2013; 5: 208ra149).

3'UTR Assay 293T cells were stably transduced with Lenti Goclone lentivirus particles containing a constitutive promoter driving a hybrid luciferase-3' UTR of human STAG2 transcript (MISSION® 3'UTR Lenti GoClone™, Sigma-Aldrich). Cells were selected using puromycin. Mimics of miR-409-5p, miR-409-3p and control miRNA were transiently transfected into these 293T cells and luciferase activity was determined using Lightswitch luciferase assay system (Switchgear genomics).

RSU1 mutant luciferase activity: 3'UTR construct (Switchgear genomics) was used as the wild type (WT) luciferase construct and it was further mutated as described below. miR-409-5p mimic and control miRNA were transiently transfected along with the WT or mutant (RSU1) construct into these 293T cells and luciferase activity was determined 24 h later using Lightswitch luciferase assay system (Switchgear genomics).

3'UTR Mutant Constructs:

Mutated 3' UTR luciferase constructs were produced by sited-directed mutagenesis. Briefly, primer pairs with two sequential base pair mutations in the miRNA seed sequence of the 3' UTR were generated. Following polymerase chain reaction amplification, parental methylated template DNA was digested for 1 hour with Dpn I. 2 μl of the reaction was then transformed into XL-10 Gold bacteria. 16 hours post-transformation, colonies were picked for liquid culture. Plasmid DNA was isolated by the Zyppy Plasmid Miniprep Kit according to manufacturer's directions (Zymo Research). Mutations were confirmed by sequencing before proceeding with luciferase assays.

Primers

```
miR-409-5p RSU 1
                                            (SEQ ID NO: 25)
Gttaacagtgacatttaaatggggacatgattttaattattcttttgata ataagcaaccttg miR-409-5p RSU 2
                                            (SEQ ID NO: 26)
Caaggttgcttattatcaaaagaataattaaaatcatgtccccatttaaa tgtcactgttaac
```

Antibodies Used for IHC and Western Analysis

Antigen retrieval was used for IHC.

|  | Secondary | Dilution | Company | Catalog | Reactivity |
|---|---|---|---|---|---|
| NANOG | mouse | 1:50 | Santa Cruz Biotechnology | sc-134218 | h, m |
| OCT3/4 | mouse | 1:50 | Santa Cruz Biotechnology | sc-5279 | h, m |
| CK8 | mouse | 1::200 | Covance, Inc | MMS-162P | h, m |
| CK5 | rabbit | 1::200 | Covance, Inc | PRB-106p | h, m |
| p-Akt | rabbit | 1:50 | Cell Signaling | 4060S | h, m |
| Ki-67 | rabbit | 1:100 | Abcam | ab16667 | h, m |
| STAG2 | rabbit | 1::200 | Cell Signaling technologies | 5882 | h, m |
| RSU1 | rabbit | 1::200 | Proteintech group | 11207-1-AP | h, m |
| VIM | mouse | 1:200 | Santa Cruz Biotechnology | sc-6260 | h, m |
| E-cadherin | rabbit | 1:500 | Cell signaling | 3195 | H, m | miRNA Determination from Exosomes

Cancer cells were maintained in T-medium with exosome depleted FBS media supplement (System Biosciences) for 48 h and conditioned media was used to extract exosomes. Exo-Quick-TC (System Biosciences) for tissue culture Media, and SeraMir exosome RNA purification kit (System Biosciences) was used to extract miRNA from exosomes. MiRNA were detected for miR-409-5p/-3p by qRT-PCR analysis.

Example 4—Results

MicroRNA miR-409-3p/-5p is Overexpressed in Bone Metastatic EMT Models of Human PCa To understand the regulatory role of microRNAs in EMT and PCa bone metastasis, we performed miRNA profiling of two lineage-related, differentially bone metastatic human PCa cell lines, ARCaPE (non-metastatic line) and ARCaPM (metastatic line), denoted respectively their epithelial (AR-CaPE) and mesenchymal (ARCaPM) phenotype (Tables 4 and 5). The differential miRNA expression of the nonmetastatic (ARCaPE) and metastatic PCa cells (ARCaPM) are represented in Table 5. We observed markedly upregulated miR-409-3p/-5p expression in the bone metastatic ARCaPM variant (FIG. 1A). miR-409-3p and -5p miRNAs were in the top five of the differentially expressed miRNAs between ARCaPM and ARCaPE PCa cells. We observed a similar increases in miR-409-5p/-3p expression in the LNCaPNeo verses LNCaPRANKL bone metastasis PCa model (FIG. 1A). Thus, in two different PCa bone metastatic EMT models, we observed an increase in miR-409-5p/-3p. miR-409-3p and -5p are generated from an immature transcript and transcribed from the 5' end of the pre-miRNA. miR-409 is located in a region that overlaps the long non-coding RNA MEG9. The expression levels of MEG9 lncRNAs hence were elevated in the metastatic ARCaPM PCa cells compared to non-metastatic ARCaPE PCa cells (FIG. 1B). In addition to bone metastatic human PCa cells, human embryonic stem cells and induced pluripotent cells also notably expressed elevated levels of miR-409-3p/-5p (FIG. 1C, 1D). Thus, we demonstrate that miR-409-3p/-5p is upregulated in two aggressive, bone metastatic EMT PCa models and in human embryonic stem cells and iPSCs.

TABLE 4

Global miRNA expression, represented as Ct values assayed by multiplexed qRT-PCR analysis in $ARCaP_E$ and $ARCaP_M$ PCa EMT bone metastatic model.

| microRNA names | Ct values $ARCaP_E$ | Ct values $ARCaP_M$ | microRNA names | Ct values $ARCaP_E$ | Ct values $ARCaP_M$ |
|---|---|---|---|---|---|
| h-miR-517* | 23.38 | 40 | hmr-miR-101 | 39.99 | 40 |
| h-miR-516-5p | 24.45 | 40 | hm-miR-9* | 40 | 40 |
| h-miR-512-5p | 25.29 | 40 | h-miR-511 | 40 | 40 |
| h-miR-346 | 25.33 | 40 | hmr-miR-130a | 40 | 40 |
| h-miR-514 | 26.02 | 40 | hr-miR-204 | 40 | 40 |
| h-miR-224 | 21.9 | 40 | hmr-miR-219 | 40 | 40 |
| h-miR-513 | 20.97 | 40 | h-miR-330 | 31.35 | 40 |
| h-miR-488 | 20.78 | 40 | h-miR-217 | 30.45 | 40 |
| h-miR-326 | 23.45 | 37.63 | hmr-miR-213 | 31.18 | 37.73 |
| h-miR-515-3p | 29.11 | 40 | h-miR-507 | 33.89 | 40 |
| h-miR-451 | 30.72 | 40 | hmr-miR-33 | 33.5 | 40 |
| h-miR-34b | 25.68 | 40 | h-miR-495 | 34.47 | 40 |
| h-miR-512-3p | 27.3 | 40 | h-miR-432* | 32.51 | 40 |
| h-miR-302b | 27.63 | 40 | h-miR-211 | 32.86 | 40 |
| h-miR-215 | 27.75 | 40 | h-miR-363 | 32.15 | 40 |
| h-miR-506 | 28.13 | 40 | h-miR-129 | 33.88 | 40 |
| h-miR-510 | 27.24 | 40 | h-miR-UL22A-1 | 34.73 | 40 |
| h-miR-202* | 26.81 | 40 | hmr-miR-299-5p | 35.5 | 32.64 |
| h-miR-516-3p | 29.06 | 40 | hmr-miR-128a | 36.26 | 33.3 |
| h-miR-492 | 29.16 | 40 | hr-miR-134 | 37.49 | 31.13 |
| h-miR-337 | 29.57 | 40 | h-miR-379 | 40 | 32.5 |
| h-miR-508 | 28.6 | 40 | h-miR-154* | 40 | 32.34 |
| h-miR-302c | 28.64 | 40 | h-miR-487 | 40 | 32.94 |
| h-miR-302a* | 32.51 | 28.74 | h-miR-519a | 40 | 33.94 |
| hm-miR-1 | 31.78 | 30.14 | h-miR-409-3p | 40 | 23.65 |
| hm-miR-133b | 29.92 | 28.28 | h-miR-367 | 40 | 30.31 |
| h-miR-485-3p | 30.67 | 34.04 | hmr-miR-296 | 40 | 40 |
| h-miR-299-3p | 31.22 | 33.68 | hmr-miR-141 | 36.42 | 40 |
| hr-miR-137 | 33.04 | 33.88 | h-miR-497 | 40 | 36.5 |
| h-miR-483 | 24.6 | 29.55 | hr-miR-187 | 40 | 40 |
| h-miR-10b | 28.26 | 31.06 | h-miR-429 | 40 | 40 |
| h-miR-329 | 24.23 | 33.61 | h-miR-452* | 40 | 40 |
| h-miR-489 | 25.9 | 26.91 | h-miR-504 | 40 | 40 |
| hmr-miR-133a | 26.92 | 25.53 | h-miR-373 | 40 | 40 |
| hmr-miR-135b | 22.83 | 23.29 | hm-miR-148a | 40 | 40 |
| h-miR-155 | 27.08 | 24.76 | h-miR-422a | 40 | 29.74 |
| h-miR-31 | 17.82 | 24.44 | hmr-miR-185 | 40 | 31.4 |
| hmr-miR-146a | 21.65 | 19.08 | hmr-miR-214 | 37.38 | 32.89 |
| h-miR-517c | 40 | 40 | h-miR-455 | 40 | 29.9 |
| h-miR-520a* | 40 | 40 | h-miR-424 | 40 | 29.48 |
| hmr-miR-128b | 40 | 40 | h-miR-502 | 40 | 31.35 |
| hmr-miR-122a | 40 | 40 | h-miR-517b | 40 | 34.47 |
| hmr-miR-136 | 40 | 40 | h-miR-374 | 40 | 35.14 |
| hmr-miR-138 | 40 | 40 | hmr-miR-184 | 40 | 32.96 |

TABLE 4-continued

Global miRNA expression, represented as Ct values assayed by multiplexed qRT-PCR analysis in ARCaP$_E$ and ARCaP$_M$ PCa EMT bone metastatic model.

| microRNA names | Ct values ARCaP$_E$ | Ct values ARCaP$_M$ | microRNA names | Ct values ARCaP$_E$ | Ct values ARCaP$_M$ |
|---|---|---|---|---|---|
| hmr-miR-142-5p | 40 | 40 | h-miR-96 | 31.13 | 33.19 |
| hmr-miR-143 | 40 | 40 | h-miR-199b | 31.84 | 34.36 |
| hmr-miR-144 | 40 | 40 | hmr-miR-32 | 32.57 | 32.9 |
| hmr-miR-145 | 40 | 40 | hmr-miR-205 | 32.86 | 31.82 |
| hmr-miR-154 | 40 | 40 | h-miR-520f | 33.04 | 34.83 |
| hmr-miR-190 | 40 | 40 | hmr-miR-223 | 34.46 | 34.59 |
| hmr-miR-199a | 40 | 40 | h-miR-518a-2* | 33.9 | 33.67 |
| hmr-miR-206 | 40 | 40 | hmr-miR-126 | 36.76 | 34.73 |
| hmr-miR-208 | 40 | 40 | h-miR-106a | 31.62 | 34.62 |
| hmr-miR-216 | 40 | 40 | hr-miR-9 | 34.49 | 35.06 |
| hmr-miR-218 | 40 | 40 | h-miR-30e-3p | 32.36 | 32.83 |
| hmr-miR-323 | 40 | 40 | hmr-miR-148b | 32.4 | 33.19 |
| hmr-miR-338 | 40 | 40 | hmr-miR-340 | 32.06 | 31.79 |
| hmr-miR-34c | 40 | 40 | hr-miR-140 | 30.9 | 32.46 |
| hmr-miR-433 | 40 | 40 | hmr-miR-196a | 32 | 31.28 |
| hmr-miR-448 | 40 | 40 | hmr-miR-26a | 31.76 | 32.04 |
| hmr-miR-98 | 40 | 40 | hmr-miR-449 | 32.81 | 31.69 |
| hm-miR-189 | 40 | 40 | h-miR-505 | 31.27 | 40 |
| hm-miR-199a* | 40 | 40 | h-miR-491 | 34.02 | 40 |
| hm-miR-301 | 40 | 40 | hm-miR-188 | 33.04 | 40 |
| hm-miR-302a | 40 | 40 | hmr-miR-22 | 31.85 | 40 |
| hm-miR-361 | 40 | 40 | hmr-miR-34a | 28.18 | 28.63 |
| hm-miR-375 | 40 | 40 | hmr-miR-195 | 28.44 | 28.76 |
| hm-miR-377 | 40 | 40 | hmr-miR-200a | 30.71 | 29.38 |
| hm-miR-378 | 40 | 40 | hmr-miR-200b | 28 | 26.29 |
| hm-miR-380-5p | 40 | 40 | hmr-miR-342 | 33.44 | 31.33 |
| hm-miR-381 | 40 | 40 | hmr-miR-200c | 28.57 | 30.85 |
| hm-miR-382 | 40 | 40 | hr-miR-99a | 29.47 | 34.65 |
| hm-miR-412 | 40 | 40 | h-miR-146b | 28.45 | 34.2 |
| hm-miR-425 | 40 | 40 | hmr-miR-324-3p | 27.79 | 32.16 |
| hm-miR-450 | 40 | 40 | h-miR-20b | 40 | 26.55 |
| hm-miR-452 | 40 | 40 | h-miR-345 | 40 | 26.22 |
| hm-miR-484 | 40 | 40 | h-miR-500 | 40 | 28.22 |
| hm-miR-485-5p | 40 | 40 | h-miR-501 | 40 | 29.58 |
| hm-miR-486 | 40 | 40 | hmr-miR-150 | 26.62 | 31.55 |
| hm-miR-7 | 40 | 40 | hmr-miR-194 | 27.07 | 31.29 |
| hr-miR-124a | 40 | 40 | hmr-miR-10a | 27.01 | 29.02 |
| hr-miR-127 | 40 | 40 | hmr-miR-152 | 29.65 | 30.53 |
| hr-miR-142-3p | 40 | 40 | hmr-miR-139 | 29.46 | 30.11 |
| hr-miR-153 | 40 | 40 | h-miR-18a* | 29.19 | 30.8 |
| hr-miR-431 | 40 | 40 | hmr-miR-29c | 31.62 | 31.25 |
| h-miR-UL112-1 | 40 | 40 | hmr-miR-28 | 30.63 | 31.42 |
| h-miR-UL148D-1 | 40 | 40 | hmr-miR-335 | 31.42 | 32.25 |
| h-miR-UL22A-1* | 40 | 40 | hr-miR-203 | 31.26 | 30.33 |
| h-miR-UL36-1 | 40 | 40 | h-miR-191* | 28.96 | 30.39 |
| h-miR-US25-1 | 40 | 40 | hmr-miR-331 | 28.32 | 29.41 |
| h-miR-US25-2-3p | 40 | 40 | hmr-miR-365 | 29.06 | 28.92 |
| h-miR-US25-2-5p | 40 | 40 | hmr-miR-126* | 29.42 | 29.24 |
| h-miR-US33-1 | 40 | 40 | hmr-miR-100 | 29.69 | 21.51 |
| h-miR-US5-1 | 40 | 40 | hmr-miR-18a | 26.02 | 27.57 |
| h-miR-US5-2 | 40 | 40 | hmr-miR-196b | 26.05 | 27.62 |
| h-miR-105 | 40 | 40 | h-miR-362 | 25.36 | 27.36 |
| h-miR-147 | 40 | 40 | hm-miR-149 | 25.88 | 26.45 |
| h-miR-18b | 40 | 40 | h-miR-17-3p | 25.13 | 26.62 |
| h-miR-198 | 40 | 40 | hmr-miR-27b | 26.93 | 27.62 |
| h-miR-202 | 40 | 40 | hmr-miR-183 | 26.9 | 27.48 |
| h-miR-220 | 40 | 40 | h-miR-151 | 27.39 | 27.32 |
| h-miR-302b* | 40 | 40 | h-miR-182* | 25.93 | 28.97 |
| h-miR-302c* | 40 | 40 | hr-miR-192 | 25.1 | 28.6 |
| h-miR-302d | 40 | 40 | hmr-miR-26b | 26.76 | 26.43 |
| h-miR-325 | 40 | 40 | hmr-miR-186 | 26.71 | 26.62 |
| h-miR-368 | 40 | 40 | hr-miR-324-5p | 26.35 | 27.44 |
| h-miR-369-3p | 40 | 40 | hm-miR-182 | 26.02 | 25.99 |
| h-miR-369-5p | 40 | 40 | hm-miR-15a | 25.43 | 25.97 |
| h-miR-370 | 40 | 40 | hmr-miR-29a | 25.15 | 24.74 |
| h-miR-371 | 40 | 40 | hmr-miR-181c | 25.55 | 25.67 |
| h-miR-372 | 40 | 40 | hmr-miR-135a | 24.9 | 26.05 |
| h-miR-373* | 40 | 40 | hmr-miR-212 | 25.99 | 26.51 |
| h-miR-376a | 40 | 40 | hmr-miR-24 | 26.56 | 26.69 |
| h-miR-376b | 40 | 40 | h-miR-200a* | 21.3 | 30.11 |
| h-miR-380-3p | 40 | 40 | h-miR-422b | 21.49 | 25.98 |
| h-miR-383 | 40 | 40 | hmr-miR-99b | 24.06 | 23.8 |

TABLE 4-continued

Global miRNA expression, represented as Ct values assayed by multiplexed qRT-PCR analysis in ARCaP$_E$ and ARCaP$_M$ PCa EMT bone metastatic model.

| microRNA names | Ct values ARCaP$_E$ | Ct values ARCaP$_M$ | microRNA names | Ct values ARCaP$_E$ | Ct values ARCaP$_M$ |
|---|---|---|---|---|---|
| h-miR-384 | 40 | 40 | h-miR-423 | 24.53 | 24.03 |
| h-miR-409-5p | 40 | 25.02 | hmr-miR-30b | 23.96 | 22.43 |
| h-miR-410 | 40 | 40 | hmr-miR-30a-5p | 24.77 | 23.6 |
| h-miR-453 | 40 | 40 | hmr-miR-339 | 22.94 | 23.62 |
| h-miR-490 | 40 | 40 | hmr-miR-106b | 22.43 | 23.12 |
| h-miR-493 | 40 | 40 | hmr-miR-15b | 23.06 | 23 |
| h-miR-496 | 40 | 40 | hmr-let-7d | 22.85 | 23.16 |
| h-miR-498 | 40 | 40 | hmr-miR-23b | 23.95 | 24.63 |
| h-miR-499 | 40 | 40 | hmr-miR-130b | 24.04 | 24.55 |
| h-miR-503 | 40 | 40 | hm-let-7g | 24.45 | 24.98 |
| h-miR-509 | 40 | 40 | hmr-miR-17-5p | 24.92 | 24.94 |
| h-miR-515-5p | 40 | 40 | hr-let-7f | 25.03 | 25.06 |
| h-miR-518a | 40 | 40 | hmr-miR-107 | 24.75 | 25.5 |
| h-miR-518b | 40 | 40 | h-miR-193b | 24.39 | 25.77 |
| h-miR-518c | 40 | 40 | h-miR-197 | 23.35 | 23.37 |
| h-miR-518c* | 40 | 40 | hmr-let-7b | 23.61 | 22.73 |
| h-miR-518d | 40 | 40 | hmr-let-7c | 24.15 | 25.33 |
| h-miR-518e | 40 | 40 | hmr-miR-181b | 23.35 | 22.94 |
| h-miR-518f | 40 | 40 | hmr-miR-132 | 23.29 | 23.65 |
| h-miR-518f* | 40 | 40 | hmr-miR-23a | 22.24 | 22.33 |
| h-miR-519b | 40 | 40 | hmr-miR-29b | 21.79 | 22.53 |
| h-miR-519c | 40 | 40 | hmr-miR-193a | 24.22 | 24.28 |
| h-miR-519d | 40 | 40 | hmr-miR-30a-3p | 23.57 | 23.91 |
| h-miR-519e | 40 | 40 | hmr-miR-27a | 23.34 | 22.75 |
| h-miR-519e* | 40 | 40 | hmr-miR-181a | 21.52 | 21.94 |
| h-miR-520a | 40 | 40 | hmr-let-7i | 21.42 | 21.52 |
| h-miR-520b | 40 | 40 | hmr-miR-19b | 21.45 | 22.55 |
| h-miR-520c | 40 | 40 | hmr-miR-21 | 21.07 | 21.25 |
| h-miR-520d | 40 | 40 | h-miR-181d | 20.83 | 21.2 |
| h-miR-520d* | 40 | 40 | hmr-let-7e | 21.97 | 22.01 |
| h-miR-520e | 40 | 40 | hr-let-7a | 22.09 | 22.17 |
| h-miR-520g | 40 | 40 | hmr-miR-320 | 21.85 | 20.87 |
| h-miR-520h | 40 | 40 | 18s | 20.85 | 22.99 |
| h-miR-521 | 40 | 40 | hmr-miR-191 | 19.59 | 20.35 |
| h-miR-522 | 40 | 40 | hmr-miR-125b | 21.04 | 20.01 |
| h-miR-523 | 40 | 40 | hmr-miR-19a | 19.78 | 21.24 |
| h-miR-524 | 40 | 40 | hmr-miR-20a | 20.77 | 21.58 |
| h-miR-524* | 40 | 40 | hr-miR-221 | 21.31 | 20.34 |
| h-miR-525 | 40 | 40 | hmr-miR-30c | 20.96 | 20.02 |
| h-miR-525* | 40 | 40 | h-miR-93 | 21.68 | 22.68 |
| h-miR-526a | 40 | 40 | hmr-miR-103 | 21.5 | 22.23 |
| h-miR-526b | 40 | 40 | hmr-miR-30d | 22.31 | 21.58 |
| h-miR-526b* | 40 | 40 | hmr-miR-210 | 22.59 | 21.77 |
| h-miR-526c | 40 | 40 | hmr-miR-25 | 20.37 | 20.91 |
| h-miR-527 | 40 | 40 | hmr-miR-125a | 21.15 | 21.27 |
| h-miR-95 | 40 | 40 | hmr-miR-16 | 20.48 | 20.36 |
| h-miR-494 | 40 | 36.35 | hmr-miR-222 | 17.91 | 17.18 |
| h-miR-432 | 36.5 | 40 | hmr-miR-92 | 18.37 | 18.69 |
| hmr-miR-30e-5p | 35.89 | 39.02 | | | |
| h-miR-517a | 40 | 40 | | | |
| hmr-miR-328 | 40 | 40 | | | |

TABLE 5 miRNA differentially expressed in metastatic ARCaP$_M$ prostate cancer cells and non-metastatic ARCaP$_E$ prostate cancer cells by multiplexed real time PCR analysis. miRNA in bold are in the DLK1-DIO3 mega-cluster.

| High in metastatic ARCAP$_M$ prostate cancer cells Relative fold change | ARCaP$_E$ | ARCaP$_M$ | Low in metastatic ARCaP$_E$ prostate cancer cells Relative fold change | ARCaP$_E$ | ARCaP$_M$ |
|---|---|---|---|---|---|
| h-miR-345 | 0 | 14066.74 | h-miR-488 | 610655.84 | 0 |
| h-miR-20b | 0 | 11190.60 | h-miR-513 | 535304.41 | 0 |
| h-miR-409-3p | 0 | 5996.90 | h-miR-224 | 280958.98 | 0 |
| h-miR-500 | 0 | 3516.68 | h-miR-517* | 100720.65 | 0 |
| h-miR-409-5p | 0 | 2336.28 | h-miR-516-5p | 47975.16 | 0 |

TABLE 5-continued miRNA differentially expressed in metastatic ARCaP$_M$ prostate cancer cells and non-metastatic ARCaP$_E$ prostate cancer cells by multiplexed real time PCR analysis. miRNA in bold are in the DLK1-DIO3 mega-cluster.

| High in metastatic ARCAP$_M$ prostate cancer cells Relative fold change | ARCaP$_E$ | ARCaP$_M$ | Low in metastatic ARCaP$_E$ prostate cancer cells Relative fold change | ARCaP$_E$ | ARCaP$_M$ |
|---|---|---|---|---|---|
| h-miR-424 | 0 | 1468.37 | h-miR-512-5p | 26801.01 | 0 |
| h-miR-501 | 0 | 1370.04 | h-miR-346 | 26068.14 | 0 |
| h-miR-422a | 0 | 1226.22 | h-miR-34b | 20452.65 | 0 |
| h-miR-455 | 0 | 1097.50 | h-miR-326 | 18561.17 | 1 |
| h-miR-367 | 0 | 826.00 | h-miR-514 | 16158.44 | 0 |
| h-miR-502 | 0 | 401.71 | h-miR-202* | 9345.14 | 0 |
| hmr-miR-185 | 0 | 388.02 | h-miR-510 | 6936.54 | 0 |
| hmr-miR-100 | 1 | 290.02 | h-miR-512-3p | 6653.97 | 0 |
| h-miR-154* | 0 | 202.25 | h-miR-302b | 5293.48 | 0 |
| h-miR-379 | 0 | 181.02 | h-miR-215 | 4870.99 | 0 |
| h-miR-487 | 0 | 133.44 | h-miR-506 | 3743.05 | 0 |
| hmr-miR-184 | 0 | 131.60 | h-miR-508 | 2702.35 | 0 |
| hr-miR-134 | 1 | 82.13 | h-miR-302c | 2628.46 | 0 |
| h-miR-519a | 0 | 66.72 | h-miR-516-3p | 1964.57 | 0 |
| h-miR-517b | 0 | 46.21 | h-miR-515-3p | 1897.65 | 0 |
| h-miR-374 | 0 | 29.04 | h-miR-492 | 1833.01 | 0 |
| hmr-miR-214 | 1 | 22.47 | h-miR-337 | 1379.57 | 0 |
| h-miR-302a* | 1 | 13.64 | h-miR-217 | 749.61 | 1 |
| | | | h-miR-329 | 666.29 | 1 |
| | | | h-miR-451 | 621.67 | 0 |
| | | | h-miR-200a* | 448.82 | 0 |
| | | | h-miR-505 | 424.61 | 0 |
| | | | h-miR-330 | 401.71 | 1 |
| | | | hmr-miR-22 | 284.05 | 0 |
| | | | h-miR-363 | 230.72 | 0 |
| | | | h-miR-432* | 179.77 | 0 |
| | | | h-miR-211 | 141.04 | 0 |
| | | | hm-miR-188 | 124.50 | 0 |
| | | | h-miR-31 | 98.36 | 1 |
| | | | hmr-miR-213 | 93.70 | 1 |
| | | | hmr-miR-33 | 90.51 | 0 |
| | | | h-miR-129 | 69.55 | 0 |
| | | | h-miR-507 | 69.07 | 0 |
| | | | h-miR-491 | 63.12 | 0 |
| | | | h-miR-146b | 53.82 | 1 |
| | | | h-miR-495 | 46.21 | 0 |
| | | | h-miR-UL22A-1 | 38.59 | 0 |
| | | | hr-miR-99a | 36.25 | 1 |
| | | | h-miR-483 | 30.91 | 1 |
| | | | hmr-miR-150 | 30.48 | 1 |
| | | | h-miR-422b | 22.47 | 1 |
| | | | hmr-miR-324-3p | 20.68 | 1 |
| | | | hmr-miR-194 | 18.64 | 1 |
| | | | hr-miR-192 | 11.31 | 1 |
| | | | h-miR-485-3p | 10.34 | 1 |
| | | | h-miR-182* | 8.22 | 1 |
| | | | h-miR-106a | 8.00 | 1 | miR-409-3p/-5p Inhibits Tumor Suppressor Genes in PCa

Targetscan 6.2 (June 2012) software analysis revealed putative miR-409-5p targets that include tumor suppressor genes like stromal antigen 2 (STAG2), ras suppressor protein 1 (RSU1), retinoblastoma-like 2 (RBL2) and nitrogen permease regulator-like 2 (NPRL2). Predicted mRNA targets of miR-409-3p include polyhometic 3 (PHC3), RSU1 and tumor suppressor candidate 1 (TUSC1). The miR-409-5p and -3p targets were validated by qRT-PCR and were found to be downregulated in metastatic ARCaPM cells that express elevated levels of miR-409-3p/5p compared to ARCaPE cells that express lower levels of miR-409-3p/5p (FIG. 2A). Consistently we observed elevated protein expression of STAG2 and RSU1 in ARCaPE cells compared to ARCaPM cells (FIG. 2B). We demonstrated that miR-409-5p binds the 3'UTR of STAG2 and RSU1 (FIG. 7B, C). Additionally the binding sites of miR-409-5p and miR-409-3p on RSU1 3'UTR are indicated in FIG. 7A. Using gene cards and string interactions, we created a cytoscape map of the possible human cancer pathways regulated by miR-409-5p and miR-409-3p that would account for its activity in cells. miR-409-3p is predicted to activate the Ras signaling pathway, hypoxia inducible factor-1a pathway, regulate polycomb group proteins and osteoblastic pathways (FIG. 2C). miR-409-5p is predicted to activate E2F pathway, Ras signaling pathway, Akt pathway and aneuploidy (FIG. 2D). Taken together, we demonstrate that miR-409-3p/-5p is elevated in the bone metastatic EMT cell models and it functions by repressing several tumor suppressor genes.

Human Prostatic Tissues with Higher Gleason Score and Prostate Cancer Bone Metastasis Tissues Express Elevated Levels of miR-409

Figure 3:
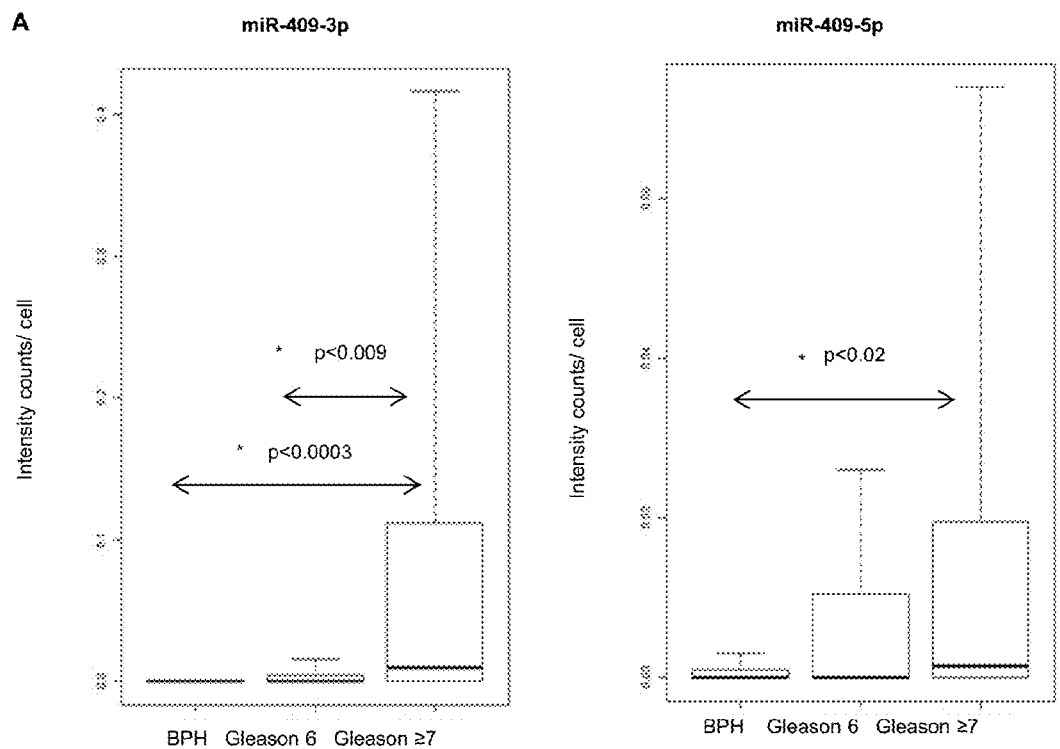
FIG. 3 depicts human prostatic tissues with higher Gleason score and prostate cancer bone metastasis tissues express elevated levels of miR-409. A, Quantitative analysis of miR-409-3p and miR-409-5p expression in tumor tissues with Gleason grade. B, Representative image of miR-409-3p (green) and miR-409-5p (red) expression in tumor tissues and H&E staining (40×). The tissue array consisted of BPH (N=14), Gleason 6 (N=26) and Gleason ≥7 (N=35), data analyzed by Kruskal-Wallis one way analysis of variance-Tukey method. C, miR-409-3p expression in Gleason_high (N=29) and Gleason_low (N=78) based on MSKCC dataset. D, Kaplan-Meier disease free survival (DFS) curves for the prostate cancer patients, based on miR-409-3p expression in the MSKCC dataset. The y-axis is disease free survival probability, and the x-axis is survival in months. Top line represents the DFS of patients with miR-409-3p lower than the median of the normal individuals (n=78). Bottom line represents the DFS of patients with miR-409-3p higher than the median of the normal individuals (n=29). Data was analyzed using log-rank test (p=4.3e-05). *: $p<0.05$ were considered to be statistically significant.
Figure 3:
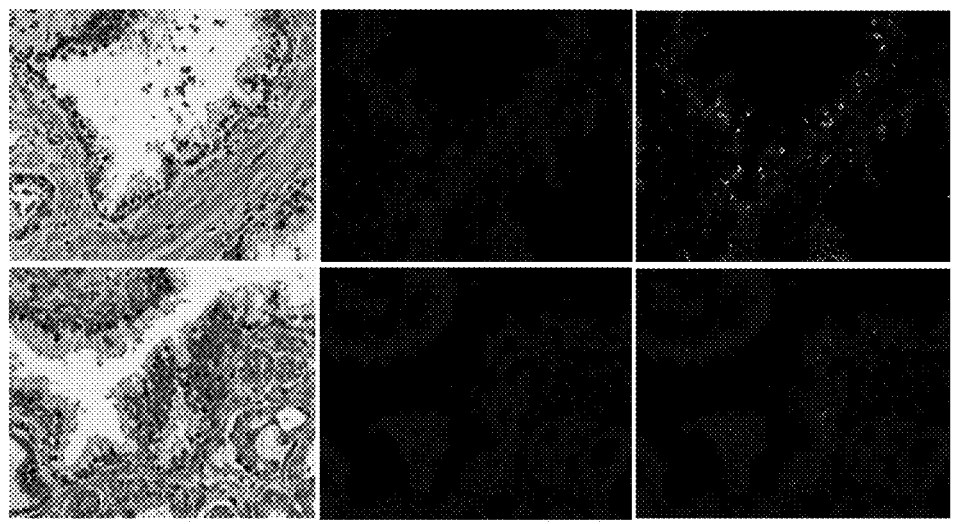
Figure 3:
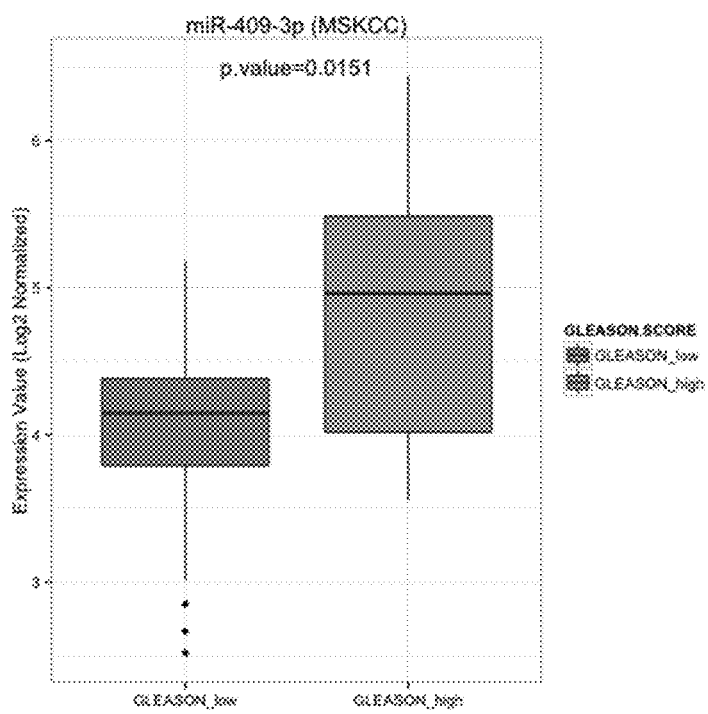
Figure 3:
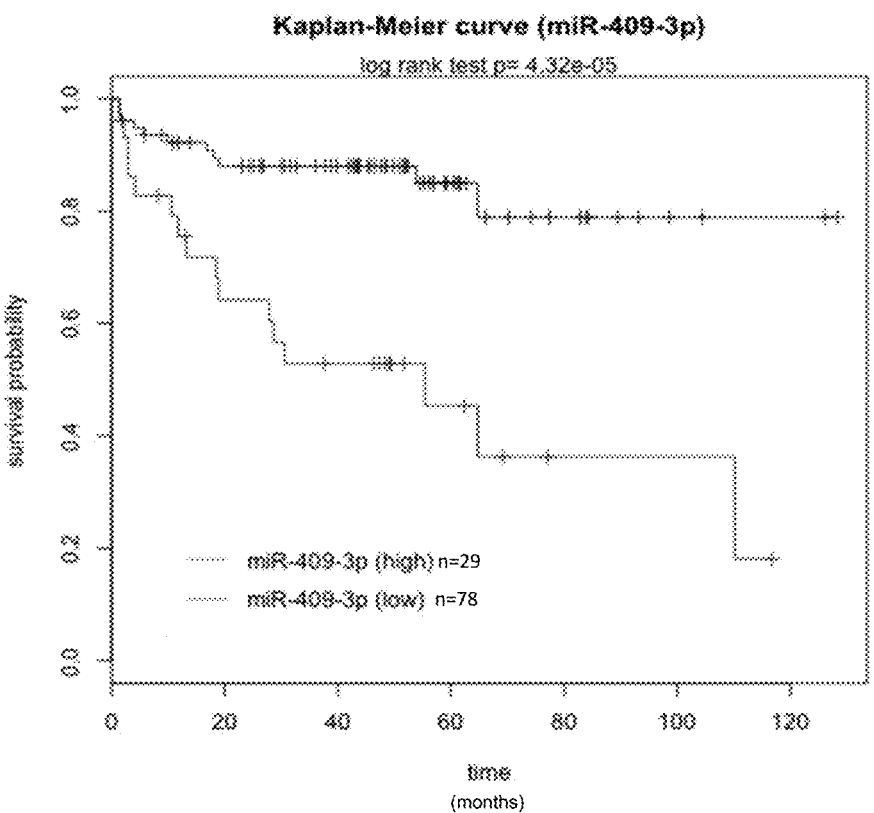

In order to validate our findings in clinical samples, we determined the levels of miR-409-3p/-5p in human prostate tissues with various Gleason scores using in situ hybridization (ISH) and multiplexed quantum dot (QD) labeling. The miRNA probes were biotin-labeled (Exiqon) and further labeled to a streptavidin conjugated QD at a specified wavelength. miR-409-3p/-5p was detected both in the tumor tissues. The tissues were separated into three groups, BPH (N=14), Gleason 6 (N=26) and Gleason ≥7 (N=35). Tumors with higher Gleason ≥7 had significantly higher miR-409-3p and miR-409-5p staining in the tumor areas compared to the tissues with BPH. miR-409-3p was significantly higher in the Gleason ≥7 compared to Gleason 6 (FIG. 3A), as analyzed by Kruskal-Wallis one way analysis of variance-Tukey method. A representative image of Gleason 8, shows increased staining of miR-409-3p (green) and -5p (red) in PCa tissues (FIG. 3B). We used a dataset published by MSKCC (Taylor et al. Cancer cell 2010) to determine the miR-409-3p expression in different Gleason score tissues in FIG. 3C. The miR-409-3p expression levels were compared between Gleason_low (Gleason 6,7; n=86) and Gleason_high (Gleason 8, 9; n=12) groups (FIG. 3C). miR-409-3p expression was significantly elevated in higher Gleason tissues compared to low Gleason tissues, consistent with our own staining data (p value=0.0151). The miR-409-5p expression was not provided in this dataset. Furthermore, we analyzed the survival of this patient cohort based on their miR-409-3p expression level (FIG. 3D). The patients were separated into two groups based on their miR-409-3p expression levels relative to the normal samples. We found that the patients with higher miR-409-3p than normal sample were correlated with poor progression free survival ($p=4.32 \times 10^{-5}$). This indicates that the miR-409-3p is clinically relevant in PCa. Collectively, these results demonstrate that miR-409 expression correlated with higher Gleason score in prostatic tissues and with patient progression free survival, while not wishing to be bound by any particularly theory, linking miR-409 expression with tumor progression.

Figure 4:
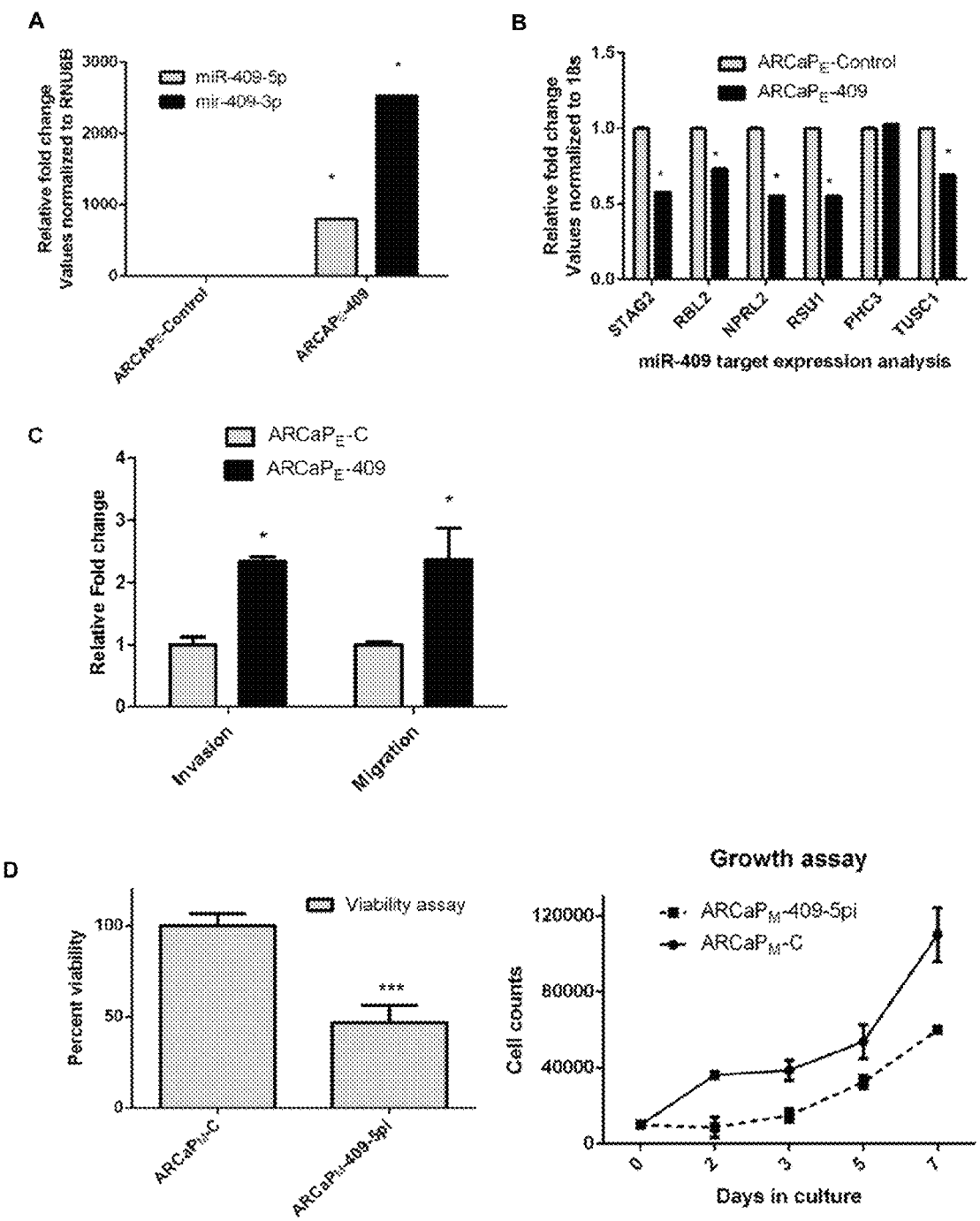
FIG. 4 shows that ectopic expression of miR-409 leads to increased invasiveness and aggressiveness of prostate cancer cells and conversely inhibition of miR-409 results in increased cell death in PCa cells. A, miR-409-5p and -3p expression by qRT-PCR in ARCaPE-C and ARCaPE-409 expressing PCa cells. B, RNA expression of miR-409-5p/-3p targets in ARCaPE-C and ARCaPE-409 expressing PCa cells assayed by real time PCR. (miR-409-5p mRNA targets: STAG2, RBL2, NPRL2 and RSU1 and miR-409-3p mRNA targets: RSU1, PHC3 and TUSC1). C, Invasion and migration assay of in ARCaPE-C and ARCaPE-409 expressing PCa cells. D, Cell viability in ARCaPM PCa cells in response to a miR-409-5p inhibitor. Growth curve of ARCaPM-C and ARCaPM-409-5pi PCa cells. E, Expression of miR-409-5p assayed by qRT-PCR in ARCaPM-C control PCa and ARCaPM-409-5pi (miR-409-5p inhibitor transfected cells). F, RNA expression of miR-409-5p targets in ARCaPM-C control and ARCaPM-409-5pi cells assayed by qRT-PCR. (miR-409-5p mRNA targets: NPRL2 and STAG2). G, Protein expression of STAG2 and RSU1 in ARCaPM-C cells and ARCaPM-409-5pi cells. *: $p<0.05$ were considered to be statistically significant by t-test.
Figure 4:
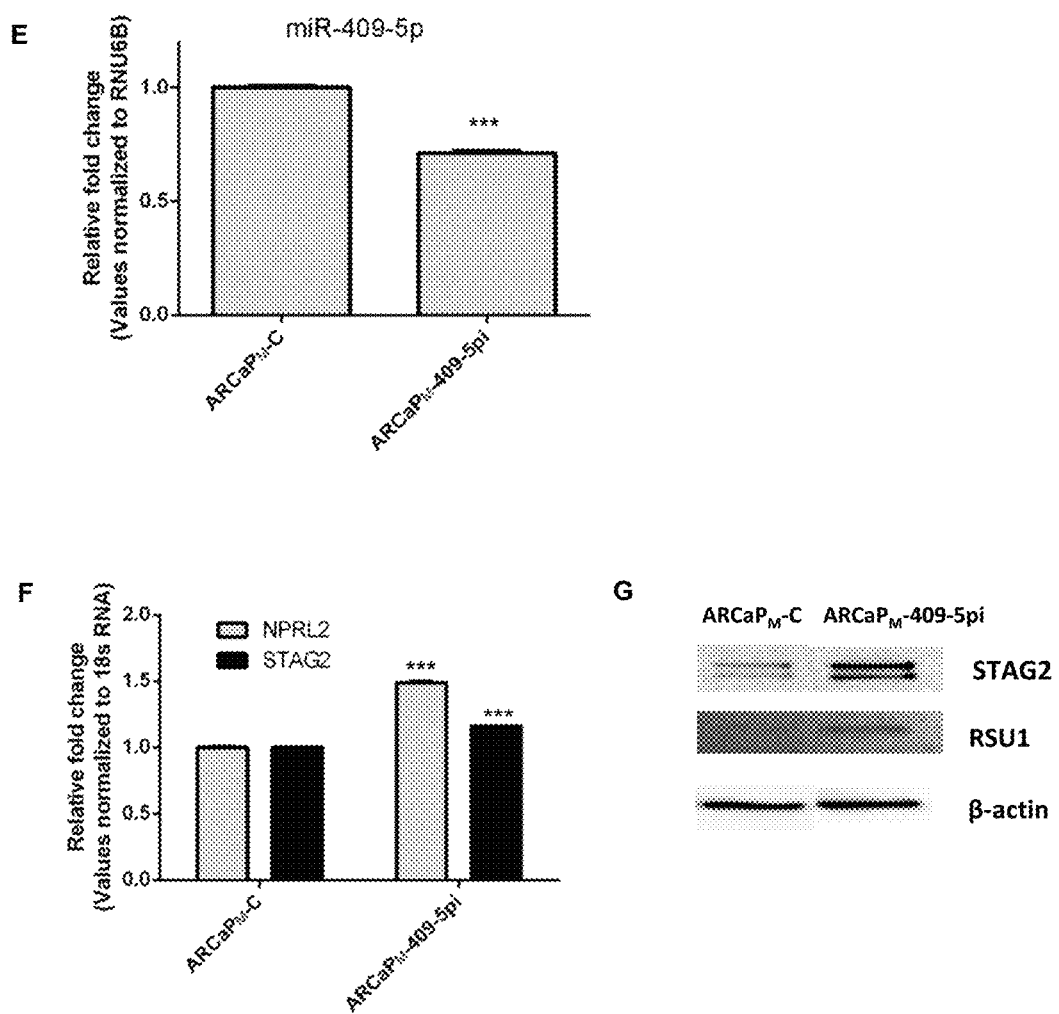
Figure 8:
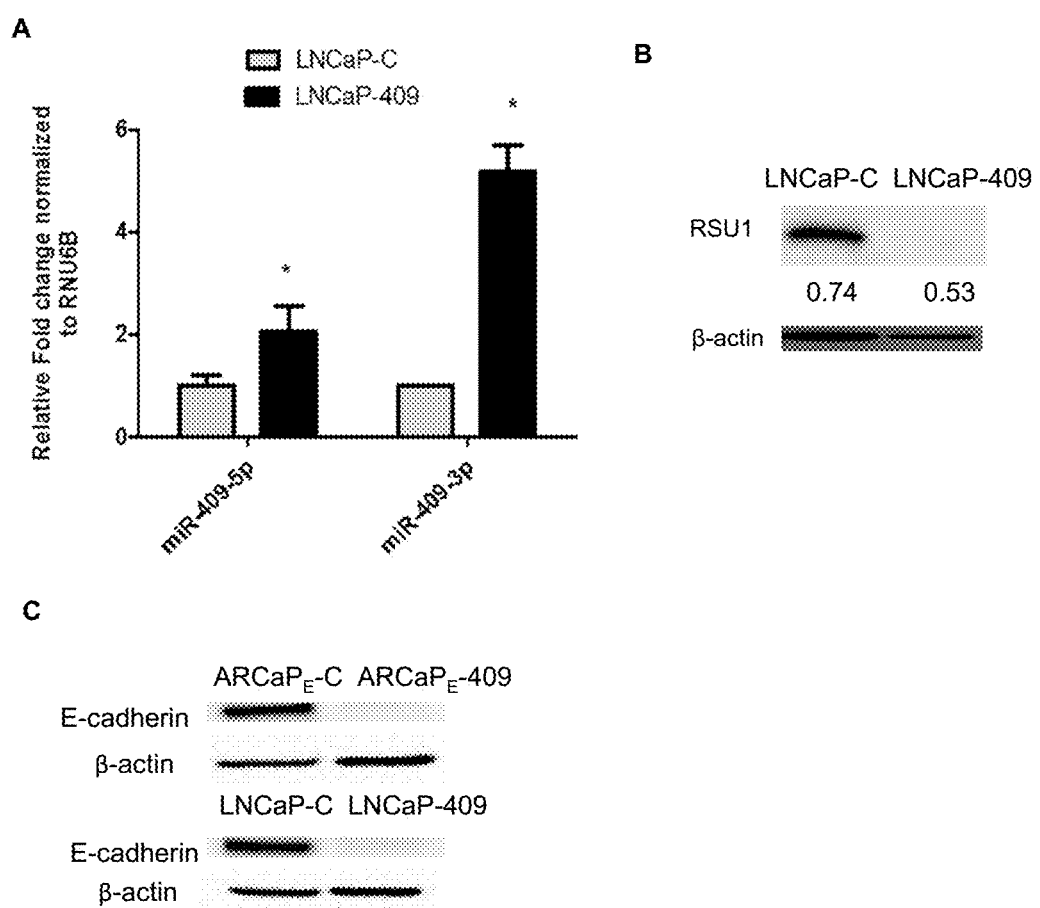
FIG. 8 depicts the effect of miR-409 overexpression in LNCaP cells. A, miR-409-5p and miR-409-3p levels in LNCaP control cells (LNCaP-C) and LNCaP miR-409 expressing cells (LNCaP-409) measured by qRT-PCR. B, Protein expression of RSU1 in LNCaP-C and LNCaP-409 PCa cells. C, Protein expression of E-cadherin in ARCaP-409 and LNCaP-409 PCa cells compared to their controls, measured by western analysis.

Ectopic Expression of miR-409-3p/-5p Leads to Increased Invasiveness and Aggressiveness of PCa Cells and Conversely Inhibition of miR-409-3p/-5p Results in Increased Cell Death in PCa Cells To determine the effects of miR-409-3p/-5p action in PCa, we ectopically introduced this miRNA in less aggressive epithelial-type ARCaPE cells and LNCaP cells. A significant increase in miR-409-3p/-5p expression was confirmed using qRT-PCR (FIG. 4A, FIG. 8A). The mRNA expression of target genes of miR-409-3p/-5p was determined using qRT-PCR. We report that miR-409-5p target mRNAs (STAG2, RSU1, RBL2, and NPRL2) were decreased in ARCaPE cells that overexpress miR-409 (ARCAPE-409) compared to the control miRNA-treated cells (FIG. 4B). Two of the three mRNA targets of miR-409-3p were also decreased in ARCaPE-409 cells compared to control (RSU1 and TUSC1), but not PHC3 (FIG. 4B). Moreover, ARCaPE-409 cells showed increased migratory and invasive capacity compared to control PCa cells (FIG. 4C).

On the contrary, inhibition of miR-409-3p in ARCaPM PCa cells using a shRNA inhibitor resulted in cell death of PCa cells and hence further experiments could not be carried out due to complete lethality of the cells in vitro Inhibition of miR-409-5p using shRNA resulted in cell death of aggressive metastatic PCa cells (FIG. 4D) compared to the control scramble miRNA expressing cells. We generated stable lentiviral clones of ARCaPM PCa cells expressing miR-409-5p inhibitor (ARCaPM-409-5pi). ARCaPM-409-5pi PCa cells had a decreased growth rate compared to ARCaPM-C cells (FIG. 4D). ARCaPM-409-5pi cells had decreased miR-409-5p levels compared to ARCaPM-C cells (FIG. 4E). Next, we measured the levels of mRNA targets of miR-409-5p, which include NPRL2 and STAG2, and found that they were increased in ARCaPM-409-5pi treated cells compared to ARCaPM-C control cells (FIG. 4F). Furthermore, immunoblot analysis confirmed increases in protein levels of STAG2 and RSU1 in ARCaPM-409-5pi cells compared to control cells (FIG. 4G). Taken together, these results demonstrate that over-expression of miR-409-3p/-5p in less aggressive PCa cells decreased their expression of tumor suppressors and increased their invasion and migration whereas inhibition of miR-409-5p in aggressive PCa cells decreased their growth and increased their cell death.

Ectopic Expression of miR-409-3p/-5p in the Prostate Gland Transforms Normal Prostate Epithelia, Promotes Tumorigenecity, EMT and Stemness In Vivo To test if miR-409-3p/-5p is oncogenic in vivo, we implanted human embryonic kidney cells, 293T producer cells, transfected with the miR-409 expressing lentiviral vector carrying green fluorescent protein (GFP) or control vector carrying a GFP plasmid, orthotopically into the prostate gland of athymic nude mice (N=5/group). Tumor development was monitored using the tumor specific near-infrared (NIR) dye (IR783) (Yang, et al. Clin Cancer Res 2010).

Figure 5:
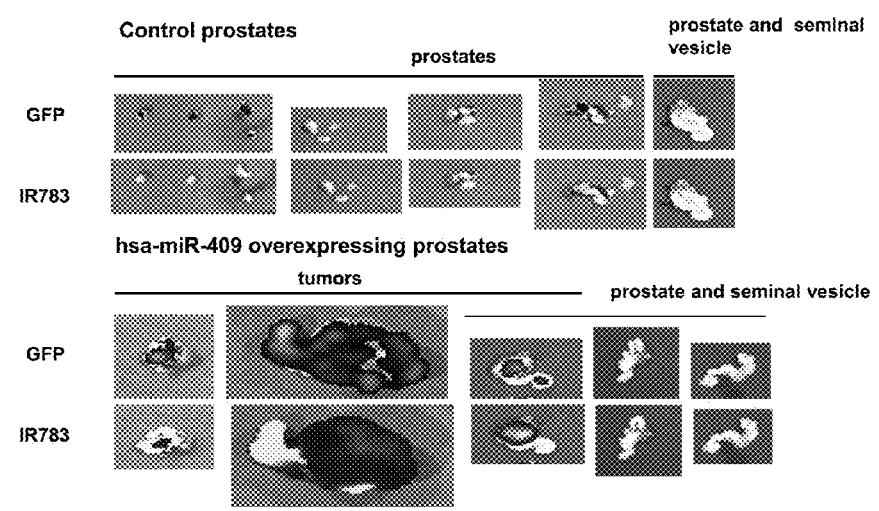
FIG. 5 shows that ectopic expression of miR-409 in the prostate gland transforms normal prostate epithelia, promotes tumorigenecity, EMT and sternness in vivo. A, Comparison of normal prostate and miR-409 expressing prostates. Top row represents green fluorescence for cells containing control GFP plasmid or miR-409 GFP expressing plasmid. Bottom panel represent tumor specific NIR dye (IR783) uptake in control or miR-409 expressing prostates. B, H&E staining of normal control prostate and adenocarcinoma lesions of miR-409 overexpressing prostates (40×), followed by miRNA detection of scramble miRNA and miR-409-5p/-3p of control and miR-409 expressing tissues by ISH and QD detection (40×). C, IHC staining of Ki-67, STAG2, RSU1, vimentin and p-AKT in control prostate and miR-409 expressing prostate tissues (20×).
Figure 5:
Figure 5:
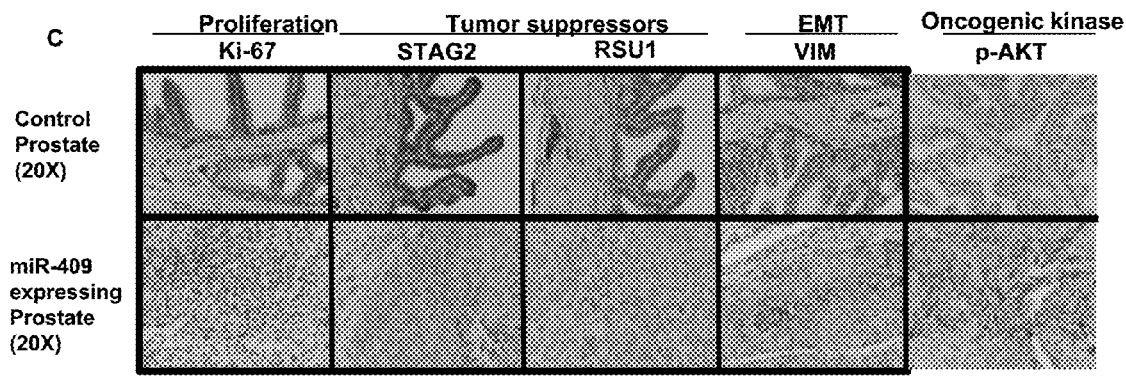

The rationale behind this procedure is that the lentivirus will be secreted by the producer cells (293T) and infect prostate epithelial and/or stromal cells in vivo. Strikingly, prostate tumors developed in two to five months in three out of five mice that received the producer cells transfected with miR-409 (FIG. 5A). Mice that were implanted with producer cells expressing control lentiviral plasmid did not develop any tumors in the prostate.

Figure 9A:
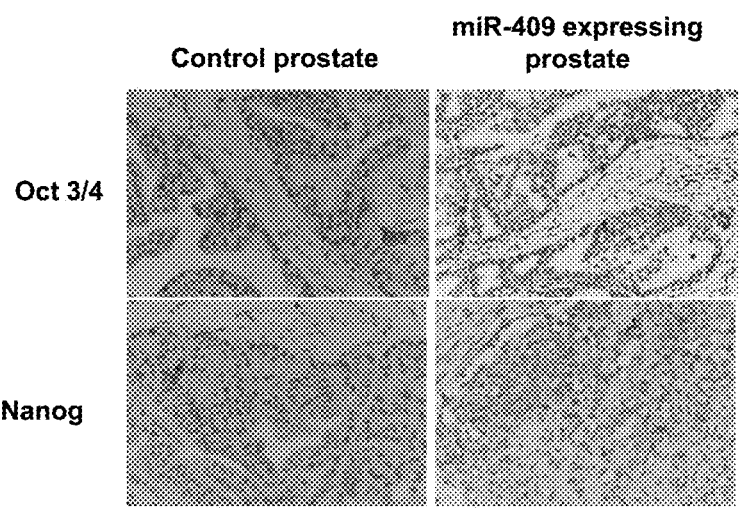
FIG. 9A depicts Nanog and Oct-3/4 expression in tumor and stromal areas of prostates expressing miR-409 compared to control normal prostates, using IHC analysis.
Figure 9B:
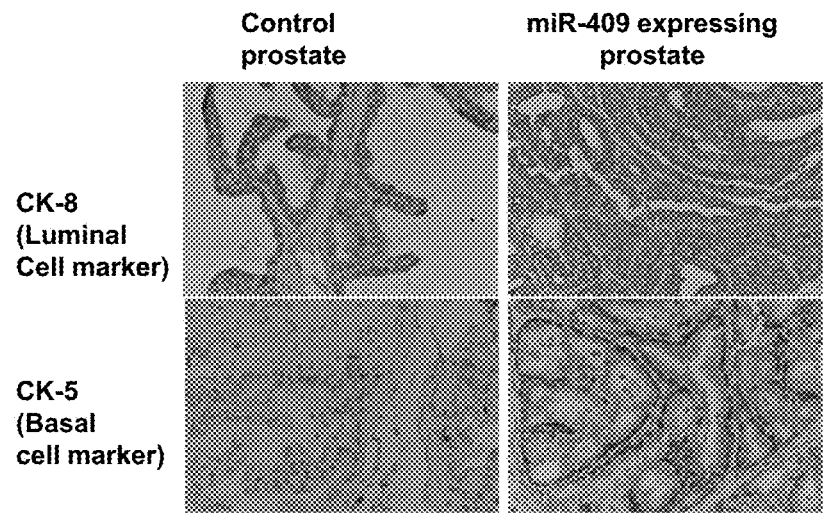
FIG. 9B depicts IHC staining of cytokeratin 8 (CK-8) and cytokeratin 5 (CK-5) in normal control prostate, and tumors of control and miR-409 expressing prostates.

The tumors had green fluorescence and showed tumor specific dye uptake (IR783) (FIG. 5A). H&E staining of tissue sections revealed tumors ranging from prostatic interstitial neoplasia, basal cell hyperplasia, and adenocarcinoma in the miR-409 prostates (FIG. 5B). The tissue sections were also analyzed for miR-409-3p/-5p levels using ISH-QD labeling. miR-409-3p and miR-409-5p expression was observed only in miR-409 expressing prostates in tumor cells but not in control prostates (FIG. 5B). Levels of miR-409 expression appear to correlate with the overall size of the tumors. Immunohistochemical staining revealed elevated expression of tumor proliferation markers such as Ki-67 and oncogenic kinases like p-AKT (FIG. 5C), down-regulated expression of STAG2 and RSU1 and upregulated expression of mesenchymal markers, such as vimentin, when compared to the control prostate gland (FIG. 5C). Immunohistochemical staining of orthotopic tumors revealed positive staining of Oct-3/4 (strong nuclear staining) and Nanog (weak nuclear staining), both of which are stem cell markers, in both the epithelial and the stromal compartment of miR-409 expressing neoplastic prostates (FIG. 9). Strikingly, in the epithelial compartment, both the basal and luminal cells in the prostate underwent proliferation, as exhibited by strong Ki-67 staining, in response to uptake of miR-409-3p/-5p, with cytokeratin 5, representing the basal cell marker and cytokeratin 8, representing the luminal cell marker (FIG. 9). Taken together, while not wishing to be bound by any particularly theory, the inventors believe that, miR-409-3p/-5p is oncogenic and its expression is sufficient to drive tumorigenesis of the adult normal prostate gland.

Inhibition of miR-409-5p Results in Decreased Bone Metastasis of Aggressive PCa In Vivo Since inhibition of miR-409-3p using a shRNA inhibitor resulted in complete cell lethality, further experiments could not be carried out Inhibition of miR-409-5p in ARCaPM cells resulted in reversal of EMT (MET; FIG. 6A), accompanied by an increase in E-cadherin expression and a decrease in N-cadherin expression and epithelial morphological changes (FIG. 6A). Inversely, overexpression of miR-409 in ARCaPE and LNCaP resulted in decreased E-cadherin expression (FIG. 8C). Knocking down miR-409-5p also resulted in moderate decrease in migration and invasion of cancer cells (FIG. 6A). To determine if miR-409 plays a role in cancer metastasis, we inoculated viable ARCaPM-C control cells or viable ARCaPM-409-5pi cells via the intracardiac route into SCID/Beige mice (N=5/group) to mimic in vivo metastasis. Mice that received ARCaPM-C cells had 100% incidence of bone metastasis, whereas mice that received ARCaPM-409-5pi cells did not develop any metastasis at 15 weeks. The luciferase tagged cancer cells were imaged by luciferase imaging (FIG. 6B). The survival of the ARCaPM-C and ARCaPM-409-5pi injected mice are depicted as a Kaplan Meier curve, where majority (4/5) of control mice died by 15 weeks but not ARCaPM-409-5pi injected mice (FIG. 6C). Using X-ray imaging we observed bone metastatic tumor sites in tibia, femur, mandible and humerus (FIG. 6D). Each mouse developed 1 to 5 metastatic tumors in the control group, detected by IR783 imaging and confirmed by luciferase imaging (FIG. 6E). X-ray imaging of mice inoculated with ARCaPM-409-5pi revealed no evidence of bone lesions consistent with the lack of luciferase signals (FIG. 6B and data not shown). Thus, inhibition of miR-409-5p induced MET and significantly abrogates the metastatic potential of metastatic PCa cells in vivo. Taken together, these studies demonstrate that miR-409 is associated with bone metastasis of human PCa cells in mouse models.

Example 5—Methods

Cell Culture

Three human PCa bone metastatic progression models, ARCaP$_E$ and ARCaP$_M$ (13), LNCaP and C4-2 (14) were used in our study. PCa cells and 293T cells were cultured in T-medium (GibcoBRL) supplemented with 5% heat inactivated fetal bovine serum (Bio-Whittaker) with 5% FBS and 1% penicillin-streptomycin. HCC827 and A431 cells were obtained from the American Type Culture Collection and were maintained in RPMI-1640 and DMEM, respectively, plus 10% FBS and 1% penicillin-streptomycin. All cells were tested for mycoplasma every three months and were negative. The embryonic stem cells and induced pluripotent stem cells (iPSC) derived small RNA preparations were provided by Drs. Sareen and Svendsen of Regenerative Medicine Institute at Cedars-Sinai Medical Center.

miRNA Expression

Quantitative Real Time PCR (qRT-PCR):

Cells were trypsinized and total miRNA was extracted using a mirVana miRNA isolation kit (Ambion). miRNA expression analysis by qRT-PCR was performed separately for each miRNA using specific primer sets (Applied Biosystems) as previously described (Josson et al., Radiation modulation of microRNA in prostate cancer cell lines. The Prostate 2008; 68: 1599-606). RNU6B was used for normalization.

mRNA Analysis:

Total RNA was isolated from confluent monolayers of cells using the RNeasy Mini Kit (Qiagen, Valencia, Calif.). cDNA was made using Superscript®III reverse transcriptase (Life Technologies, Grand island, NY). mRNA primers were designed and synthesized at Integrated DNA Technologies (Coralville, Iowa). mRNA expression levels were determined by qRT-PCR assays and SYBR Green Dye (Applied Biosystems). Samples were analyzed using the $\Delta\Delta C_t$ method and were normalized to 18S ribosomal RNA.

MSKCC Database Analysis

The dataset was published by MSKCC team (Taylor et al., Cancer cell 2010) and was obtained from cBioPortal (Gao et al., Science signaling 2013). The expression levels of miR-154 and miR-379 were analyzed along with the survival data in the dataset. For the survival analysis of miR-379, the expression levels of miR-379 in patients with non-metastatic disease were compared with the median expression level of normal individuals. The disease free survival of patients with miR-379 expression levels higher than normal individual (n=29) was compared with that with lower miR-379 expression levels (n=78). Kaplan-Meier survival curve was done by log-rank test between high and low expression groups. The expression levels of miR-154* were not available in the dataset. For the analysis of miR-154, the expression levels of normal healthy individuals (n=29) were compared with expression levels of primary (n=99) and metastatic PCa patients (n=14). Two-tailed student t tests were done between the normal group and two primary and metastatic groups for analysis of differential expression of miR-154.

3'UTR Assay

Stromal antigen 2 (STAG2) mutant luciferase activity: 3'UTR STAG2 luciferase construct (Switchgear genomics) was used as the wild type (WT) construct and it was further mutated as described below. miR-154* mimic and control miRNA were transiently transfected along with the WT or mutant (STAG2) construct into these 293T cells and luciferase activity was determined 24 h later using Lightswitch luciferase assay system (Switchgear genomics).

3'UTR Mutant constructs: Mutated 3' UTR luciferase constructs were produced by sited-directed mutagenesis. Briefly, primer pairs with two sequential base pair mutations in the miRNA seed sequence of the 3' UTR were generated. Following polymerase chain reaction amplification, parental methylated template DNA was digested for 1 hour with Dpn I. 2 µl of the reaction was then transformed into XL-10 Gold bacteria. 16 hours post-transformation, colonies were picked for liquid culture. Plasmid DNA was isolated by the Zyppy Plasmid Miniprep Kit according to manufacturer's directions (Zymo Research). Mutations were confirmed by sequencing before proceeding with luciferase assays.

Primers

```
miR-154* Stag2 1
                                        (SEQ ID NO: 27)
Aactagaactgctgagaggactgtatatacaattttaaacctaagttgat tttttttctc miR-154* Stag2 2
                                        (SEQ ID NO: 28)
Gagaaaaaaatcaacttaggtttaaaattgtatatacagtcctctcagc agttctagtt
```

Lentiviral Transduction

ARCaP$_E$ PCa cell lines were transduced with lentivirus expressing control or miRZip-154* (miR-154*i) or miRZip-379 (miR-379i) (System Biosciences) or cluster overexpression plasmid (custom made, miR-154*, miR-379, miR-409-3p/-5p) with green fluorescent protein (GFP) or control GFP plasmid. ARCaP$_M$ PCa cell lines were transduced with lentivirus expressing cluster inhibitor plasmid (custom made) with GFP. Lentiviral preparation and transduction of cell lines were performed as per the manufacturer's instructions (System Biosciences, Mountain View, Calif.). GFP positive cells were FACS sorted and cultured in vitro before experiments were performed.

Cell Viability Assay and Invasion Assays

Cell viability assay was performed using trypan blue staining Cancer cell invasion were assayed in Companion 24-well plates (Becton Dickinson Labware) with 8 μm porosity polycarbonate filter membranes.

Western Analysis

Whole cell lysates from cell lines were prepared using a modified RIPA lysis buffer (50 mM Tris HCl, 1% NP-40, 0.5% Na-deoxycholate, 0.1% SDS, 150 mM NaCl, 1 mM EDTA, 10% glycerol) supplemented with 1:100 dilution of the protease inhibitor cocktail and the tyrosine phosphatase inhibitor (Sigma). Proteins were then separated on 4-20% or 10% acrylamide gels (Pierce), and transferred to PVDF membrane (VWR). Membranes were probed with STAG2 (Cell Signaling Technology) antibody. β-actin (Sigma) was used as the normalization control.

In Situ Hybridization (ISH)-Quantum Dots (QD)

Mouse tibia was formalin-fixed and paraffin-embedded. miRNA ISH protocol was followed as per manufacturer's instruction (Exiqon, MA). The scramble and miR154* probes were 5'-biotin labeled. The probes were linked to streptavidin-conjugated QD. Tissue sections were deparaffinized, treated with proteinase-K and dehydrated. ISH was performed for 1 h at 55° C., followed by washes and streptavidin blocking and a reaction with streptavidin-conjugated QD at a specified wavelength. QD staining procedure was followed. Single QD labeling was performed and scramble or miR-154* probes labeled with 625 nm QDs. Images were taken at 40×. H&E staining was performed on subsequent tissue sections.

Human Tissue array:

A Gleason score tissue array was obtained from Vancouver Prostate Center. The use of tissue specimens was approved by the institution review board of the Cedars-Sinai Medical Center (IRB# Pro21228). The tissues consisted of BPH (N=4), Gleason score 6 (N=12) and Gleason 7 (N=7). Each tissue had two sample cores. The tissue array was stained for H&E and graded by a pathologist to confirm the Gleason score. Single QD labeling was performed. miR-154* was labelled with 625 nm QD and ssignals were quantified. The QD fluorescence intensity of each tissue section was determined and analyzed. The groups are not statistically significant using One way ANOVA-Tukey multiple comparison test. Human prostate caner bone tissues were stained following the same procedure, except multiplexed ISH-QD was performed, where miR-154* (red) was stained first followed by miR-409-3p (green) or miR-409-5p (green) which was labeled with 565 nm QD.

In Vivo Metastasis Study:

All animal experiments were IACUC approved and done in accordance with institutional guidelines. Luciferase tagged ARCaP$_M$ control and ARCaP$_M$-154*i cells were injected intra-cardially in SCID/beige mice (Charles River Laboratories) (N=5). Mice were imaged using X-ray and bioluminescence using IVIS® Lumina Imaging system. Mice were given NIR dye (IR783) 48 h before euthanasia, the tumor specific NIR dye was used to detect metastatic tumor in the mice.

Statistical Analysis

Values were expressed as means±standard deviation. All experiments were done in triplicates at least two independent times. Statistical analysis was performed using Student's t-test or ANOVA. Values of p<0.05 were considered to be statistically significant.

Generation of Non-Integrating Human iPSCs Using Episomal Plasmids

Apparently healthy human fibroblast cell lines (GM05400, 03814 and 02183) were obtained from the Coriell Institute for Medical Research, under their consent and privacy guidelines. All protocols were performed in accordance with the institutional review board's guidelines at the Cedars-Sinai Medical Center under the auspice IRB-SCRO Protocols, Pro00021505 and Pro00032834. Limbal epithelial stem cell-enriched cultures were prepared from discarded donor corneoscleral rims (01CNL) provided by Drs. Rabinowitz and Maguen within 24 hrs after corneal transplantation, under an approved Cedars-Sinai Medical Center IRB protocol Pro00019393. Cells were isolated by the standard dispase method. Upon iPSC generation at Cedars Sinai, they were renamed 00iCTR-n2, 14iCTR-n6, 83iCTR-n1, and 01iCNL-n1 to reflect catalog or identification numbers, control line and clone number (Luong, et al. 2011; Sareen, et al. 2012). Fibroblasts or limbal cells were reprogrammed into virus-free iPSC lines using the Amaxa Human Dermal Fibroblast Nucleofector Kit to express episomal plasmids with 6 factors: OCT4, SOX2, KLF4, L-MYC, LIN28, and p53 shRNA (Addgene) (Okita, et al. 2011). This method has a significant advantage over viral transduction, because exogenously introduced genes do not integrate and are instead expressed episomally in a transient fashion. Briefly, fibroblasts (0.8×10$^6$ cells per nucleofection) were harvested, centrifuged at 200 g for 5 minutes, re-suspended carefully in Nucleofector® Solution (VPD-1001, Lonza) and the U-023 program was applied. All cultures were maintained under norm-oxygen conditions (5% O$_2$) during reprogramming, which further enhance the efficiency of iPSC generation. The media was kept on for 48 hours and gradually changed to chemically-defined mTeSR®1 medium containing small molecules to enhance reprogramming efficiency. The small molecules used were, (1) sodium butyrate (0.5 mM; Sigma-Aldrich), (2) glycogen synthase kinase 3β inhibitor of the Wnt/β-catenin signaling pathway (CHIR99021, 3 μM; Tocris Bioscience/R&D Systems, Minneapolis, Minn.), (3) MEK pathway inhibitor (PD 0325901, 0.5 μM; Stemgent, Cambridge, Mass.), (4) Selective inhibitor of TGF-β type I receptor ALK5 kinase, type I activin/nodal receptor ALK4 and type I nodal receptor ALK7 (A 83-01, 0.5 μM; (Tocris Bioscience). Colonies with ES/iPSC-like morphology appeared 25-31 days later. Subsequently, colonies with the best morphology were transferred onto a feeder-independent BD Matrigel™ Matrix and maintained in mTeSR®1 medium (Ludwig, et al. 2006).

Human Embryonic Stem Cell (ESC) and iPSC Cell Culture

Human ESC line, H9 (WiCell, Madison, Wis.) and iPSC lines were maintained onto a feeder-independent BD Matrigel™ Matrix and maintained in mTeSR®1 medium. Colonies grown on growth factor-reduced Matrigel (BD Biosciences, San Jose, Calif.) had typical ESC-like morphology with well-defined borders, and high nuclear/cytoplasmic ratio. The iPSC clones were further expanded and cryopreserved according to previously published protocols (Ludwig et al. 2006; Yu, et al. 2007).

Human iPSC Characterization

Human iPSCs were rigorously characterized at the Cedars-Sinai iPSC core using several assays. G-Band karyotyping (see below) ensured normal a karyotype, and genomic DNA PCR confirmed the absence of episomal plasmid genes, as previously described (Muller, et al. 2011;

Okita et al. 2011; Sareen et al. 2012). Pluripotency was assessed by immunostaining with surface and nuclear pluripotency markers for subsequent flow cytometry quantification (>80% SSEA4 and Oct3/4 double positivity), by quantitative RT-PCR of endogenous pluripotency genes, and by gene-chip and bioinformatics-based PluriTest assays. Spontaneous embryoid body differentiation confirmed the capacity to form all germ layers. Characterization of iPSC lines used in this study has been previously published (Sareen et al. 2012; Sareen, et al. 2013).

Example 6—Results miR-154* and miR-379 of the DLK1-DIO3 Cluster are Overexpressed in Bone Metastatic EMT Models of Human PCa We determined the levels of miR-154/154* and miR-379 in two bone metastatic models of PCa, ARCaP and LNCaP. Mesenchymal-type $ARCaP_M$ cells upon intracardiac inoculation or orthotopic implantation of these cells have 100% bone metastatic capability compared to its isogenic epithelial-type counterpart $ARCaP_E$ cells. Similarly, C4-2 PCa cells have a high metastatic ability compared to their lineage related LNCaP cells. Both miR-154* and miR-379 were elevated in $ARCaP_M$ cells when compared to $ARCaP_E$ cells, and in C4-2 cells compared to LNCaP cells (FIG. 11A). We determined the expression of miR-154* in intratibial prostate cancer bone metastasis tissues by ISH-QD and observed higher expression in the metastatic prostate cancer cells (FIG. 11B). Previous studies demonstrate that several members of the DLK1-DIO3 miRNA cluster are elevated in human embryonic stem cells and induced pluripotent cells (iPSCs). We measured the relative levels of these miRNAs in H9 embryonic stem cells and in iPSCs. Both H9 human embryonic stem cells and patient derived iPS cells had elevated expression of miR-154* (FIGS. 11C and 11D) but not miR-379. We previously demonstrated that one of the predominant signaling pathways activated in PCa bone metastasis is the β2-microglobulin/HFE pathways. Inhibition of either of these proteins results in reversal of EMT. We observed that $ARCaP_M$ HFE knockdown cells ($ARCaP_M$ $KD^{HFE1}$ cells) had significantly decreased expression of miR-154* and miR-379 similar to the epithelial $ARCaP_E$ PCa cells (FIG. 11E). Additionally, other members, such as miR-409-3p/-5p of the DLK1-DIO3 cluster were also decreased in $ARCaP_M$ HFE knockdown cells. These data together demonstrate that miR-154* and miR-379 are elevated in PCa EMT and bone metastatic models.

Inhibition of miR-154* or miR-379 Results in Reversal of EMT (MET) of PCa Cells

Figure 12:
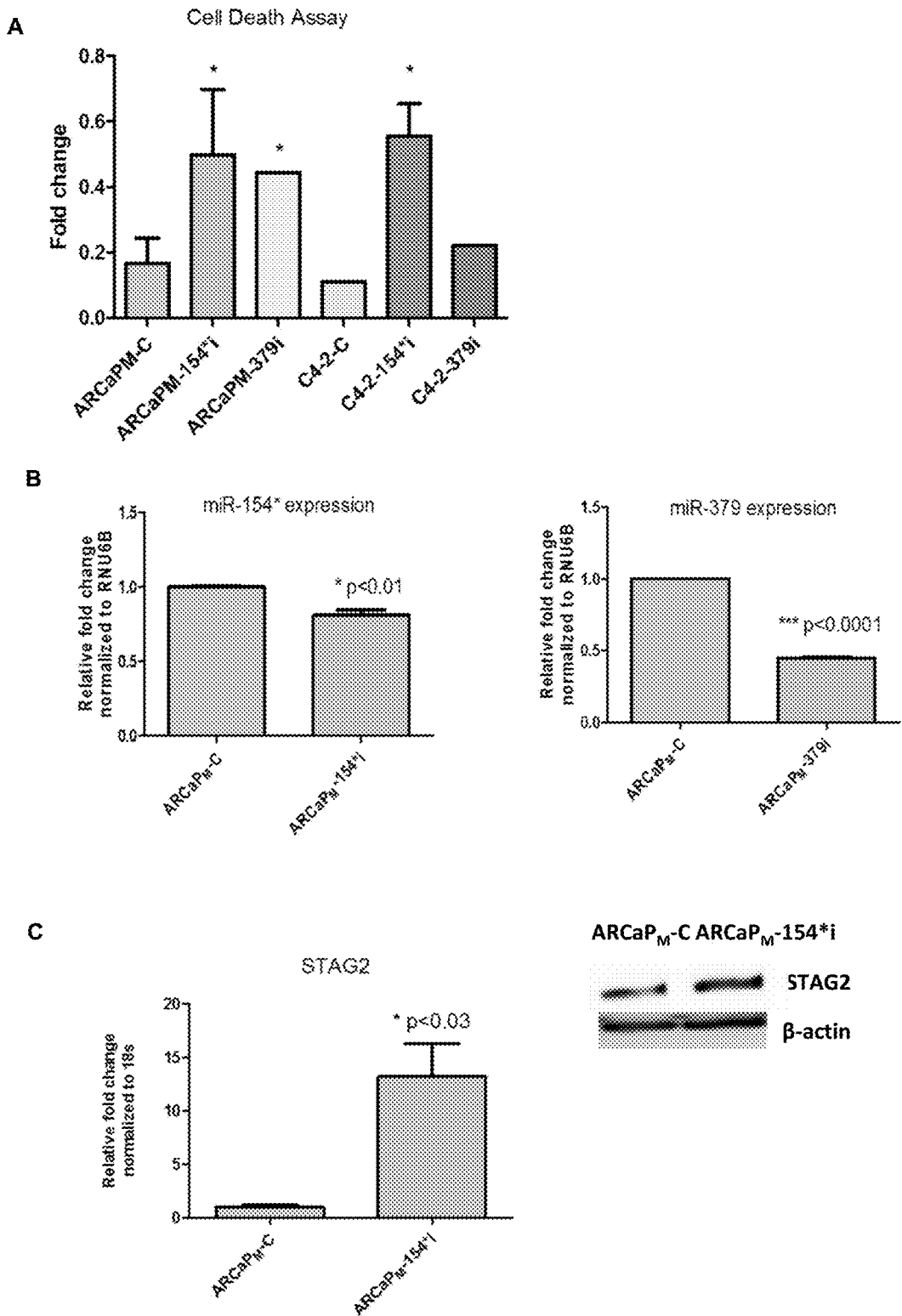
FIG. 12 shows that inhibition of miR-154* or miR-379 results in mesenchymal to epithelial transition of PCa cells. (A) Cell death in ARCaP$_M$ PCa cells in response to a miR-154* and miR-379 inhibitor using trypan blue exclusion assay. (B) Expression of miR-154* and miR-379 assayed by qRT-PCR in ARCaP$_M$-C control PCa cells and ARCaP$_M$-154*i (miR-154* inhibitor transfected cells) and ARCaP$_M$-379i (miR-379 inhibitor) transfected cells. Data is normalized to RNU6B. (C) STAG2 (mir-154* target) protein and mRNA expression in ARCaP$_M$-C and ARCaP$_M$-154*i PCa cells assayed by western analysis and qRT-PCR. (D) 3'UTR binding luciferase assay using wild type (WT) and mutant 3'UTR (STAG2) construct and miR-154* mimics in 293T cells. (E) Morphological changes in ARCaP$_M$-154*i and ARCaP$_M$-379i compared to ARCaP$_M$-C control PCa cells. (F) E-cadherin mRNA assayed in ARCaP$_M$-C, ARCaP$_M$-154*i and ARCaP$_M$-379i expressing PCa cells by qRT-PCR, normalized to 18s RNA. (G) Invasion assay of in ARCaP$_M$-C, ARCaP$_M$-154*i and ARCaP$_M$-379i expressing PCa cells. *: p<0.05 were considered to be statistically significant by t-test or ANOVA-Tukey test.
Figure 12:
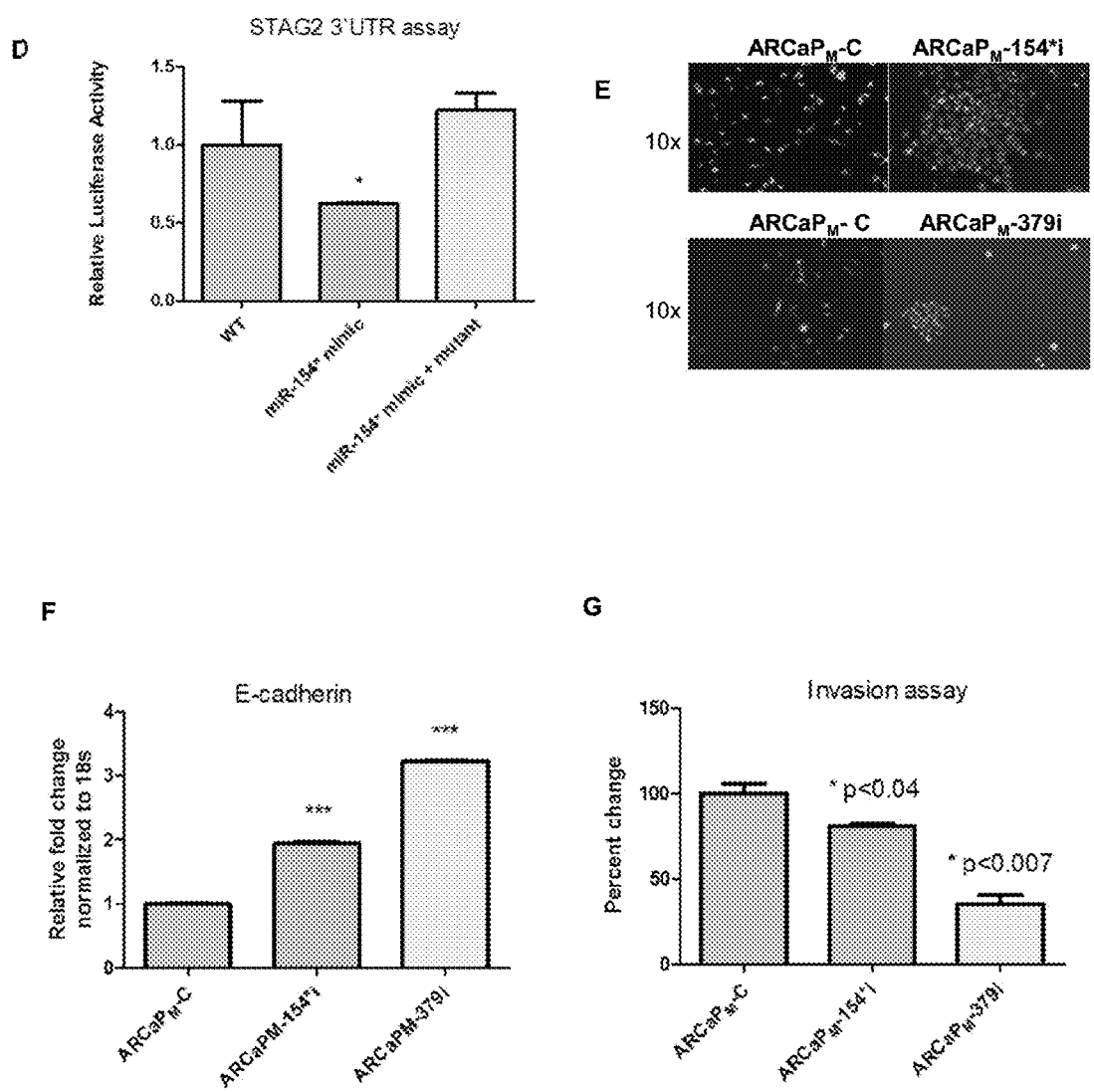

To test the hypothesis whether miR-154* and miR-379 is involved in PCa EMT, we transiently depleted miR-154* and miR-379 in $ARCaP_M$ and C4-2 cells using siRNA and determined the cell viability by the trypan blue exclusion test. Both miR-154* knockdown cells and miR-379 inhibited cells underwent increased cell death compared to control transfected cells in both of the PCa cell line models studied (FIG. 12A). Next, we introduced a shRNA in the mesenchymal-type $ARCaP_M$ PCa cells to generate miR-154* knockdown ($ARCaP_M$-154*i) or miR-379 knockdown ($ARCaP_M$-379i) cells. In addition we used a scrambled shRNA to generate a control shRNA vector ($ARCaP_M$-C). Reduced expression of miR-154* was detected in the $ARCaP_M$-154*i cells by qRT-PCR analysis compared to the shRNA control vector $ARCaP_M$-C. Reduced expression of miR-379 was also observed in the $ARCaP_M$-379i cells by qPCR analysis compared to the $ARCaP_M$-C cells (FIG. 12B). RNU6B was used for normalization. The miR-154* target gene, stromal antigen 2 (STAG2) was measured in the knockdown cells (TargetScan v6.2). STAG2 is a tumor suppressor protein. The mRNA and protein expression of STAG2 was increased in the $ARCaP_M$-154*i cells compared to the control $ARCaP_M$ cells (FIG. 12C). We further tested if miR-154* directly binds to the 3'UTR of STAG2 using a luciferase reporter assay. Compared to control miRNA treated cells, miR-154* mimic-treated cells had reduced basal luciferase activity (FIG. 12D). We mutated the 3'UTR of STAG2 at the miR-154* binding site and demonstrate restoration of luciferase activity in response to the miR-154* mimic (FIG. 12D). Interestingly, inhibition of miR-154* or miR-379 led to reversion of mesenchymal $ARCaP_M$ cells to an epithelial phenotype (FIG. 12E) accompanied by increases in E-cadherin mRNA expression in $ARCaP_M$-154*i and $ARCaP_M$-379i cells but not in $ARCaP_M$-C cells (FIG. 12F). To determine if functional reversal of EMT (MET) occurred in addition to morphological changes, we performed invasion assays on these cell lines. $ARCaP_M$-154*i and $ARCaP_M$-379i cells had significantly decreased invasive capacity compared to $ARCaP_M$-C cells (FIG. 12G). Taken together, these results demonstrate that miR-154* and miR-379 play an important role in EMT and invasive capacity of PCa cells.

Figure 13:
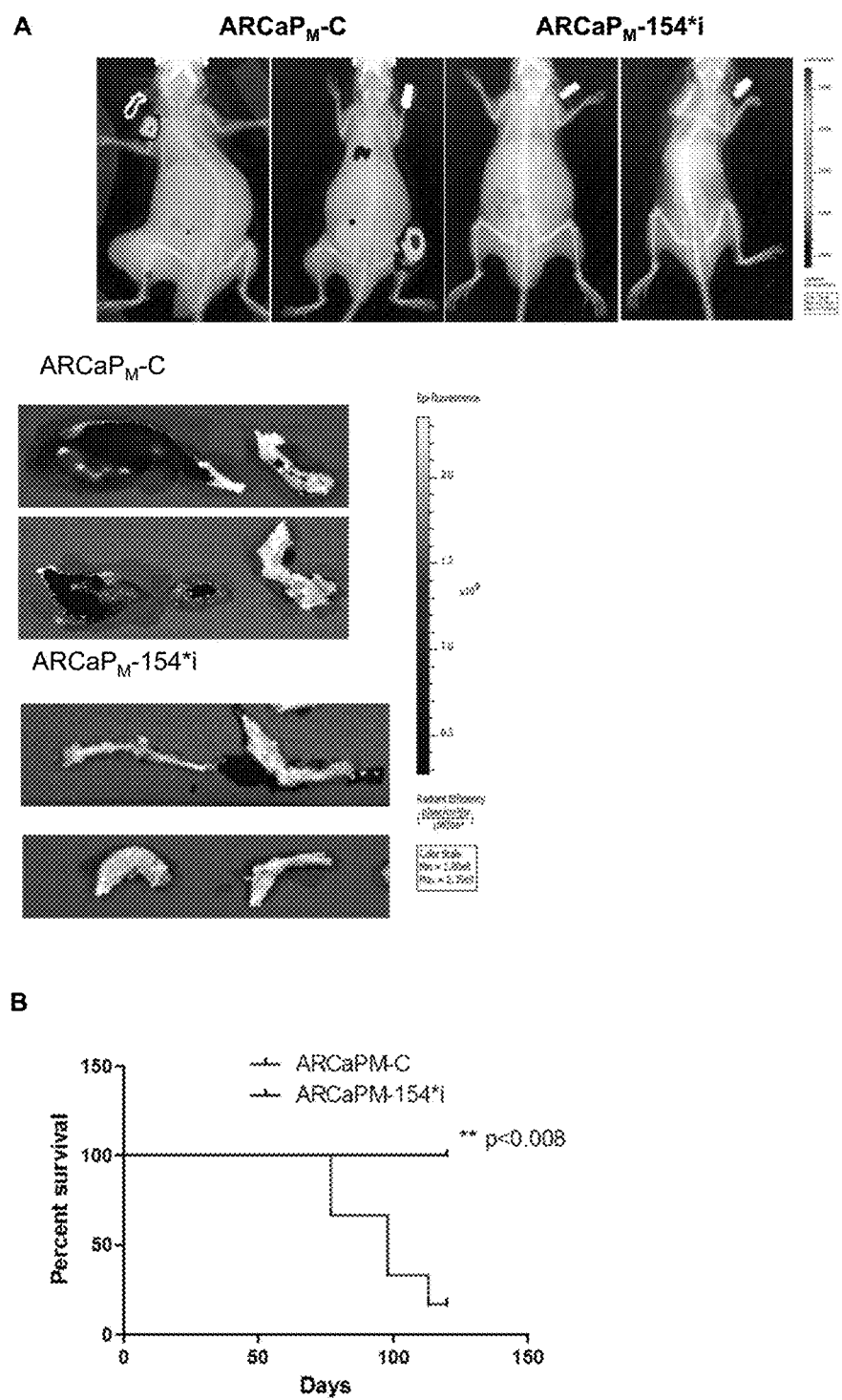
FIG. 13 depicts inhibition of miR-154* results in decreased metastasis of bone and soft tissue of PCa cells. (A) Representative metastatic lesions observed by X-ray/luciferase imaging of tumors of ARCaP$_M$-C cells and ARCaP$_M$-154*i cells in SCID/Beige mice (n=5) following intra-cardial injections. Images of bone with tumor in the ARCaP$_M$-C cells and ARCaP$_M$-154*i injected mice using near infra-red dye (IR783). (B) Kaplan Meier's curve of ARCaP$_M$-C cells (bottome line) and ARCaP$_M$-154*i (top line) injected SCID/Beige mice. (C) miR-154* expression in PCa clinical samples from BPH, Gleason 6 and 7 tissues assayed by ISH-QD labeling. Data plotted as an intensity counts/cell in tissues. Representative image of Gleason 7 tissue with miR-154* staining in red (magnification 40×). Nuclei stained by DAPI. (D) Kaplan-Meier disease free survival (DFS) curves for the PCa patients, based on miR-379 expression in the MSKCC dataset. The y-axis is disease free survival probability, and the x-axis is survival in months. Top line represents the DFS of patients with miR-379 lower than the median of the normal individuals (n=78). Bottom line represents the DFS of patients with miR-379 higher than the median of the normal individuals (n=29). Data was analyzed using log-rank test (p=0.0117). (E) miR-154 expression in normal, primary and metastatic PCa patients. Significant differential expression of miR-154 was noted between normal individual (n=29), primary (n=99) (p<0.001) and metastatic (n=14) (p=0.035) PCa patients. *: p<0.05 were considered to be statistically significant.
Figure 13:
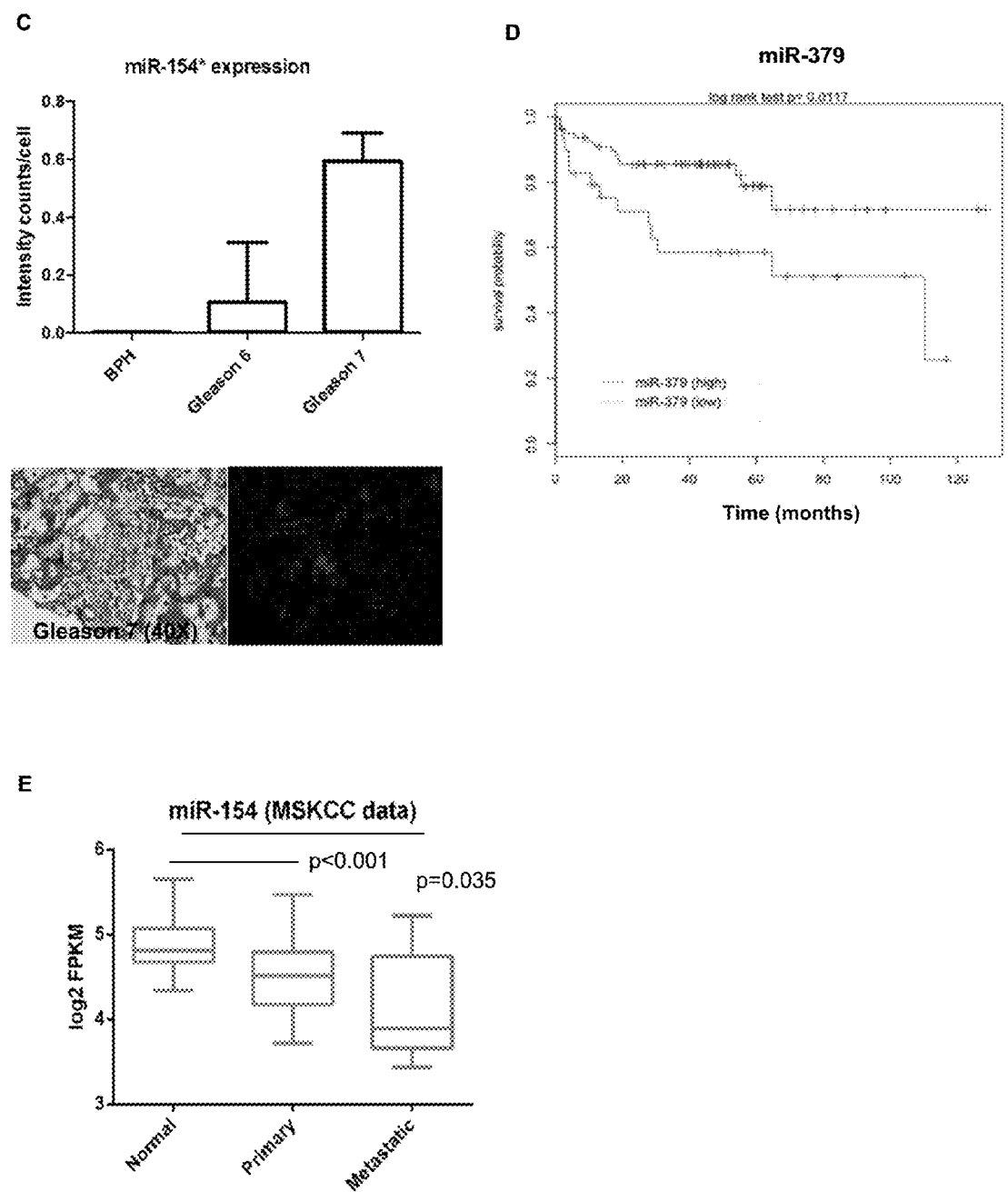

Inhibition of miR-154* Results in Decreased Bone and Soft Tissue Metastasis of PCa Cells Cancer cells gain their metastatic potential by undergoing EMT. Previous studies from our laboratory using the ARCaP model demonstrate the close association between EMT and PCa bone metastasis. Since miR-154* levels are elevated in metastatic cancer cells, we determined if inhibition of miR-154* would lead to decreased metastasis in vivo. Consistent with our hypothesis, we show that inhibition of miR-154* resulted in increased cell death, mesenchymal to epithelial transition (MET) and decreased invasion in vitro. To determine if miR-154* plays a role in cancer metastasis in vivo, we inoculated luciferase-tagged $ARCaP_M$-C control cells or $ARCaP_M$-154*i (miR-154* inhibited) cells via the intracardiac route into SCID/Beige mice (N=5/group) to mimic in vivo metastasis. Tumor growth was monitored by luciferase imaging. Mice that received $ARCaP_M$-154*i cells had a significantly decreased incidence of metastasis (0/5) compared to mice that received $ARCaP_M$-C control cells (4/5) at 15 weeks post-inoculation. X-ray and luciferase imaging of representative mice from both groups are shown in FIG. 13A. The tumors were detected by IR783 (near infrared dye) in all mice (FIG. 13A). The control mice developed metastatic tumors at 1-5 sites in the body, while $ARCaP_M$-154*i injected mice did not develop any tumors. Bone tumors sites included the tibia, femur, humerus and mandible, and had mixed osteoblastic and osteolytic lesions. Mice inoculated with $ARCaP_M$-C control cells had decreased survival compared to those inoculated with $ARCaP_M$-154*i cells as shown in the Kaplan Meier survival curve (FIG. 13B). Taken together, these studies demonstrate that miR-154* is essential for the development of bone metastasis of human PCa cells and that knockdown of miR-154* reduces bone metastasis and increases the survival of mice.

Elevated Expression of miR-154* and miR-379 in Human PCa Clinical Samples

Figure 17:
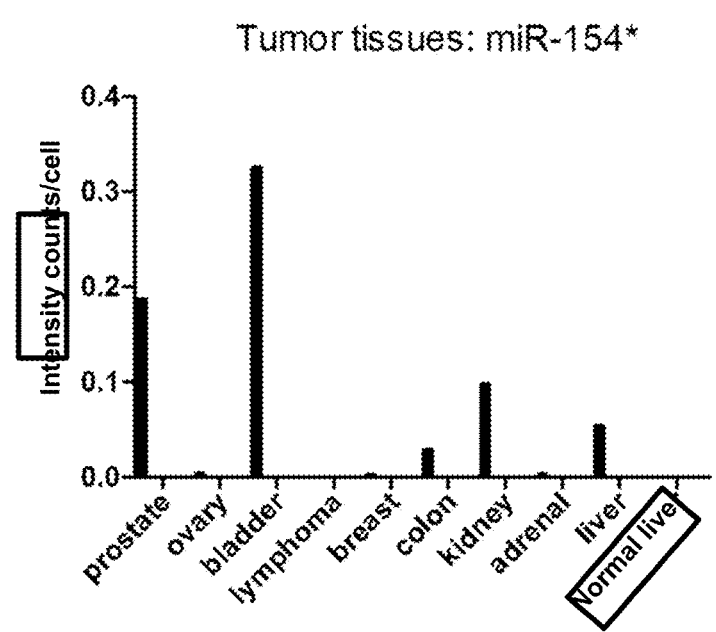
FIG. 17 depicts miR-154* staining of different human cancer tissues using ISH-QD labeling. Values are represented as intensity counts/cell, (n=1, duplicate samples from the same patient tumor tissues were stained).

We next determined the expression of miR-154* in human PCa tissues using in situ hybridization and quantum dots analysis. miR-154* probes were biotin-labeled (Exiqon) and further labeled to a streptavidin conjugated QD at a specified wavelength. The tissues were separated into three groups, benign prostatic hyperplasia (BPH) (N=4), Gleason 6 (N=12) and Gleason 7 (N=7). Each tissue sample has two sections. Tumor tissues had higher staining of miR-154* compared to BPH, but was not significantly different (FIG. 13C). A representative image Gleason 7 demonstrates higher staining in the tumor tissues (FIG. 13C). We also determined the expression of miR-154* in other cancers and found an increased expression in other urological cancers (FIG. 17). Using the publicly available database (MSKCC), we demonstrate that elevated expression of miR-379 is associated with progression free survival and miR-154 (the opposite strand of miR-154*) is downregulated in both primary and metastatic PCa tissues as compared with normal individuals (FIGS. 13D & E). These results are consistent with previous studies demonstrating that miR-154 is decrease in prostate cancer cell lines and clinical samples. These databases did not have information on miR-154*. Nevertheless, our observations in bone metastatic PCa cell line models are clinically relevant and our experimental observations correlated with tumor progression. These results collectively demonstrate that miR-154* and miR-379 are highly expressed in PCa and correlate with progression free survival in patients.

Figure 14:
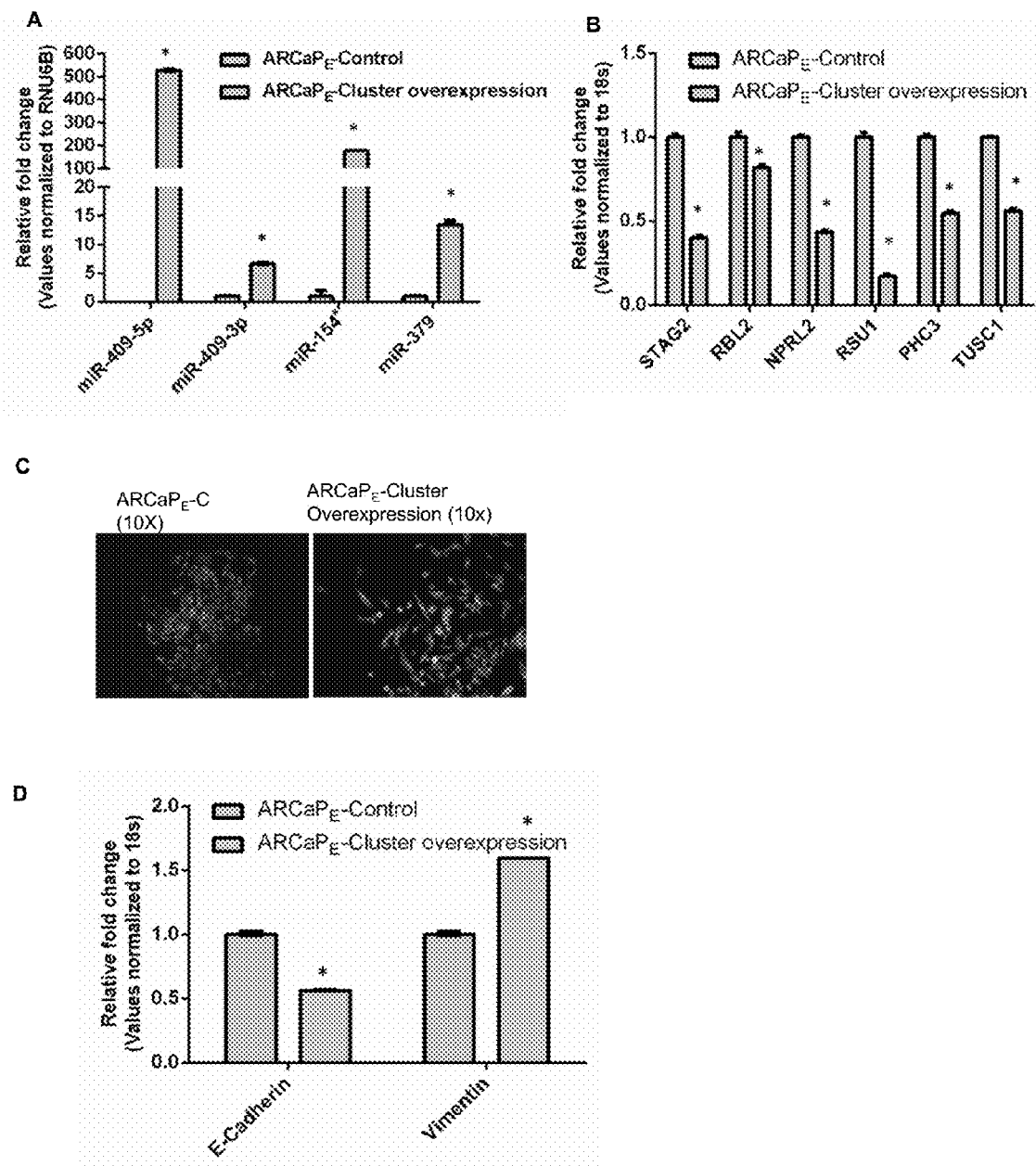
FIG. 14 depicts overexpression of miR-154*, miR-409-3p/-5p and miR-379 induces EMT in PCa cells (A) Expression of miR-409-5p/-3p, miR-154* and miR-379 assayed by real time PCR in ARCaP$_E$-C control PCa cells (left columns) and ARCaP$_E$-cluster overexpressing cells normalized to RNU6B (right columns). (B) RNA expression of miR-409-5p/-3p and miR-154* targets in ARCaP$_M$ PCa cells assayed by qRT-PCR. (miR-154* mRNA targets: STAG2, miR-409-5p mRNA targets: STAG2, RBL2, NPRL2 and RSU1, miR-409-3p mRNA targets: RSU1, PHC3 and TUSC1) (control, left columns; overexpressing, right columns). (C) Morphological EMT changes in ARCaP$_E$-C control PCa cells and ARCaP$_E$-cluster overexpressing cells; magnification 10× (D) RNA expression of EMT markers, E-cadherin and vimentin in ARCaP$_E$-C control PCa cells (left columns) and ARCaP$_E$-cluster overexpressing cells (right columns) assayed by qRT-PCR. *: p<0.05 were considered to be statistically significant by t-test.
Figure 16:
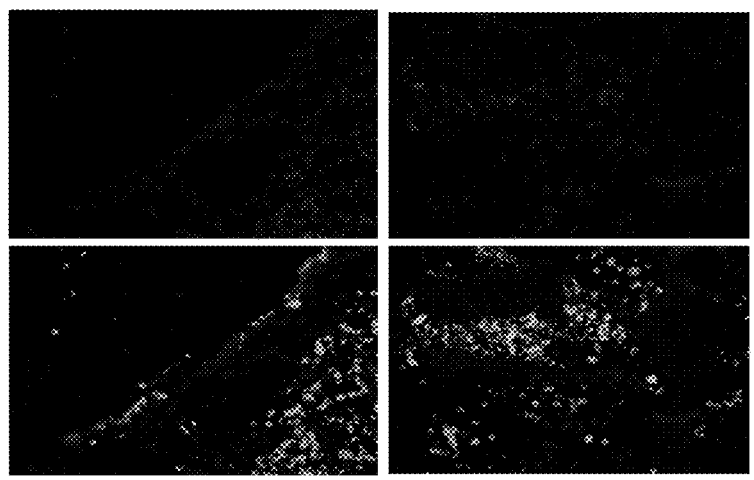
FIG. 16 depicts miR-154* (red), miR-409-3p (green) and miR-409-5p (green) staining of human prostate bone metastatic tissue using multiplexed ISH-QD labeling. Two human prostate bone metastatic tissues were used, and multiplexed for probes against miR-154* and miR-409-3p or miR-409-5p.

Overexpression of miRNA Members of the DLK1-DIO3 Cluster Promotes EMT in PCa Cells Previously published studies by our lab demonstrate that miR-409-3p/5p, two key miRNAs in the DLK1-DIO3 cluster are elevated in PCa cells. Since all four members (miR-409-3p/5p, miR-154* and miR-379) of the DLK1-DIO3 cluster are elevated in PCa bone metastatic cells, we stably transduced ARCaP$_E$ cells, a marginally metastatic epithelial cell line using a lentivirus that carries a GFP control vector (ARCaP$_E$-C) or a lentiviral overexpression vector that carries GFP and a combination of all four miRNAs-miR-409-3p, -5p, miR-154* and miR-379 (AR-CaP$_E$-cluster overexpression). The miRNA expression of the members of the DLK1-DIO3 cluster was determined using qRT-PCR assay (FIG. 14A). In the ARCaP$_E$-cluster overexpression cells, miR-409-5p and miR-154* were highly expressed followed by moderate expression of miR-379 and miR-409-3p when compared to ARCaP$_E$-C PCa cells (FIG. 14A). Next, we measured the expression levels of the target genes of these miRNAs by qRT-PCR. Several of the target genes of these four miRNAs include tumor suppressors that are shared by these miRNAs (Prediction software: Targetscan v6.2 Jun. 2012 and Pictar). Overexpression of these miRNAs resulted in a decrease in mRNA levels of several of the target genes that are commonly shared by these miRNAs. STAG2 (target gene of miR-154* and miR-409-5p) and Ras suppressor protein 1 (RSU1) (target gene of miR-409-3p and miR-409-5p) were significantly decreased in the ARCaP$_E$-cluster overexpression cells compared to control (FIG. 4B). miR-409-5p targets including STAG2, retinoblastoma-like 2 (RBL2), Nitrogen permease regulator-like 2 (NPRL2) and RSU1 were decreased in the cluster overexpression cells (FIG. 4B). Targets of miR-409-3p including RSU1, polyhomeotic homolog 3 (PHC3) and tumor suppressor candidate 1 (TUSC1) were decreased in cluster overexpression cells (FIG. 14B). These results demonstrate that overexpression of miRNA members of the DLK1-DIO3 microRNA mega-cluster results in decreased expression of several tumor suppressor genes. We also observed EMT changes in ARCaP$_E$-cluster overexpression PCa cells. The cells appeared spindle shaped and had decreased expression of E-cadherin and increased expression of vimentin compared to ARCaP$_E$-C cells (FIG. 14C). Analyses of the target pathways regulated by these miRNAs include oncogenic pathways such as E2F signaling, the Ras pathway, hypoxia inducible factor signaling, as well as the WNT and transforming growth factor-β (TGF-β) pathways. These pathways also activate EMT and the cancer stem cell phenotype (FIG. 15). miR-154* targets STAG2 and SMAD7. STAG2 is known to induce aneuploidy. SMAD7 is an inhibitor of the TGF-β pathway. miR-379 is predicted to inhibit forkhead box F2 (FOXF2) which has been shown to inhibit the WNT pathway in colon cancer development. We previously demonstrated that miR-409-3p and miR-409-5p inhibit RSU1, which is a known inhibitor of the oncogenic Ras pathway. Other targets of miR-409-3p include von hippel-lindau tumor suppressor, E3 ubiquitin protein ligase (VHL) and PHC3. VHL is a tumor suppressor and degrades HIF-1α, inhibition of VHL results in the stabilization of HIF-1α, which is known to induce resistance to radiation and chemotherapeutic agents. PHC3 is a tumor suppressor protein and is lost in osteosarcoma. PHC3 and Ephrin receptors have been predicted to interact though protein-protein interactions (www.biograph.be/). miR-409-5p has been shown to target STAG2, RSU1, NPRL2 and RBL2. NPRL2 activates AKT pathway and RBL2 activates the E2F pathway. Thus, these miRNA activate oncogenic proteins by targeting tumor suppressors. Since these miRNAs are elevated in PCa bone metastatic models, we determined the levels of these miRNAs in human PCa bone metastatic samples using multiplexed ISH-QD labeling. We observed increased miR-154*, miR-409-3p and miR-409-5p staining in human metastatic tumor tissues in the bone (FIG. 16). Taken together, these results demonstrate that miR-154*, miR-409-3p/-5p and miR-379 induce EMT in PCa cells, show upregulated expression in human PCa bone metastasis tissues and correlate with progression free survival in PCa patients.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method, comprising:

providing a miRNA inhibitor; and administering the miRNA inhibitor to a subject in need of treatment for cancer, in need of treatment for cancer metastasis, or in need of lowering or treatment for cancer drug resistance to treat cancer, to treat cancer metastasis, or to lower or treat cancer drug resistance, wherein the cancer is prostate cancer metastasis to the bone or metastatic prostate cancer, and wherein the miRNA inhibitor is an shRNA or siRNA capable of inhibiting miR-409-3p and/or mature miR-409-3p.

2. The method of claim 1, further comprising administering to the subject radiation treatment or chemotherapy treatment.

3. The method of claim 1, wherein the miRNA inhibitor is a shRNA directed against a mature miRNA, wherein the miRNA is miR-409-3p.

4. The method of claim 1, wherein the miRNA inhibitor is a siRNA directed against a mature miRNA, wherein the miRNA is miR-409-3p.

5. The method of claim 1, wherein the miRNA inhibitor is encoded by a polynucleotide as disclosed by SEQ ID NO:23 and administering comprises administering the polynucleotide.

6. The method of claim 1, wherein the miRNA inhibitor is a shRNA or a siRNA capable of interfering the expression of SEQ ID NO:9.

7. The method of claim 1, wherein the cancer is prostate cancer metastasis to the bone.

8. The method of claim 1, wherein the cancer is metastatic prostate cancer.

* * * * *

SEQUENCE LISTING

<160> NUMBER OF SEQ ID NOS: 32

<210> SEQ ID NO 1
<211> LENGTH: 71
<212> TYPE: DNA
<213> ORGANISM: Artificial Sequence
<220> FEATURE:
<223> OTHER INFORMATION: homo sapiens

<400> SEQUENCE: 1
ggatccgtgg tagattatgg aacataagct tcctgtcagc ctacgttcca tagtctacca    60
tttttgaatt c                                                        71

<210> SEQ ID NO 2
<211> LENGTH: 21
<212> TYPE: RNA
<213> ORGANISM: Homo sapiens

<400> SEQUENCE: 2
ugguagacua uggaacguag g                                             21

<210> SEQ ID NO 3
<211> LENGTH: 22
<212> TYPE: RNA
<213> ORGANISM: Homo sapiens

<400> SEQUENCE: 3
uauguaacau gguccacuaa cu                                            22

<210> SEQ ID NO 4
<211> LENGTH: 73
<212> TYPE: DNA
<213> ORGANISM: Artificial Sequence
<220> FEATURE:
<223> OTHER INFORMATION: homo sapiens

<400> SEQUENCE: 4
ggatccgaac tggcactcaa agtcacgatc ttcctgtcag agcgggactt tgagggccag    60 ttttttgaa ttc                                                       73

<210> SEQ ID NO 5
<211> LENGTH: 22
<212> TYPE: RNA
<213> ORGANISM: Homo sapiens

<400> SEQUENCE: 5
aacuggcccu caaagucccg cu                                            22

<210> SEQ ID NO 6
<211> LENGTH: 22
<212> TYPE: RNA
<213> ORGANISM: Homo sapiens

<400> SEQUENCE: 6
cggggutuug agggcgagau ga                                            22

<210> SEQ ID NO 7
<211> LENGTH: 73
<212> TYPE: DNA
<213> ORGANISM: Artificial Sequence
<220> FEATURE:
<223> OTHER INFORMATION: homo sapiens

<400> SEQUENCE: 7

```
ggatccgagg ttaccagagc aactttgcac ttcctgtcag tgcaaagttg ctcgggtaac    60
cttttttgaa ttc                                                      73

<210> SEQ ID NO 8
<211> LENGTH: 23
<212> TYPE: RNA
<213> ORGANISM: Homo sapiens

<400> SEQUENCE: 8
agguuacccg agcaacuuug cau                                           23

<210> SEQ ID NO 9
<211> LENGTH: 22
<212> TYPE: RNA
<213> ORGANISM: Homo sapiens

<400> SEQUENCE: 9
gaauguugcu cggugaaccc cu                                            22

<210> SEQ ID NO 10
<211> LENGTH: 73
<212> TYPE: DNA
<213> ORGANISM: Artificial Sequence
<220> FEATURE:
<223> OTHER INFORMATION: homo sapiens

<400> SEQUENCE: 10
ggatccgtag gttacccgtg ttgcattagc ttcctgtcag cgaaggcaac acggataacc    60
tatttttgaa ttc                                                      73

<210> SEQ ID NO 11
<211> LENGTH: 22
<212> TYPE: RNA
<213> ORGANISM: Homo sapiens

<400> SEQUENCE: 11
uagguuaucc guguugccuu cg                                            22

<210> SEQ ID NO 12
<211> LENGTH: 22
<212> TYPE: RNA
<213> ORGANISM: Homo sapiens

<400> SEQUENCE: 12
aaucauacac gguugaccua uu                                            22

<210> SEQ ID NO 13
<211> LENGTH: 25
<212> TYPE: DNA
<213> ORGANISM: Artificial Sequence
<220> FEATURE:
<223> OTHER INFORMATION: synthetic construct

<400> SEQUENCE: 13
cgcctacgtt ccatagtcta ccatc                                         25

<210> SEQ ID NO 14
<211> LENGTH: 25
<212> TYPE: DNA
<213> ORGANISM: Artificial Sequence
<220> FEATURE:
<223> OTHER INFORMATION: synthetic construct
```

```
<400> SEQUENCE: 14
gggttcaccg agcaacattc gtcgt                                          25

<210> SEQ ID NO 15
<211> LENGTH: 25
<212> TYPE: DNA
<213> ORGANISM: Artificial Sequence
<220> FEATURE:
<223> OTHER INFORMATION: synthetic construct

<400> SEQUENCE: 15
agcgaaggca acacggataa cctat                                          25

<210> SEQ ID NO 16
<211> LENGTH: 21
<212> TYPE: DNA
<213> ORGANISM: Homo sapiens

<400> SEQUENCE: 16
tggtagacta tggaacgtag g                                              21

<210> SEQ ID NO 17
<211> LENGTH: 22
<212> TYPE: DNA
<213> ORGANISM: Homo sapiens

<400> SEQUENCE: 17
aactggccct caaagtcccg ct                                             22

<210> SEQ ID NO 18
<211> LENGTH: 23
<212> TYPE: DNA
<213> ORGANISM: Homo sapiens

<400> SEQUENCE: 18
aggttacccg agcaactttg cat                                            23

<210> SEQ ID NO 19
<211> LENGTH: 22
<212> TYPE: DNA
<213> ORGANISM: Homo sapiens

<400> SEQUENCE: 19
aatcatacac ggttgaccta tt                                             22

<210> SEQ ID NO 20
<211> LENGTH: 67
<212> TYPE: DNA
<213> ORGANISM: Artificial Sequence
<220> FEATURE:
<223> OTHER INFORMATION: homo sapiens

<400> SEQUENCE: 20
gatccgaatc atacacagtt gacctcttct tcctgtcaga ataggtcaac cgtgtatgat    60
tttttttg                                                             67

<210> SEQ ID NO 21
<211> LENGTH: 67
<212> TYPE: DNA
<213> ORGANISM: Artificial Sequence
<220> FEATURE:
<223> OTHER INFORMATION: homo sapiens

<400> SEQUENCE: 21
```

```
aattcaaaaa aatcatacac ggttgaccta ttctgacagg aagaagaggt caactgtgta    60
tgattcg                                                              67

<210> SEQ ID NO 22
<211> LENGTH: 22
<212> TYPE: DNA
<213> ORGANISM: Homo sapiens

<400> SEQUENCE: 22
gaatgttgct cggtgaaccc ct                                             22

<210> SEQ ID NO 23
<211> LENGTH: 67
<212> TYPE: DNA
<213> ORGANISM: Artificial Sequence
<220> FEATURE:
<223> OTHER INFORMATION: homo sapiens

<400> SEQUENCE: 23
gatccggaat gttgctcagt gaacctctct tcctgtcaga ggggttcacc gagcaacatt    60
cttttttg                                                             67

<210> SEQ ID NO 24
<211> LENGTH: 67
<212> TYPE: DNA
<213> ORGANISM: Artificial Sequence
<220> FEATURE:
<223> OTHER INFORMATION: homo sapiens

<400> SEQUENCE: 24
aattcaaaaa gaatgttgct cggtgaaccc ctctgacagg aagagaggtt cactgagcaa    60
cattccg                                                              67

<210> SEQ ID NO 25
<211> LENGTH: 63
<212> TYPE: DNA
<213> ORGANISM: Artificial Sequence
<220> FEATURE:
<223> OTHER INFORMATION: primer

<400> SEQUENCE: 25
gttaacagtg acatttaaat ggggacatga ttttaattat cttttgata ataagcaacc     60 ttg                                                                  63

<210> SEQ ID NO 26
<211> LENGTH: 63
<212> TYPE: DNA
<213> ORGANISM: Artificial Sequence
<220> FEATURE:
<223> OTHER INFORMATION: primer

<400> SEQUENCE: 26
caaggttgct tattatcaaa agaataatta aaatcatgtc cccatttaaa tgtcactgtt    60
aac                                                                  63

<210> SEQ ID NO 27
<211> LENGTH: 60
<212> TYPE: DNA
<213> ORGANISM: Artificial Sequence
<220> FEATURE:
<223> OTHER INFORMATION: primer
```

```
<400> SEQUENCE: 27
aactagaact gctgagagga ctgtatatac aattttaaac ctaagttgat ttttttctc    60

<210> SEQ ID NO 28
<211> LENGTH: 60
<212> TYPE: DNA
<213> ORGANISM: Artificial Sequence
<220> FEATURE:
<223> OTHER INFORMATION: primer

<400> SEQUENCE: 28
gagaaaaaaa atcaacttag gtttaaaatt gtatatacag tcctctcagc agttctagtt    60

<210> SEQ ID NO 29
<211> LENGTH: 23
<212> TYPE: RNA
<213> ORGANISM: Homo sapiens

<400> SEQUENCE: 29
aauaauuaaa aucauguaac cau                                           23

<210> SEQ ID NO 30
<211> LENGTH: 23
<212> TYPE: RNA
<213> ORGANISM: Homo sapiens

<400> SEQUENCE: 30
uacguuucaa cgagcccauu gga                                           23

<210> SEQ ID NO 31
<211> LENGTH: 23
<212> TYPE: RNA
<213> ORGANISM: Homo sapiens

<400> SEQUENCE: 31
uccauuuguu ucuuuaacau uac                                           23

<210> SEQ ID NO 32
<211> LENGTH: 22
<212> TYPE: RNA
<213> ORGANISM: Homo sapiens

<400> SEQUENCE: 32
uccccaagug gcucguugua ag                                            22
```